(12) United States Patent
Hauber et al.

(10) Patent No.: US 10,316,301 B2
(45) Date of Patent: Jun. 11, 2019

(54) TAILORED RECOMBINASE FOR RECOMBINING ASYMMETRIC TARGET SITES IN A PLURALITY OF RETROVIRUS STRAINS

(71) Applicants: Heinrich-Pette-Institut, Leibniz-Institut für Experimentelle Virologie, Hamburg (DE); Max-Planck-Gesellschaft Zur Förderung der Wissenschaften E.V., München (DE)

(72) Inventors: Joachim Hauber, Hamburg (DE); Jan Chemnitz, Oederquart (DE); Frank Buchholz, Dresden (DE); Janet Chusainow, Dresden (DE)

(73) Assignees: Heinrich-Pette-Institut, Leibniz-Institut für Experimentelle Virologie, Hamburg (DE); Max-Planck-Gesellschaft Zur Förderung der Wissenschaften E.V., München (DE)

( * ) Notice: Subject to any disclaimer, the term of this patent is extended or adjusted under 35 U.S.C. 154(b) by 0 days.

(21) Appl. No.: 15/348,077

(22) Filed: Nov. 10, 2016

(65) Prior Publication Data

US 2017/0130212 A1  May 11, 2017

Related U.S. Application Data

(63) Continuation of application No. 14/560,795, filed on Dec. 4, 2014, now abandoned, which is a continuation of application No. 13/698,410, filed as application No. PCT/EP2011/002646 on May 27, 2011, now abandoned.

(30) Foreign Application Priority Data

May 27, 2010 (EP) ..................... 10005499

(51) Int. Cl.
| | | |
|---|---|---|
| C12N 9/12 | (2006.01) | |
| C12N 9/22 | (2006.01) | |
| C12N 15/10 | (2006.01) | |

(52) U.S. Cl.
CPC ............ *C12N 9/1241* (2013.01); *C12N 9/22* (2013.01); *C12N 15/1058* (2013.01); *C12N 2740/16022* (2013.01)

(58) Field of Classification Search
None
See application file for complete search history.

(56) References Cited

U.S. PATENT DOCUMENTS

| | | |
|---|---|---|
| 5,994,136 A * | 11/1999 | Naldini ............ C07K 14/005 435/320.1 |
| 6,262,341 B1 | 7/2001 | Baszczynski et al. |
| 6,890,726 B1 | 5/2005 | Sauer et al. |
| 7,112,715 B2 | 9/2006 | Chambon et al. |
| 8,871,516 B2 | 10/2014 | Hauber et al. |
| 2006/0014264 A1 | 1/2006 | Sauer et al. |
| 2009/0217400 A1 | 8/2009 | Carmi et al. |
| 2017/0175091 A1 | 6/2017 | Hauber et al. |

FOREIGN PATENT DOCUMENTS

| | | |
|---|---|---|
| WO | 02/44409 A2 | 6/2002 |
| WO | 2005/081632 A2 | 9/2005 |
| WO | 2008/083931 A1 | 7/2008 |
| WO | 2009/007982 A1 | 1/2009 |
| WO | 2016/034553 A1 | 6/2013 |

OTHER PUBLICATIONS

Arya et al., "New human and simian HIV-related retroviruses possess functional transactivator (tat) gene" 328(6130) Nature 548-550 (1987).*
Wang et al., "HIV integration site selection: Analysis by massively parallel pyrosequencing reveals association with peigenetic modifications" 17(8) Genome Research 1186-1194 (2007).*
Temin, "Function of the retrovirus long terminal repeat" 28(1) Cell 3-5 (1982).*
Abremski et al., "Bacteriophage P1 Site-specific Recombination—Purification and Properties of the Cre Recombinase Protein," *Journal of Biological Chemistry* 259(3):1509-1514, Feb. 10, 1984.
Abremski et al., "Studies on the Properties of P1 Site-Specific Recombination: Evidence for Topologically Unlinked Products following Recombination," *Cell* 32:1301-1311, Apr. 1983.
Adachi et al., "Production of Acquired Immunodeficiency Syndrome-Associated Retrovirus in Human and Nonhuman Cells Transfected with an Infectious Molecular Clone," *Journal of Virology* 59(2):284-291, Aug. 1986.
Alper et al., "Tuning genetic control through promoter engineering," *Proceedings of the National Academy Sciences USA* 102(36):12678-12683, Sep. 6, 2005.
Altschul et al., "Gapped BLAST and PSI-BLAST: A new generation of protein database search programs," *Nucleic Acids Research* 25(17):3389-3402, 1997.

(Continued)

*Primary Examiner* — Nancy J Leith
(74) *Attorney, Agent, or Firm* — Seed IP Law Group LLP

(57) ABSTRACT

The present invention relates to a method for preparing an expression vector encoding a tailored recombinase, which tailored recombinase is capable of recombining asymmetric target sequences within the long terminal repeat (LTR) of proviral DNA of a plurality of retrovirus strains inserted into the genome of a host cell, as well as to the obtained expression vector, cells transfected with this, expressed recombinase and pharmaceutical compositions comprising the expression vector, cells and/or recombinase. Pharmaceutical compositions are useful, e.g., in treatment and/or prevention of retrovirus infection. In particular, asymmetric target sequences present in a plurality of HIV strains are disclosed, as well as tailored recombinases capable of combining these sequences (Tre 3.0 and 4.0) and expression vectors encoding them.

7 Claims, 4 Drawing Sheets
Specification includes a Sequence Listing.

(56) References Cited

OTHER PUBLICATIONS

Beyer et al., "Oncoretrovirus and Lentivirus Vectors Pseudotyped with Lymphocytic Choriomeningitis Virus Glycoprotein: Generation, Concentration, and Broad Host Range," *Journal of Virology* 76(3):1488-1495, Feb. 2002.

Blackard et al., "Transmission of Human Immunodeficiency Type 1 Viruses with Intersubtype Recombinant Long Terminal Repeat Sequences," *Virology* 254:220-225, 1999.

Bloom et al., "Evolving strategies for enzyme engineering," *Current Opinion in Structural Biology* 15:447-452, 2005.

Buchholz et al., "Alteration of Cre recombinase site specificity by substrate-linked protein evolution," *Nature Biotechnology* 19:1047-1052, Nov. 2001.

Buchholz et al., "Different thermostabilities of FLP and Cre recombinases: implications for applied site-specific recombination," *Nucleic Acids Research* 24(21):4256-4262, 1996.

Buchholz et al., "Improved properties of FLP recombinase evolved by cycling mutagenesis," *Nature Biotechnology* 16: 657-662, Jul. 1998.

Chemnitz et al., "Excision of HIV-1 Proviral DNA using Tre-Recombinase: An Experimental Update," *Antiviral Research* 86(1):A31-A32, Apr. 2010.

Chiu et al., "Cellular APOBEC3G restricts HIV-1 infection in resting $CD4^+$ T cells," *Nature* 435:108-114, May 5, 2005.

Chun et al., "Early establishment of a pool of latently infected, resting $CD4^+$ T cells during primary HIV-1 infection," *Proceedings of the National Academy Sciences USA* 95:8869-8873, Jul. 1998.

Coates et al., "Site-directed genome modification: derivatives of DNA-modifying enzymes as targeting tools," *Trends in Biotechnology* 23(8):407-419, Aug. 2005.

Collins et al., "Engineering proteins that bind, move, make and break DNA," *Current Opinion in Biotechnology* 14:371-378, 2003.

Combes et al., "The *Streptomyces* Genome Contains Multiple Pseudo-attB Sites for the φC31-Encoded Site-Specific Recombination System," *Journal of Bacteriology* 184(20):5746-5752, Oct. 2002.

Crameri et al., "DNA shuffling of a family of genes from diverse species accelerates directed evolution," *Nature* 391:288-291, Jan. 1998.

Derossi et al., "Cell Internalization of the Third Helix of the Antennapedia Homeodomain Is Receptor-independent," *Journal of Biological Chemistry* 271(30):18188-18193, Jul. 26, 1996.

Derossi et al., "The Third Helix of the Antennapedia Homeodomain Translocates through Biological Membranes," *Journal of Biological Chemistry* 269(14):10444-10450, Apr. 8, 1994.

Donovan et al., "The end of the beginning for pluripotent stem cells," *Nature* 414:92-97, Nov. 1, 2001.

Donzella et al., "AMD3100, a small molecule inhibitor of HIV-1 entry via the CXCR4 co-receptor," *Nature Medicine* 4(1):72-77, Jan. 1998.

Dybul et al., "Guidelines for Using Antiretroviral Agents among HIV-Infected Adults and Adolescents," *Annals of Internal Medicine* 137 (5, Part 2):381-433, Sep. 3, 2002.

Eddy, "Profile hidden Markov models," *Bioinformatics Review* 14(9):755-763, 1998.

Edelman et al., "Synthetic promoter elements obtained by nucleotide sequence variation and selection for activity," *Proceedings of the National Academy Sciences USA* 97(7):3038-3043, Mar. 28, 2000.

Elliott et al., "Intercellular Trafficking and Protein Delivery by a Herpesvirus Structural Protein," *Cell* 88(2):223-233, Jan. 24, 1997.

Emennan et al., "HIV-1 Regulatory/Accessory Genes: Keys to Unraveling Viral and Host Cell Biology," *Science* 280:1880-1884, 1998.

Fawell et al., "Tat-mediated delivery of heterologous proteins into cells," *Proceedings of the National Academy Sciences USA* 91(2):664-668, Jan. 18, 1994.

Finzi et al., "Identification of a Reservoir for HIV-1 in Patients on Highly Active Antiretroviral Therapy," *Science* 278:1295-1300, 1997.

Flowers et al., "Inhibition of Recombinant Human Immunodeficiency Virus Type 1 Replication by a Site-Specific Recombinase," *Journal of Virology* 71(4):2685-2692, Apr. 1997.

Fraser et al., "Reduction of the HIV-1-infected T-cell reservoir by immune activation treatment is dose-dependent and restricted by the potency of antiretroviral drugs," *AIDS* 14(6):659-669, 2000.

GenBank Accession No. CP000470, "*Shewanella* sp. ANA-1 plasmid 1, complete sequence—Nucleotide—NCBI," download date Feb. 25, 2013, from URL=http://www.ncbi.nlm.nih.gov/nuccore/CP000470, 120 pages.

GenBank Accession No. NZ_ABEW01000015, "*Salmonella enterica* subsp. *enterica* serovar Newport str. SL317 gcontig—Nucleotide—NCBI," download date Feb. 25, 2013, from URL=http://www.ncbi.nlm.nih.gov/nuccore/156105548?report=genbank, 14 pages.

Gulick et al., "Treatment With Indinavir, Zidovudine, and Lamivudine in Adults With Human Immunodeficiency Virus Infection and Prior Antiretroviral Therapy," *The New England Journal of Medicine* 337:734-739, Sep. 11, 1997.

Guzman et al., "Tight Regulation, Modulation, and High-Level Expression by Vectors Containing the Arabinose $P_{BAD}$ Promoter," *Journal of Bacteriology* 177(14):4121-4130, Jul. 1995.

Hartenbach et al., "A Novel Synthetic Mammalian Promoter Derived From an Internal Ribosome Entry Site," *Biotechnology and Bioengineering* 95:547-559, 2006.

Hauber et al., "Identification of cellular deoxyhypusine synthase as a novel target for antiretroviral therapy," *Journal of Clinical Investigation* 115(1):76-85, Jan. 2005.

Hazuda et al., "Integrase Inhibitors and Cellular Immunity Suppress Retroviral Replication in Rhesus Macaques," *Science* 305:528-532, 2004.

Hoess et al., "Mechanism of Strand Cleavage and Exchange in the Cre-lox Site-specific Recombination System," *Journal of Molecular Biology* 181:351-362, 1985.

Indian Office Action, for corresponding Indian Application No. 4814/DELNP/2009, dated Nov. 18, 2014, 3 pages.

Johannes et al., "Directed evolution of enzymes and biosynthetic pathways," *Current Opinion in Microbiology* 9: 261-267, 2006.

Kim et al., "Characterization of Cre-loxP Interaction in the Major Groove: Hint for Structural Distortion of Mutant Cre and Possible Strategy for HIV-1 Therapy," *Journal of Cellular Biochemistry* 80(3):321-327, Mar. 2001.

Koresawa et al., "Synthesis of a New Cre Recombinase Gene Based on Optimal Codon Usage for Mammalian Sytems," *J Biochem.* 127:367-372, 2000.

Krasnow et al., "Site-Specific Relaxation and Recombination by the Tn3 Resolvase: Recognition of The DNA Path between Oriented res Sites," *Cell* 32:1313-1324, Apr. 1983.

Kulkosky et al., "HAART-Persistant HIV-1 Latent Reservoirs: Their Origin, Mechanisms of Stability and Potential Strategies for Eradication," *Current HIV Research* 4:199-208, 2006.

Lalezari et al., "Enfuvirtide, an HIV-1 Fusion Inhibitor, for Drug-Resistant HIV Infection in North and South America," *The New England Journal of Medicine* 348(22):2175-2185, May 29, 2003.

Lee et al., "A Novel Mutant loxP Containing Part of Long Terminal Repeat of HIV-1 in Spacer Region: Presentation of Possible Target Site for Antiviral Strategy Using Site-Specific Recombinase," *Biochemical and Biophysical Research Communications* 253:588-593, 1998.

Lee et al., "An engineered lox sequence containing part of a long terminal repeat of HIV-1 permits Cre recombinase-mediated DNA excision," *Biochemistry and Cell Biology* 78: 653-658, 2000.

Lehrman et al., "Depletion of latent HIV-1 infection in vivo: a proof-of-concept study," *Lancet* 366:549-555, Aug. 13, 2005.

Lewandoski, "Conditional Control of Gene Expression in the Mouse," *Nature Reviews Genetics* 2:743-755, Oct. 2001.

Lin et al., "Enhanced cell-permeant Cre protein for site-specific recombination in cultured cells," *BMC Biotechnology* 4(25):1-13, 2004.

(56) References Cited

OTHER PUBLICATIONS

Little et al., "Antiretroviral-Drug Resistance Among Patients Recently Infected With HIV," *The New England Journal of Medicine* 347(6):385-394, Aug. 8, 2002.
Macara, "Transport into and out of the Nucleus," *Microbiology and Molecular Biology Reviews* 65(4):570-594, Dec. 2001.
Malim et al., "Immunodeficiency virus rev trans-activator modulates the expression of the viral regulatory genes," *Nature* 335:181-183, Sep. 8, 1988.
Marcello, "Latency: the hidden HIV-1 challenge," *Retrovirology* 3(7):1-9, Jan. 2006.
Matsumura et al., "In vitro Evolution of Beta-glucuronidase into a Beta-galactosidase Proceeds Through Non-specific Intermediates," *Journal of Molecular Biology* 305:331-339, 2001.
Minshull et al., "Protein evolution by molecular breeding," *Current Opinion in Chemical Biology* 3:284-290, 1999.
Nagy, "Cre Recombinase: the Universal Reagent for Genome Tailoring," *Genesis* 26:99-109, 2000.
Needleman et al., "A General Method Applicable to the Search for Similarities in the Amino Acid Sequence of Two Proteins," *Journal of Molecular Biology* 48:443-453, 1970.
Nolden et al., "Site-specific recombination in human embryonic stem cells induced by cell-penneant Cre recombinase," *Nature Methods* 3(6):461-467, Jun. 2006.
O'Doherty et al., "Human Immunodeficiency Virus Type 1 Spinoculation Enhances Infection through Virus Binding," *Journal of Virology* 74(21):10074-10080, Nov. 2000.
Oess et al., "Novel cell permeable motif derived from the PreS2-domain of hepatitis-B virus surface antigens," *Gene Therapy* 7(9):750-758, May 2000.
Pearson et al., "Improved tools for biological sequence comparison," *Proceedings of the National Academy Sciences USA* 85:2444-2448, Apr. 1988.
Peitz et al., "Ability of the hydrophobic FGF and basic TAT peptides to promote cellular uptake of recombinant Cre recombinase: A tool for efficient genetic engineering of mammalian genomes," *Proceedings of the National Academy Sciences USA* 99(7):4489-4494, Apr. 2, 2002.
Ratner et al., "Polymorphism of the 3' open reading frame of the virus associated with the acquired immune deficiency syndrome, human T-lymphotropic virus type III," *Nucleic Acids Research* 13(22):8219-8229, 1985.
Richard et al., "Cellular Uptake of Unconjugated TAT Peptide Involves Clathrin-dependent Endocytosis and Heparan Sulfate Receptors," *Journal of Biological Chemistry* 280(15):15300-15306, Apr. 15, 2005.
Rüfer et al., "Non-contact positions impose site selectivity on Cre recombinase," *Nucleic Acids Research* 30(13): 2764-2771, 2002.
Ruhl et al., "Eukaryotic Initiation Factor 5A Is a Cellular Target of the Human Immunodeficiency Virus Type 1 Rev Activation Domain Mediating Trans-Activation," *Journal of Cellular Biology* 123(6, Part 1):1309-1320, Dec. 1993.
Sanger et al., "DNA sequencing with chain-terminating inhibitors," *Proceedings of the National Academy Sciences USA* 74(12):5463-5467, Dec. 1977.
Santoro et al., "Directed evolution of the site specificity of Cre recombinase," *Proceedings of the National Academy Sciences USA* 99(7):4185-4190, Apr. 2, 2002.
Saraf-Levy et al., "Site-specific recombination of asymmetric lox sites mediated by a heterotetrameric Cre recombinase complex," *Bioorganic & Medicinal Chemistry* 14:3081-3089, 2006.
Sarkar et al., "HIV-1 Proviral DNA Excision Using an Evolved Recombinase," *Science* 316:1912-1915, Jun. 29, 2007.
Sauer et al., "DNA recombination with a heterospecific Cre homolog identified from comparison of The pac-c1 regions of P1-related phages," *Nucleic Acids Research* 32(20):6086-6095, 2004.
Schambach et al., "Equal Potency of Gammaretroviral and Lentiviral SIN Vectors for Expression of $O^6$-Methylguanine-DNA Methyltransferase in Hematopoietic Cells," *Molecular Therapy* 13(2):391-400, Feb. 2006.

Scherr et al., "Gene Transfer into Hematopoietic Stem Cells Using Lentiviral Vectors," *Current Gene Therapy* 2:45-55, 2002.
Sclimenti et al., "Directed evolution of a recombinase for improved genomic integration at a native human sequence," *Nucleic Acids Research* 29(24):5044-5051, 2001.
Shehu-Xhilaga et al., "Antiretroviral Compounds: Mechanisms Underlying Failure of HAART to Eradicate HIV-1," *Current Medicinal Chemistry* 12:1705-1719, 2005.
Shimshek et al., "Codon-Improved Cre Recombinase (iCre) Expression in the Mouse," *Genesis* 32(1):19-26, 2002.
Smith et al., "Overlapping Genes and Information Theory," *Journal of Theoretical Biology* 91:379-380, 1981.
Stark et al., "Catalysis by site-specific recombinases," *Trends in Genetics* 8(12):432-439, Dec. 1992.
Stemmer, "Rapid evolution of a protein in vitro by DNA shuffling," *Nature* 370:389-391, Aug. 4, 1994.
Sternberg et al., "Bacteriophage P1 cre Gene and its Regulatory Region—Evidence for Multiple Promoters and for Regulation by DNA Methylation," *J. Med. Biol.* 187:197-212, 1986.
Sternberg et al., "Bacteriophage P1 Site-specific Recombination. I. Recombination Between loxP Sites," *Journal of Molecular Biology* 150:467-486, 1981.
Surendranath et al., "SeLOX—a locus of recombination site search tool for the detection and directed evolution of site-specific recombination systems," *Nucleic Acids Research* 38(Suppl 2):W293-W298, Jul. 2010.
Tan et al., "Fusion Proteins Consisting of Human Immunodeficiency Virus Type 1 Integrase and The Designed Polydactyl Zinc Finger Protein E2C Direct Integration of Viral DNA into Specific Sites," *Journal of Virology* 78(3):1301-1313, Feb. 2004.
Van Duyne, "A Structural View of Cre-loxP Site-Specific Recombination," *Annual Review of Biophysics and Biomolecular Structure* 30:87-104, 2001.
Vivès et al., "A Truncated HIV-1 Tat Protein Basic Domain Rapidly Translocates through the Plasma Membrane and Accumulates in the Cell Nucleus," *Journal of Biological Chemistry* 272(25):16010-16017, Jun. 20, 1997.
Vives, "Cellular utake of the TAT peptide: an endocytosis mechanism following ionic interactions," *Journal of Molecular Recognition* 16:265-271, 2003.
Volkert et al., "Site-Specific Recombination Promotes Plasmid Amplification in Yeast," *Cell* 46:541-550, Aug. 15, 1986.
Voziyanov et al., "Stepwise Manipulation of DNA Specificity in Flp Recombinase: Progressively Adapting Flp to Individual and Combinatorial Mutations in its Target Site," *Journal of Molecular Biology* 326:65-76, 2003.
Yuan et al., "Laboratory-Directed Protein Evolution," *Microbiology and Molecular Biology Reviews* 69(3):373-392, Sep. 2005.
Buchholz et al., "In vitro evolution and analysis of HIV-1 LTR-specific recombinases," *Methods* 53(1):102-109, 2011.
Karpinski et al., "Directed evolution of a recombinase that excises the provirus of most HIV-1 primary isolates with high specificity," *Nature Biotechnology* 34(4):401-409, 2016. (28 pages).
Karpinski et al., "Universal Tre (uTre) recombinase specifically targets the majority of HIV-1 isolates," *Journal of the International AIDS Society* 17(4; Supplement 3):19706, 2014.
Loonstra et al., "Growth inhibition and DNA damage induced by Cre recombinase in mammalian cells," *Proceedings of the National Academy of Sciences of the United States of America* 98(16):9209-9214, 2001.
Coffin, "HIV Population Dynamics in Vivo: Implications for Genetic Variation, Pathogenesis, and Therapy," *Science* 267:483-489 (Jan. 27,1995).
De Arellano et al., "Genetic Analysis of Regulatory, Promoter, and TAR Regions of LTR Sequences Belonging to HIV Type 1 Non-B Subtypes," *AIDS Research and Human Retroviruses* 21(11):949-954 (Nov. 11, 2005).
De Baar et al., "Subtype-Specific Sequence Variation of the HIV Type 1 Long Terminal Repeat and Primer-Binding Site," *AIDS Research and Human Retroviruses* 16(5):499-504 (Nov. 5, 2000).
Mansky, "Retrovirus mutation rates and their role in genetic variation," *Journal of General Virology* 79:1337-1345 (1998).

(56) References Cited

OTHER PUBLICATIONS

Montano et al., "Divergent Transcriptional Regulation among Expanding Human Immunodeficiency Virus Type 1 Subtypes," *Journal of Virology* 71(11):8657-8665 (Nov. 1997).

Nonnemacher et al., "Specific sequence configurations of HIV-1 LTR G/C box array result in altered recruitment of Sp isoforms and correlate with disease progression," *Journal of Neuroimmunology* 157:39-47 (2004).

Perelson, "Modelling Viral and Immune System Dynamics," www.nature.com/reviews/immunol 28(2):28-36 (Jan. 2002).

Sarkar et al., Supporting Online Material for: "HIV-1 Proviral DNA Excision Using an Evolved Recombinase," *Science* 316:1912 (17 pages) www.sciencemag.org/cgi/content/full/316/5833/1912/DC1, (Jun. 29, 2007).

Verhoef et al., "Evolution of the Human Immunodeficiency Virus Type 1 Long Terminal Repeat Promoter by Conversion of an NF-κb Enhancer Element into a GABP Binding Site," *Journal of Virology* 73(2):1331-1340 (Feb. 1999).

\* cited by examiner

Fig. 1

| | | |
|---|---|---|
| loxP (Cre) | ATAACTTCGTATAATGTATGCTATACGAAGTTAT | SEQ ID NO:3 |
| loxH (Fre) | ATATATACGTATATAGACATATATACGTATATAT | SEQ ID NO:4 |
| rox (Dre) | CTAACTTTAAATAATGCCAATTATTTAAAGTTAT | SEQ ID NO:5 |
| zox (Zre) | ATAACTTCGTATAACACACATTATGCGAAGTTAT | SEQ ID NO:6 |
| loxLTR (Tre) | ACAACATCCTATTACACCCTATATGCCAACATGG | SEQ ID NO:7 |
| SEQ ID NO:1 | A<u>ACCCAC</u>TG<u>C</u>TT<u>AAGCCTCAATA<u>AA</u>G<u>CTT</u>G<u>CC</u>TT | |
| SEQ ID NO:2 | <u>CTGGGC</u>GGGA<u>C</u>T<u>GGGGAGTGG</u><u>C</u>GAG<u>CCC</u>T<u>CA</u>GAT | |

Fig. 2

| | | |
|---|---|---|
| SEQ ID NO:1 | A<u>ACCCAC</u>TG<u>C</u>TTAAGCCTCAATA<u>AA</u>GCTTG<u>CC</u>TT | |
| Subsite 1 | A<u>ACCCAC</u>TG<u>C</u>TTAAGCCTCAATAAGCAGTGGGTT | SEQ ID NO:8 |
| Subsite 1b+2 | A<u>AC</u>ACA<u>C</u>TG<u>C</u>TTAAGCCTCAATAAGCAGTGTGTT | SEQ ID NO:27 |
| Subsite 1b+1 | AT<u>C</u>ACA<u>C</u>TG<u>C</u>TTAAGCCTCAATAAGCAGTGTGAT | SEQ ID NO:28 |
| Subsite 1b | ATAACA<u>C</u>TG<u>C</u>TTAAGCCTCAATAAGCAGTGTTAT | SEQ ID NO:29 |
| Subsite 1a | AACCCATTGTATAAGCCTCAATATACAATGGGTT | SEQ ID NO:30 |
| Subsite 1A | A<u>AC</u>ACATTGTATAAGCCTCAATATACAATGTGTT | SEQ ID NO:9 |
| Subsite 1B | ATA<u>CC</u>A<u>C</u>TGTATAAGCCTCAATATACAGTGGTAT | SEQ ID NO:10 |
| Subsite 1C | ATAACATTG<u>C</u>TTAAGCCTCAATAAGCAATGTTAT | SEQ ID NO:11 |
| Subsite 2 | AAGGCAAGCTTTAAGCCTCAATA<u>AA</u>GCTTG<u>CCT</u>T | SEQ ID NO:12 |
| Subsite 2a+2 | AAGGCAAGGTTTAAGCCTCAATA<u>AA</u>CCTTG<u>CCT</u>T | SEQ ID NO:31 |
| Subsite 2a+1 | AAGGCTAGGTTTAAGCCTCAATA<u>AA</u>CCTAG<u>CCT</u>T | SEQ ID NO:32 |
| Subsite 2a | AAGGCTAGGTATAAGCCTCAATATACCTAG<u>CCT</u>T | SEQ ID NO:33 |
| Subsite 2b | ATAACAAGCTTTAAGCCTCAATA<u>AA</u>GCTTGTTAT | SEQ ID NO:34 |
| Subsite 2A | AAGACTAGGTATAAGCCTCAATATACCTAGT<u>C</u>TT | SEQ ID NO:13 |
| Subsite 2B | ATAGCAAGGTATAAGCCTCAATATACCTTG<u>C</u>TAT | SEQ ID NO:14 |
| Subsite 2C | ATAACTAGCTTTAAGCCTCAATA<u>AA</u>GCTAGTTAT | SEQ ID NO:15 |
| ΔloxP | ATAACTTCGT<u>T</u>TAATGTATGCTA<u>AA</u>CGAAGTTAT | SEQ ID NO:35 |
| SEQ ID NO:2 | <u>CTGGGC</u>GGGA<u>C</u>T<u>GGGGAGTGG</u><u>C</u>GAG<u>CCC</u>T<u>CA</u>GAT | |
| Subsite 1 | <u>CTGGGC</u>GGGA<u>C</u>T<u>GGGGAGTGG</u>CAGTCCCGCCAG | SEQ ID NO:16 |
| Subsite 1A | <u>CT</u>GACTTCGA<u>C</u>TAGGGAGTGGTAGTCGAAGTCAG | SEQ ID NO:17 |
| Subsite 1B | ATA<u>GG</u>TTCGAATGGGGAGTGGCATTCGAACCTAT | SEQ ID NO:18 |
| Subsite 1C | ATAAC<u>C</u>GGGAATAGGGAGTGGTATTCCCGGTTAT | SEQ ID NO:19 |
| Subsite 2 | ATCTGAGGGCTCGGGGAGTGG<u>C</u>GAG<u>CCC</u>T<u>CA</u>GAT | SEQ ID NO:20 |
| Subsite 2A | ATCTGTTGGCATGGGGAGTGG<u>C</u>ATGCCAACA<u>G</u>AT | SEQ ID NO:21 |
| Subsite 2B | ATATGATGCTTAGGGGAGTGGTA<u>G</u>CCA<u>T</u>CATAT | SEQ ID NO:22 |
| Subsite 2C | ATATGTGGGCACAGGGAGTGGTGTGCC<u>C</u>ACATAT | SEQ ID NO:23 |

Fig. 5 a) Cre                                    SEQ ID NO:36
b) Tre common consensus sequence 100%      SEQ ID NO:37
c) Tre 3.0 consensus sequence 100%         SEQ ID NO:38
d) Tre 3.0 consensus sequence 95%          SEQ ID NO:39

```
    1           12  15                  30                  44
    MSNLLTVHQNLPALPVDATSDEVRKNLMDMFRDRQAFSEHTWKMLLSVCRSWAAWCKLN a
    MSXXXTXXXXLXALXXDXXSDXXXXXLXXXXRDXXAXSXXTWXXLLSXCRXWXAWCXXX b
    MSXXXTXXXXLSALLXDXXSDXXXXXLXXXXRDXXAXSXXTWXVLLSXCRXWXAWCXXX c
    MSXLXTXHXXLSALLXDXTSDEXRXNLMDVXRDXXAXSEHTWKVLLSVCRXWAAWCXLN d 60                          86      93
    NRKWFPAEPEDVRDYLLYLQARGLAVKTIQQHLGQLNMLHRRSGLPRPSDSNAVSLVMRR a
    XRXXFPXXPXXVRXYLLXLQXRGLXVXTXQQHLXXLNMXHRRXGLXRXXDXXXVSLXXRR b
    XRXXFPXXPXXVRXYLLXLQXRGLXVNTXQQHLAXLNMXHRRXGLXRXXDSXXVSLXXRR c
    NRKXFPAEPEDVRDYLLXLQXRGLAVNTIQQHLAXLNMLHRRXGLPRXXDSXAVSLVXRR d 120                                                      175
    IRKENVDAGERAKQALAFERTDFDQVRSLMENSDRCQDIRNLAFLGIAYNTLLRIAEIAR a
    IRXENVDAGERXKQALAFXRXDXXXXXXLXXXSXXXXDXRXLAXLGXAYNTLLRXXEXXX b
    IRXENVDAGERXKQALAFXRXDXXXXXXLXXXSXXXXDXRXLAXLGXAYNTLLRXSEXXX c
    IRXENVDAGERXKQALAFERTDXXQVRXLMXXSXRXQDIRXLAXLGXAYNTLLRISEIAR d

180
    IRVKDISRTDGGRMLIHIGRTKTLVSTAGVEKALSLGVTKLVERWISVSGVADDPNNYLF a
    XRXXDXSXTGGRXLIHXXXTKTLVSTXGVEKALSLXXTXLXERWXSXSGVAXXXXXXYLF b
    XRXXDXSXTGGRXLIHXXXTKTLVSTXGVEKALSLXXTXLXERWXSXSGVAXXXXXXYLF c
    IRXXDISXTGGRMLIHIXRTKTLVSTAGVEKALSLXVTXLVERWISXSGVAXDPNNYLF d 240             259 262
    CRVRKNGVAAPSATSQLSTRALEGIFEATHRLIYGAKDDSGQRYLAWSGHSARVGAARDM a
    CXXXXXGXAXPXAXXXLSXXXLXXIFXXXHXXXXGAKXXSGXRYXXWSGHSARVGAARDM b
    CXXXXXGXAXPXAXXXLSXXXLXXIFXXXHXXXXGAKXXSGXRYXXWSGHSARVGAARDM c
    CXVRXXGVAXPSATXQLSTSALQGIFAXHXLIYGAKXXSGXRYLAWSGHSARVGAARDM d 300     307     317 320
    ARAGVSIPEIMQAGGWTNVNIVMNYIRNLDSETGAMVRLLEDGD* a
    ARAGVXIXEIMQAGGWXTVXXVMNYIRNLDSEXGAMVRLLEXXX* b
    ARAGVXIAEIMQAGGWXTVXXVMNYIRNLDSEXGAMVRLLEXXX* c
    ARAGVXIAEIMQAGGWTTVXSVMNYIRNLDSETGAMVRLLEXXD* d
```

TAILORED RECOMBINASE FOR RECOMBINING ASYMMETRIC TARGET SITES IN A PLURALITY OF RETROVIRUS STRAINS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 440098_402C2_SEQUENCE LISTING.txt. The text file is 119 KB, was created on Nov. 9, 2016, and is being submitted electronically via EFS-Web.

The present invention relates to a method for preparing an expression vector encoding a tailored recombinase, which tailored recombinase is capable of recombining asymmetric target sequences within the long terminal repeat (LTR) of proviral DNA of a plurality of retrovirus strains which may be inserted into the genome of a host cell, as well as to the obtained expression vector, cells transfected with these, expressed recombinase and pharmaceutical compositions comprising the expression vector, cells and/or recombinase. Pharmaceutical compositions are useful, e.g., in treatment and/or prevention of retrovirus infection. In particular, asymmetric target sequences present in a plurality of HIV-1 strains are disclosed, as well as tailored recombinases capable of combining these sequences (Tre 3.0 and 4.0) and expression vectors encoding them.

TECHNICAL BACKGROUND

Retroviral infections such as for example infections by the human immunodeficiency virus (HIV) are still one of the most important and most widespread human diseases.

One approach to treatment of retrovirus, e.g., HIV, is to target the provirus inserted into the genome of the host cell. Excision of the proviral DNA from the host's genome for example would prevent further HIV replication and differs from current methodologies in that it has the potential to eradicate even dormant virus present in the genome of the host.

One class of proteins that were considered for use in this alternative approach are site-specific recombinases (FLOWERS et al., 1997). Site-specific recombinases mediate a multitude of functions in nature from gene rearrangement to genome segregation, such as for example excision, inversion, or integration of defined DNA units (reviewed in STARK et al., 1992).

One of the simplest and best understood recombinases is the Cre recombinase from bacteriophage P1 that resolves genome dimers into monomers by recombination between two identical double-stranded DNA sites of a particular sequence (HOESS & ABREMSKI, 1985). The Cre recombinase has found widespread use in mouse genetics (NAGY, 2000). Cre is a 38 kDa protein that was named after is function, as it causes recombination (STERNBERG & HAMILTON, 1981). Prerequisite for this recombination is the alignment of two recombination sites recognised by Cre in antiparallel orientation which are then bound by four identical Cre subunits that join to form a ring in which each subunit contacts two adjacent subunits and one half site of one recombination site (HOESS & ABREMSKI, 1985). The recombination site recognised by Cre is a 34-bp double-stranded DNA sequence known as loxP (from locus of crossing over (x), P1; STERNBERG & HAMILTON, 1981), which is palindromic with the exception of its eight innermost base pairs (referred to as the spacer), which impart directionality to the site.

Some site-specific recombination systems, including the Cre/loxP-system function without accessory proteins or cofactors and function under a wide variety of cellular conditions. However, since the site-specific recombinases function through specific interactions of the recombinase enzyme subunits with their cognate DNA target sequences, the use of these enzymes is restricted by the requirement that the targeted DNA regions must contain appropriately positioned target sites (LEWANDOSKI, 2001). To date, no wild-type recombinase has been identified that recognises native retroviral sequences as their DNA target sequences.

Extensive mutational and structural analyses of site-specific recombinases have been carried out in recent years to alter their properties and to achieve a better understanding of the intricate mechanisms of these enzymes (for a review see VAN DUYNE, 2001; and COATES et al., 2005). A lot of studies focussed on the Cre recombinase to explore its evolvability. Several studies demonstrated that Cre target specificity could be altered when few nucleotides in its loxP recognition site were changed (BUCHHOLZ & STEWART, 2001; SANTORO & SCHULTZ, 2002; RUFER & SAUER, 2002). Further studies addresses the engineering of mutated loxP target sites containing sequences from the LTR of HIV-1 to develop possible target sites for the use of Cre as antiviral strategy (LEE & PARK, 1998; LEE et al., 2000).

The method of directed evolution is a powerful method to select enzymes with altered specificities (reviewed in Yuan et al., 2005; and JOHANNES & ZHAO, 2006). In the beginning this method was used to isolate improved enzymes on the basis of RNA by selecting RNA molecules with altered substrate sites. The use of PCR-based methods allows the screening of very large libraries and the recovery of successful coding regions from a pool of candidates. In the directed evolution of proteins, by contrast, the screening for and the recovery of improved mutants, which are identified by alterations in the properties of the protein, requires a method for retrieving the nucleic acid sequence encoding the protein. The link between the protein and its coding sequence has often been maintained by compartmentalisation. Consequently, library screening in directed protein evolution has been limited to "one-by-one" approaches that maintain the compartments, and the advantages associated with screening pools of candidates have not been available.

This limitation has been overcome by the development of methods that allow the crosslinking of proteins to their respective messenger RNAs (mRNAs) using mRNA-protein fusions and ribosome display. Functional screens for improved protein properties were thus coupled to direct retrieval of corresponding coding molecules, and large pools have been screened in vitro (see for example BUCHHOLZ et al., 1998). A further improvement of directed protein evolution was achieved by the so-called substrate-linked protein evolution (SLiPE; BUCHHOLZ & STEWART, 2001), wherein the substrate of the recombinase was placed on the same DNA molecule as the protein coding region. In this manner, when the recombinase was expressed within a compartment, its action altered the DNA substrate next to its own coding region. Consequently, a library could be screened as a pool by PCR to amplify only candidate coding regions that were next to an altered substrate. This allows the screening of large libraries conveniently for rapid retrieval of successful coding regions. This method was applied for altering the DNA specificity of Cre recombinase and adapting it to a new recognition target site (BUCHHOLZ & STEWART, 2001).

In view of the potential of site-specific recombinases and the need of finding an AIDS therapy eradicating HIV-1 provirus from the genome of host cell, WO 2008/083931 disclosed generation of a tailored recombinase (TRE) that is capable of recombining asymmetric target sites within the LTR of proviral DNA of a retrovirus inserted into the genome of a host cell, thus excising the provirus from the genome of the host cell. The engineered recombinase disclosed in the examples, Tre, recognizes a specific loxP-like site present in a particular HIV-1 strain. WO 2008/083931 appreciated that, due to the high sequence variability of retroviruses, in particular, HIV, for treatment of a patient with a different HIV strain, a different tailored recombinase might have to be adapted, or a collection of recombinases prepared containing tailored recombinases specific for a variety or target sequences.

In light of this, the inventors now addressed the problem of providing a tailored recombinase capable of excising a plurality of retrovirus, e.g., HIV strains. Thus, the generated recombinase can be employed for a plurality of HIV infections, without generation of a new recombinase for every strain. This problem is solved by the present invention.

DESCRIPTION OF THE INVENTION

The present inventors for the first time provide a method for generating an expression vector encoding a tailored recombinase capable of recombining asymmetric target sequences within the LTR of proviral DNA of a plurality of retrovirus strains of one species inserted into the genome of a host cell. Recombinases have been tailored to recognise asymmetric target sites different from their native symmetric target sites by splitting up the substrate into a number of new subsets with smaller differences from the original target and stepwise tailoring recombinases to recognise these subsets (WO 2008/083931). A combinatorial approach allows selection of functional molecules recognising the asymmetric target site within a given sequence. Thus, using the approach of traversing through substrate intermediates during directed molecular evolution, it is possible to produce enzymes with remote novel asymmetric target specificities. The present invention employs this approach to the problem of providing tailored recombinases able to recombine a plurality of retrovirus strains, preferably, strains from one species. They found that in spite of the high sequence variability of retroviruses, it is possible to identify asymmetric target sequences present in a high proportion of the viruses of a particular subtype.

The invention provides a method for preparing an expression vector encoding a tailored recombinase, which tailored recombinase is capable of recombining asymmetric target sequences within the LTR of proviral DNA of a plurality of retrovirus strains which may be inserted into the genome of a host cell, comprising steps of identifying in the sequence of the LTR of proviral DNA of a plurality of retrovirus strains sequences with a homology of at least 30% to the left half-site sequence and the right half-site sequence of at least one known recombinase target site, wherein the homologous sequences are separated by a spacer of 5-12 nucleotides, and wherein the asymmetric target sequence is found in a plurality of retrovirus strains; and generating, through repeated steps of i) molecular directed evolution on at least one recombinase recognising the known homologous target site using as substrate modified target sequences based on the sequence of the asymmetric target sequence, but modified to contain only a limited number of variations from the known target sequence; wherein, in each round, the target sequence may vary from the target sequence on which the recombinase is known to act in one, two or three nucleotides; and ii) shuffling the recombinase libraries to obtain recombinase libraries able to recombine target sequences more homologous to the asymmetric target sequence;

until at least one recombinase is obtained that is active on the asymmetric target sequence within the LTR of the retrovirus DNA; isolating the nucleic acid of the least one recombinase obtained; and cloning the nucleic acid encoding the recombinase into a suitable expression vector.

The method of generating a tailored recombinase disclosed in WO 2008/083931 can be used for generating a tailored recombinase capable of recombining an asymmetric target sequence.

The invention also provides a method for preparing an expression vector encoding a tailored recombinase, which tailored recombinase is capable of recombining asymmetric target sequences within the LTR of proviral DNA of a plurality of retrovirus strains which may be inserted into the genome of a host cell, comprising the steps of (a) identifying in the sequence of the LTR of proviral DNA of a plurality of retrovirus strains sequences with a homology of at least 30% to the left half-site sequence and the right half-site sequence of at least one known recombinase target site, wherein the homologous sequences are separated by a spacer of 5-12 nucleotides, and wherein the asymmetric target sequence is found in a plurality of retrovirus strains;

(b) identifying two sequences, wherein the first sequence corresponds to the sequence of the asymmetric target sequence of step (a) homologous to the left half-site of said known target site and is referred to as "half-site sequence 1", and wherein the second sequence corresponds to the sequence of the asymmetric target sequence of step (a) homologous to the right half-site and is referred to as "half-site sequence 2";

(c) determining the nucleotides within the sequences of step (b) deviating from the corresponding homologous left half-site and right half-site sequences of the known homologous target site of step (a);

(d) generating a first subset of two target nucleic acids comprising target sequences, wherein the first target sequence is designated subsite 1 and comprises, adjacent to each other and in 5' to 3' order, half-site sequence 1 of step (b), the spacer sequence of the asymmetric target sequence and an inverted repeat of half-site sequence 1, and wherein the second target sequence is designated subsite 2 and comprises, adjacent to each other and in 5' to 3' order, an inverted repeat of half-site sequence 2, the spacer sequence of the asymmetric target sequence and half-site sequence 2 of step (b);

(e) generating a second subset of target nucleic acids comprising modified target sequences on the basis of the target sequences in the first subset of step (d), wherein, in sequences based on subsite 1, in the left half-site sequence, a portion of the nucleotides deviating from the corresponding homologous half-site sequence of the at least one known target-site of step (a) is replaced by the native nucleotides found in said known target-site, until said half-site sequence contains one, two or three nucleotides deviating from said known target site, wherein the right half-site of said modified target sequence is formed by an inverted repeat of said modified left half-site sequence, which is separated from said modified left half-site sequence by the spacer sequence of the asymmetric target sequence, and wherein, in sequences based on subsite 2, in the right half-site sequence, a portion of the nucleotides deviating from the corresponding homologous half-site sequence of the at least one known target-site of step (a) is replaced by the native nucleotides found in said known target-site, until said half-site sequence contains one, two or three nucleotides deviating from said known target site, wherein the left half-site of said modified target sequence is formed by an inverted repeat of said modified right half-site sequence, which is separated from said modified right half-site sequence by the spacer sequence of the asymmetric target sequence, such that in all modified half-site sequences originating from one target sequence of the first subset of step (d) taken together, all deviating nucleotides can be found, whereas none of said modified half-site sequences alone comprises all deviating nucleotides, (f) separately applying molecular directed evolution on at least one recombinase recognising a known homologous target site according to step (a) using each nucleic acid of the second subset obtained in step (e) as a substrate;

(g) shuffling the recombinase libraries evolved in step (f), wherein all recombinase libraries evolved on sequences based on subsite 1 are combined and shuffled, and wherein all recombinase libraries evolved on sequences based on subsite 2 are combined and shuffled;

(h) applying molecular directed evolution on the shuffled libraries obtained in step (g) using each nucleic acid of the subset according to step (d) as a substrate;

(i) shuffling the recombinase libraries evolved in step (h);

(j) applying molecular directed evolution on the shuffled library obtained in step (g) using a nucleic acid comprising the asymmetric target sequence of step (a) as a substrate, until at least one recombinase is obtained that is active on the asymmetric target sequence within the LTR of the retrovirus DNA of step (a);

(k) isolating the nucleic acid of the least one recombinase obtained in step (j) from the library; and (l) cloning the nucleic acid obtained in step (k) into a suitable expression vector.

In step (a) of the method of the present invention, the sequence of the LTR of the proviral DNA may be determined, such as for example by DNA sequencing using chain-terminating inhibitors (SANGER et al., 1977). However, if the sequence of the LTR of the retroviral DNA inserted into the genome of the host has already been determined, the sequence can be determined by reference to a database. On the basis of the sequence information computer-based analysis of the sequence information is performed to identify therein sequences with homology of at least 30% to the left half-site and the right half-site sequences of known target sites, respectively, of known recombinases that are separated by a suitable spacer of 5-12 nucleotides, wherein the asymmetric target sequence is found in a plurality of retrovirus strains. Preferably, the homology to the left half-site and the right half-site sequences of known target sites is at least 40% or at least 50%. Preferably, these retrovirus strains are of one species or one subtype thereof. Preferably, a plurality of strains comprises more than 10 strains, more preferably, more than 100 strains, more than 130 strains, more than 200 strains or more than 300 strains, e.g., HIV strains. The strains may be from one subtype of the virus, e.g., HIV-1, HIV-1 subtype A and B, or HIV-1 subtype B. Thus, the obtained recombinase or expression vector encoding the same can be used for treatment of infection with a plurality of strains, e.g., more than 50%, more than 70%, more than 80%, more than 90% or all known strains of a retrovirus or subtype thereof.

The term "recombinase" as used herein refers to a protein involved in recombination. As such recombinases recognise and bind two specific DNA sequences termed "recombination sites" or "target sites" and mediate recombination between these two target sites. Accordingly, the term "recombinase" is meant to refer to any protein component of any recombinant system that mediates DNA rearrangements in a specific DNA locus. Naturally occurring recombinases recognise symmetric target sites consisting of two identical sequences termed "half-site" of approximately 9-20 bp forming an inverted repeat, wherein the half-site sequences are separated by a spacer sequence of 5-12 bp. Recombinases from the tyrosine integrase family are characterised by having a tyrosine as the active site nucleophile that is utilised for DNA cleavage, whereas recombinases from the serine integrase family use a serine instead of a tyrosine.

In one embodiment of the present invention, the at least one known recombinase whose target sequence is used in step (a) and upon which molecular directed evolution is applied in steps (h) and (j) belongs to the family of serine integrases. Preferred recombinases belonging to the family of serine integrases are selected from the group consisting of phiC31 integrase (COMBES et al., 2002), any component of Gin or Hin recombination systems, Tn3 resolvase (KRASNOW & COZZARELLI, 1983) or any other member of the large serine recombinases, Rag1, Rag2 or any other component of the VDJ recombination system or variants thereof.

In another embodiment, said recombinase belongs to the family of tyrosine integrases. Preferred recombinases belonging to the family of tyrosine integrases are selected from the group consisting of Cre from Phage P1 (ABREMSKI et al., 1983, 1984), FLP recombinase from yeast (VOLKERT & BROACH, 1986), Dre from phage D6 (SAUER & MCDERMOTT, 2004), R recombinase from *Zygosaccharomyces rouxii* plasmid pSR1, A recombinase from *Kluveromyces dro-sophdarium* plasmid pKD1, a recombinase from the *Kluveromyces waltii* plasmid pKW1, TnpI from the *Bacillus* transposon Tn4430, any component of the λ Int recombination system or variants thereof. Preferably, said recombinase is Cre recombinase or a variant thereof. For example, a tailored recombinase disclosed in WO 2008/083931 (Tre) may be used.

The term variant in this context refers to proteins which are derived from the above proteins by deletion, substitution and/or addition of amino acids and which retain some or all of the function inherent in the protein from which they are derived.

In a preferred embodiment, the known recombinase is a chimeric recombinase obtained by for example "family shuffling" as described by CRAMERI et al. (1998). Prerequisite for the employment of family shuffling is a significant homology between the recombinases used for generating the chimeric recombinases. An example for a chimeric recombinase that can be used in the present invention is a chimeric recombinase consisting of sequences of recombinase Cre and of recombinase Dre, respectively.

In a more preferred embodiment the recombinase is the Cre recombinase recognising a symmetric target site of 34 bp known as loxP (SEQ ID NO:3). The loxP site (and also other recombination sites of wild-type recombinases) is palindromic with two 13 bp repeats separated by the eight innermost base pairs, which represent the so-called spacer, which imparts directionality to the site. Recombination takes place by cleavage within the spacer sequence. Depending on the relative location and orientation of the two participating loxP sites, Cre catalyses DNA integration, excision or rearrangement (HOESS & ABREMSKI, 1985).

One useful recombinase is Zre (SEQ ID NO:26) isolated from *Salmonella enterica*, or variants, fragments and homologues thereof, e.g., having a homology of at least about 70%, at least about 80%, at least about 90% or at least about 95% to the wildtype sequence, and having recombinase function. Zre recombinases recombine DNA at zox sites (FIG. 1). They can be used for starting the method of the invention either alone or in the context of a library.

In one embodiment, a recombinase library is used as a starting point for molecular evolution, e.g., a recombinase library comprising different wildtype and/or adapted/shuffled recombinases, e.g., as described below or in Example 2. Such a library is preferably used as a starting point used for generation of the tailored recombinases able to recognize SEQ ID NO:1 and SEQ ID NO:2.

The tailored recombinase is capable of recombining asymmetric target sequences within the LTR of proviral DNA of a plurality of retrovirus strains. The proviral DNA targeted by the recombinase may be inserted into the genome of a host cell. Alternatively, the tailored recombinase of the invention may recombine asymmetric target sequences within the LTR of proviral DNA of a plurality of retrovirus strains which are not (yet) integrated into the genome of a host cell, i.e. which is present as a non-integrated pre-integration complex (PIC). Thus HIV which has not yet integrated into the genome of the host cell as well as HIV which already has integrated can be inactivated by the tailored recombinase of the invention.

It is to be noted that in the present invention and also in the art the terms "target sequence", "target site" and "recombination site" are used interchangeably.

Contrary to the naturally occurring recombinases recognising symmetric target site, the method of the present invention provides tailored recombinases recognising target sites, which do not consist of palindromic sequences separated by a spacer. Instead, in the asymmetric target sites the sequences do not form a symmetric inverted repeat. Accordingly, a tailored recombinase able to recognise an asymmetrical target site should recognise and recombine target sites consisting of half-sites of varying sequence.

Within an asymmetric target site the sequences referred to as "left half-site" and "right half-site", respectively, are defined by their homology to the left and right half-site of a known target site. The sequence located between the sequences homologous to the left and right half-site of a known target site is referred to as spacer.

However, if sequences are found in the LTR that have only homology to either the left or the right half-site sequence of a known target site, these sequences could nevertheless be used in the practice of the present invention. The size of the target site belonging to the recombinase, whose native target sequence shows homology to sequences within the LTR, is known to the skilled person. For example, if homology is found within the LTR sequence to a target sequence recognised by the Cre recombinase, an asymmetric target site to be recognised by Cre recombinase should consist of 34 nucleotides with two half-site sequences of 13 nucleotides each separated by a spacer of 8 nucleotides. Accordingly, the homologous sequence within the LTR is defined as either the left or the right half-site or the spacer of the asymmetric target site depending on the homology to the sequence of the known target site. Thus, sequences with homology to the left half-site of a known target sequence are defined as left half-site, sequences with homology to the right half-site of a known target sequence are defined as right half-site. Starting from this definition, the other parts of the asymmetric target sites are defined under consideration of the structure of the known target site. Thus, having defined for example a right half-site sequence within the LTR over homology to a loxP site (recognised by Cre recombinase), the other sequences corresponding to the spacer and the left half-site of the asymmetric target sequence can easily be defined. The spacer sequence is for example defined by counting 8 nucleotides upstream of the 5' end of the sequence defined as right half-site sequence, whereas the left half-site sequence is similarly defined by counting 13 nucleotides upstream of the 5' end of the previously defined spacer sequence.

Homology in this context as well as in the whole application means sequence identity. A preferred comparison for homology purposes is to compare at least two sequences using standard techniques known in the art, including, but not limited to, the local homology algorithm of SMITH & WATERMAN (1981), the homology alignment algorithm of NEEDLEMAN & WUNSCH (1970), or the search for similarity method of PEARSON & LIPMAN (1988). For the purposes of the present application sequence homology is preferably determined using the ClustalW computer program available from the European Bioinformatics Institute (EBI), unless otherwise stated.

In view of the requirement of two identical target sites that must be present in the genome of the provirus to allow the recombinase to excise the sequence between these two target sites, sequences of the proviral DNA are scanned in step (a) of the method of the present invention that are present at least twice in the genome. Such sequences are for example the LTR sequences of the proviral DNA. Accordingly, the sequence of the LTR is preferably scanned, since the 5'-LTR and the 3'-LTR of the proviral DNA are identical. An asymmetrical target site present in the 5'-LTR is also present in the 3'-LTR and thus allows for excision of the proviral DNA located between the LTRs.

Out of the sequences identified within the LTR sequence having sufficient homology to known target sites, sequences are preferably chosen that have the highest homology to the sequence of the target site of known recombinases. However, it is also possible to select sequences other than those having the highest homology, e.g., those that are present in the highest number of retrovirus strains, or in the retrovirus strains of interest, e.g., if a patient is infected with a particular strain.

It is to be noted that the potential of the method of the present invention even allows tailoring recombinases that recognise asymmetric target sites with less than 30% homology to known target sites, e.g., at least 11% or at least 20% homology. However, to ensure the presence of residual recombination activity for the respective asymmetric target site, it is preferably scanned for sequences having a homology of at least 30% to the left half-site and the right half-site sequences of known target sites of known recombinases. In further preferred embodiments asymmetric target sequences having a homology of at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80%, more preferably 85%, particularly preferably 90% and most preferably 95% to the left half-site and the right half-site sequences of known target sites of known recombinases are selected.

In one embodiment of the present invention, the sequence selected within the LTR has homology to the symmetric loxP target sites recognised by the site specific recombinase Cre.

In one embodiment, a recombinase library is used as a starting point for molecular evolution, e.g., a recombinase library comprising different wildtype and/or adapted/shuffled recombinases such as the library described in Example 2. An exemplary library comprises Cre and recombinases derived therefrom. It may also comprise Tre, Dre, recombinases from *Salmonella* and *Shewanella* and/or recombinases derived therefrom. The library may comprise, e.g., Cre, Dre, Dre "Cre-ed" (SEQ ID NO: 24), *Shewanella* recombinase (Shew), Shew "Cre-ed" (SEQ ID NO:25), and/or Zre (SEQ ID NO:26). One library is described in FIG. 3A. Tre is a tailored recombinase as disclosed by WO 2008/083931, which is also further referred to as Tre 1.0.

In one embodiment, all recombinases in the library recognize a target sequence with the same length of spacer. The total length of the half-site sequences 1 and 2 including spacer preferably is 34 nucleotides.

If the at least one recombinase is a recombinase library, the homology is homology to the pool of known recombinase target sites (i.e., homology in a given position to at least one of a target sequences is defined as homology). Consequently, in step (c), only those nucleotides which do not correspond to a nucleotide in at least one of the known target sequences are defined as deviating nucleotides. In the case of a recombinase library, a "native nucleotide" in step (e) can be a nucleotide present in that position in any of the known target sequences, preferably, it is a nucleotide present in that position in several or most of the known target sequences.

To identify target sequences present in a plurality of retrovirus strains, the known recognition sites of recombinases, which have been described in literature, can be used as a query for a search for conserved asymmetric target sequences against a genomic stretch. Given the repetitive nature of regions, the use of standard sequence similarity search tools however is precluded. Sarkar et al., 2007, used BLAST (ALTSCHUL et al., 1997) to find a lox-like binding site across HIV strains. The BLAST search for the lox-like site when performed across HIV-1 LTR sequences resulted in the discovery of only one site present in a single strain. If recombinases, however, are to be used as therapeutic agents against retroviral genomes, it is critical to engineer recombinases to target recognition sites present across as many strains of the retrovirus as possible.

As BLAST does not perform well with such short redundant sequences, it was considered to use HMMER (EDDY et al, 1998), RepeatMasker or the palindrome program from the Emboss suite of packages. HMMER was developed to find remote homologs based on a probabilistic model of a sequence pattern being looked for, which is not the nature of the search intended to perform. HMMER could be forced to address this search question, but the amount of pre- and post-processing of data and parameters would make it highly error-prone and inefficient. RepeatMasker only searches for repeats and low complexity regions that are already well characterized, which is again not the nature of this search. The Emboss palindrome program comes closest to addressing the search problem, but does not allow for a search to be defined, but rather results in a list of possibilities of lox-like sites. These would then have to be matched to the lox-site signature of interest. Clearly, such a strategy would only make the search convoluted and cumbersome. To address the lack of a program and a method to find lox-like sites, a program able to search degenerate lox-like sites in genomic sequences had to be developed.

An asymmetric target sequence found in a plurality of retrovirus strains may be identified according to this program, using an algorithm based on a position weight matrix for the flanking regions based on a known recognition site of a recombinase. Preferably, to make the search computationally efficient, binary operations are used on the sequences after they are transformed into bit strings.

In one preferred embodiment of the invention, the retrovirus is HIV, in particular HIV-1. For HIV-1, suitable asymmetric target sequences have been determined, having sequence set forth as SEQ ID NO:1 or SEQ ID NO:2 below.

The left half-site and right half site sequences are underlined and the spacer is printed in bold:

SEQ ID NO: 1
<u>AACCCACTGCTTA</u>AGCCTCAAT<u>AAAGCTTGCCTT</u>

SEQ ID NO: 2
<u>CTGGGCGGGACTG</u>GGGAGTGG<u>CGAGCCCTCAGAT</u>

SEQ ID NO:1 is identical in 92% of the HIV-1 subtype B strains searched (348/379) and in 80% of the HIV-1 subtype A strains searched (32/40). SEQ ID NO:2 is identical in 76% of the subtype B strains searched (288/379). 82% of subtype C strains also comprise this sequence. SEQ ID NO:2 is not present in any of the subtype A strains searched.

As shown in FIG. 1, SEQ ID NO:1 has 54% homology to a pool of known recombinase target sites, and SEQ ID NO:2 has 42% homology to the pool of these sequences (with regard to the left and right half-sites, respectively). Homology to individual known target sites is lower, e.g., at least 30% for SEQ ID NO:1 and at least 11% for SEQ ID NO:2. In particular in the case of low individual homology to known target sites, it can be advantageous to use a library of recombinases as the starting material, e.g., for generating a tailored recombinase capable of recombining SEQ ID NO:1 or SEQ ID NO:2, a library comprising Cre, Fre, Dre, Zre and Tre.

In step (b) of the method of the invention, the sequence of the asymmetric target site within the LTR of the proviruses which is homologous to the left half-site of the known target site is defined as "half-site sequence 1". The sequence of the asymmetric target site within the LTR of the proviruses which is homologous to the right half-site of the known target site is defined as half-site sequence 2. The sequence between the sequences representing the left and the right half-site is referred to as the spacer.

In step (c), the nucleotides within "half-site sequence 1" and "half-site sequence 2", respectively, of the sequences of step (b) deviating from the sequences of the corresponding homologous left half-site and right half-site sequences of the known target are determined by sequence alignment and sequence comparison. In this context, the sequence of "half-site sequence 1" is compared to the corresponding native half-site, which is preferably the left half-site sequence, whereas the sequence of "half-site sequence 2" is compared to other half-site forming the palindromic native target site, which is preferably the right half-site sequence.

FIG. 1 shows the result of this comparison for SEQ ID NO:1 and 2, compared to a library of recombinases. Deviating nucleotides are shown before a dark background.

This comparison must not necessarily performed after step (b) and prior to step (d) of the method of the invention, but can also be performed in a different phase of the method after step (a) and prior to step (e).

In step (d), a first subset of two target nucleic acids comprising target sequences is generated, wherein the first target sequence is designated subsite 1 and comprises, adjacent to each other and in 5' to 3' order, half-site sequence 1 of step (b), the spacer sequence of the asymmetric target sequence and an inverted repeat of half-site sequence 1, and wherein the second target sequence is designated subsite 2 and comprises, adjacent to each other and in 5' to 3' order, an inverted repeat of half-site sequence 2, the spacer sequence of the asymmetric target sequence and half-site sequence 2 of step (b). The target sequences of the first subset are palindromic oligonucleotide sequences having the structure of a symmetric target site. These artificial symmetric target sites are synthesised on the basis of the half-site sequences of step (b) by complementing the missing half-site sequence in each oligonucleotide sequence as inverted repeat, wherein the sequence of "half-site sequence 1" and "half-site sequence 2", respectively, is used to comple-ment the second half-site sequence at the opposite end of the spacer sequence. Accordingly, the first target sequence in the first subset (referred to as "subsite 1") comprises an inverted repeat consisting of the "half-site sequence 1" and the inversely repeated "half-site sequence 1'" separated by the spacer sequence, whereas the second target sequence in the first subset (referred to as "subsite 2") comprises an inverted repeat consisting of the inversely repeated "half-site sequence 2'" and "half-site sequence 2" separated by the spacer sequence. In "subsite 1" the sequence are arranged as follows: 5'-"half-site sequence 1"—spacer-"inverted repeat of half-site sequence 1'"–3', in "subsite 2" the sequence are arranged as follows: 5'-"inverted repeat of half-site sequence 2'"—spacer-"half-site sequence 2"-3'.

The spacer sequences within each two synthetic target sequences of the first subset are preferably identical and correspond to the sequence of the LTR representing or defined as the spacer sequence of the asymmetric target site. However, in a further embodiment, the spacer sequences may comprise one or two sequence deviations originating from nucleotide substitutions.

Generally, this step represents a first split up of the sequences of the asymmetric target site selected for tailoring a specific recombinase (see FIG. 1 of WO 2008/083931, which is fully incorporated herein by reference, and FIG. 2 of the present application). Sequences are generated in this step harbouring symmetric target sites derived from the half-sites of the asymmetric target site selected for tailoring a specific recombinase. As a consequence, each mutation (i.e. difference to the target site recognised by the wild-type recombinase) present in one half-site of said asymmetric target site has now been spread up between the symmetric target sequences in the first subset.

In step (e) of the method of the invention, a second subset of target nucleic acids comprising modified target sequences is generated on the basis of the target sequences in the first subset of step (d). In sequences based on subsite 1, in the left half-site sequence, a portion of the nucleotides deviating from the corresponding homologous half-site sequence of the at least one known target-site of step (a) is replaced by the native nucleotides found in said known target-site, until said half-site sequence contains one, two or three (preferably, two) nucleotides deviating from said known target site, wherein the right half-site of said modified target sequence is formed by an inverted repeat of said modified left half-site sequence, which is separated from said modified left half-site sequence by the spacer sequence of the asymmetric target sequence.

In sequences based on subsite 2, in the right half-site sequence, a portion of the nucleotides deviating from the corresponding homologous half-site sequence of the at least one known target-site of step (a) is replaced by the native nucleotides found in said known target-site, until said half-site sequence contains one, two or three (preferably, two) nucleotides deviating from said known target site, wherein the left half-site of said modified target sequence is formed by an inverted repeat of said modified right half-site sequence, which is separated from said modified right half-site sequence by the spacer sequence of the asymmetric target sequence.

For example, if one subsite comprises six deviating nucleotides, such as both subsites based on SEQ ID NO:1 or subsite 2 of SEQ ID NO:2 with regard to the library of recombinases shown in FIG. 1, three modified target sequences can be generated based on the subsite, which each contain two (different) deviating nucleotides in the left half-site (if based on subsite 1) or right half-site (if based on subsite 2). Consequently, in each modified target sequence, the sequence of the respective subsite is modified to correspond to the sequence of the known target sequence (or at least one known target sequence) in four nucleotides (FIG. 2). Of course, it is also possible to generate six modified target sequences each containing one of the deviating nucleotides, or two target sequences each containing three of the deviating nucleotides.

In another example, if one subsite comprises nine deviating nucleotides, such as subsite 1 of SEQ ID NO:2 with regard to the library of recombinases shown in FIG. 1, three modified target sequences can be generated based on the subsite, which each contain three (different) deviating nucleotides in the half-site.

As a consequence, in all modified half-site sequences originating from one target sequence of the first subset of step (d) taken together, all deviating nucleotides can be found, whereas none of said modified half-site sequences alone comprises all deviating nucleotides, Again, an inverted repeat is generated on the basis of the modified half-site sequence, such that the spacer sequence separates both sequences forming the inverted repeat (see FIG. 2). The spacer sequences within each modified target sequences of a new subset being derived from a target sequence of a higher subset are preferably identical and correspond to the sequence of the LTR representing or defined as the spacer sequence of the asymmetric target site. However, in a further embodiment the spacer sequences may comprise one or two sequence deviations originating from nucleotide substitutions. Using this approach, the number of mutations (i.e. differences to the target site recognised by the wild-type recombinase) in the target sequences representing each subset is smaller than in the starting asymmetric target sequence, but all mutations are still represented in one of the target sequences (see FIG. 1 of WO 2008/083931, FIG. 2 of the present application).

The term "deviating nucleotide" as used herein refers to a nucleotide within the asymmetric target sequence identified or defined within the LTR or within a target sequence of a subset generated according to the present invention that deviates (i.e. is different) from the nucleotide present at the same position in the corresponding homologous sequence of the known homologous symmetric target sequence of a known recombinase chosen in step (a) of the method of the present invention. In this context, the terms "deviating nucleotides" and "mutations" are used interchangeably.

WO 2008/083931 teaches that recombinases can be tailored using molecular directed evolution using target sequences as a substrate, if the target sequence used as a substrate differs in not more than 3 nucleotides from the native target sequence. Thus, the generation of subsets of different orders described above serves to reduce the number of deviating nucleotides per target sequence to 3 or less (see FIG. 1 of WO 2008/083931). The stepwise reduction of the number of deviating nucleotides finally yields a number of subsets of target sequences of different orders with decreasing numbers of deviating nucleotides until a final subset is created that can be used as a substrate for molecular directed evolution. While creating the different subsets and thereby reducing the number of deviating nucleotides, the differences to the target site recognised by the wild-type recombinase are spread between several target sequences that do not comprise more than 3 of these deviating nucleotides each, while the target sequences of the final order as a whole still represent all deviating nucleotides.

Optionally, in the method of the invention, further subsets of target sequences can be generated starting from the target sequences of the second subset by stepwise repeating the process of step (e), i.e. splitting up the target sequences into the respective half-site sequences and generating new palindromic structures on the basis of these half-site sequences after altering the sequence of the half-site derived from a target sequence of the second subset, each time generating a new subset of target sequences, wherein the half-site sequences used for generating the inverted repeats contain less nucleotides deviating from the corresponding homologous half-site sequence of the at least one known target site. These additional target sequences can be used for additional steps of directed molecular evolution and shuffling of recombinase libraries. Of course, such an additional step can also only be performed for some of the sequences, e.g., for sequences wherein recombinases with a low efficiency of recombination are obtained. If additional subsets are generated and recombinases evolved on these, the evolved library of recombinases is used in step (f) of the method of the invention.

Starting from the second subset of target sequences obtained in step (e), a third subset may be generated, followed by a fourth, fifth, sixth etc. subset if necessary. However, the generation of the third subset is generally only necessary, if the target sequences of the second subset still contain more than three deviating nucleotides. The same applies to the generation of the next subsets, which are only necessary, if the target sequences of the prior subset still contain more than three deviating nucleotides. It should be noted that in one embodiment, subsets of target sequences will be generated until the target sequences of the final subset only comprise one deviating nucleotide. Accordingly, depending on the number of deviating nucleotides in each half-site sequence, the number of subsets generated for each half-site sequence of the asymmetric target site may differ. It may for example be necessary to generate only two subsets for the left half-site sequence, whereas three or four subsets must be generated for the right half-site in order spread the deviating nucleotides between several target sequences such that a single target sequence does not comprise more than 3 of these deviating nucleotides.

The principle of generating further subsets of the target sequences for reducing the number of deviating nucleotides to numbers below three is illustrated in FIG. 1 of WO 2008/083931, and FIG. 2 of the present application provides specific examples of modified target sequences.

In step (f), a method of molecular directed evolution is applied on the at least one recombinase recognising a known homologous target site of step (a), using a target sequence of the final or second subset obtained in step (e) containing one, two or three nucleotides deviating from the corresponding homologous half-site sequence of said known homologous target site as a substrate.

The term "final subset" as used herein refers to the last subset generated in step (e), i.e., if no additional subsets are generate, on the second subset. Depending on the number of deviating nucleotides in the asymmetric target site and number of subsets that had to be generated to reduce the number of deviating nucleotide per target sequence below 3, the "final subset" may correspond to any subset, for example the second, third, fourth or a later subset, and may be different for the half-site sequences of the asymmetric target sequence within the LTR. If recombinases have previously been evolved on additional subsets of modified target sequences having less nucleotides deviating from the corresponding homologous half-site sequence of said known homologous target site, the recombinase obtained in that step is used.

Of course, it is possible to start the process of the invention with a specific recombinase for a specific modified target sequence, and with another recombinase (or a library) for another specific modified target sequence.

Methods of molecular directed evolution, also referred to as laboratory evolution or in vitro-evolution, are known in the art (for a review see YUAN et al., 2005 and references therein; JOHANNES & ZHAO, 2006).

In a first step of molecular directed evolution, libraries of randomly mutated recombinase sequences are generated by methods known in the art, e.g. by using error prone PCR and DNA shuffling (reviewed in e.g. YUAN et al., 2005), or the methods disclosed in the International Patent application WO 2002/44409. The plasmids of each library comprising the mutated recombinase also contain one of the target sequences of the final subset obtained in step (f). After transfection of the generated plasmid library into appropriate cells, expression of the recombinase is enabled and the molecular directed evolution is carried out as known by the person skilled in the art.

In a preferred embodiment, the molecular directed evolution employed in step (f) of the method of the present invention is substrate-linked protein evolution (SLiPE; Buchholz & Stewart, 2001; International Patent application WO 02/44409). The substrate-linked protein evolution may be carried out as described in detail in the examples of WO 2008/083931. Briefly, the target sequences obtained in step (e) are cloned into a plasmid (the so-called evolution vector) together with a randomly mutated coding sequence for the recombinase. The random mutation is carried out by error-prone PCR (see BUCHHOLZ & STEWART, 2001). The generated plasmid library is then transfected into *E. coli* cells to allow expression of the recombinase. By using an inducible promoter to drive the expression of the recombinase, it is possible to adjust the expression levels. After overnight incubation, plasmid DNA is isolated from the cells and is digested with NdeI to cut the plasmids that were not recombined and only recombined plasmids are subsequently amplified with primers. The PCR product of the recombined form of the plasmid produces a 1.7 Kb band. The PCR product is digested with BsrGI and XbaI and subcloned back into similarly digested evolution vector for the next evolution cycle.

In step (g), the recombinase libraries evolved in step (f) are combined and shuffled. The technology of DNA shuffling is known in the art (for a reviewed see MINSHULL & STEMMER, 1999; STEMMER, 1994). The recombinase libraries evolved on modified target sequences based on subsite 1 are combined and shuffled, and, separately, the recombinase libraries evolved on modified target sequences based on subsite 2 are combined and shuffled.

The combined and shuffled libraries are then cloned into a new generation of vectors comprising the target sequences of the next higher subset, i.e., if two subsets are generated, the subset generated in step (d). For example, the vector for the library evolved on the sequences based on subsite 1 comprises the sequence of subsite 1 as a target sequence, and the vector for the library evolved on the sequences based on subsite 2 comprises the sequence of subsite 2 as a target sequence.

In step (h), the method of molecular directed evolution is applied on the shuffled libraries obtained in step (g) using the target sequence of the next higher subset, which, as discussed may be the subset according to step (d). In this step, the same method of molecular directed evolution as those applied before in step (f) can be used, but it is also possible to use a different method of molecular directed evolution in this step of the method of the present invention. Examples of different methods of molecular directed evolution were described for example by YUAN et al. (2005). Preferably, the method of substrate-linked protein evolution is also applied on the combined and shuffled libraries.

This step yields recombinases recognising and recombining target sequences harbouring the combination (and thus increasing numbers) of mutations from the different target sequences of the lower subset. The combination of mutations from the different libraries of a lower subset of target sequences results in synergistic effects and leads to the generation of recombinases, which now recombine target sequences of a higher subset, demonstrating that an evolution strategy traversing through intermediates can be used to achieve a desired activity.

In step (i), the steps (g), i.e. combining and shuffling of recombinase libraries, and (j), i.e. the application of molecular directed evolution on the combined and shuffled libraries, are repeated until at least one recombinase is achieved that is active on the asymmetric target sequence present in the LTR of the proviral DNA.

For example, in a method wherein the generation of two subsets of target sequences was necessary to generate target sequences with only one, two or three nucleotide deviations, the recombinase libraries evolved for example for the second subset of target sequences are combined and shuffled and molecular directed evolution is applied on this shuffled library using the target sequences of the first subset. In the next (and final) step the asymmetric target sequence of step (a) within the LTR of the proviral DNA is used to evolve the recombinase library comprising recombinases recognising the target sequences of the first subset by molecular directed evolution to obtain at least one recombinase that is active on the asymmetric target sequence within the LTR of the retroviral DNA. In this step, the method of molecular directed evolution preferably is the method of substrate-linked protein evolution.

In step (k), the nucleic acid of a recombinase having activity on the asymmetric target sequence of step (a) within the LTR of the retroviral DNA is isolated from the library. The nucleic acid is isolated from the respective plasmid within the library using appropriate restriction enzymes. Method of restriction endonuclease digestion are known to skilled person. The nucleic acid encoding the recombinase can than be recovered by known methods such as for example gel electrophoresis.

The nucleic acid may be stored (preferably at temperatures below −80° C.) or may optionally be cloned in step (l) into an expression vector for use in further analysis, in protein expression methods, or for the administration to a subject for treating and/or preventing retrovirus infection, in particular, HIV infection and/or AIDS. Suitable expression vectors are known in the state of the art or disclosed below.

Preferably, the asymmetric target sequence identified in step (a) is localised in both the 5'-LTR and the 3'-LTR of the provirus to allow excision of the proviral DNA from the genome of the host cell.

Using substrate linked directed evolution and the sequences identified in SEQ ID NO:1 and SEQ ID NO:2 as a substrate, the present inventors are producing a tailored recombinase that recombines this asymmetric DNA target sequence present in the HIV-1 long terminal repeats of a plurality of HIV-1 strains. The development of such tailored recombinases that specifically targets asymmetric sequences within a plurality of HIV-1 LTRs allows the excision of the respective provirus from its chromosomal integration for the majority of subjects infected with HIV-1. Thus, in one embodiment, the tailored recombinase is derived from a library of recombinases comprising Cre recombinase, e.g., a library as described in FIG. 3, and it targets a plurality of HIV-1 strains, recognizing the target sequences having the sequence set forth as SEQ ID NO:1 or SEQ ID NO:2. Preferably, the molecular directed evolution is substrate-linked protein evolution (SLiPE). The expression vector encoding the tailored recombinase preferably is derived from a lentiviral vector. This expression vector, cells transfected with it and/or recombinase protein derived therefrom have medical uses, e.g. in treatment and/or prevention of an HIV-1 infection.

In one embodiment, the invention provides a method for preparing an expression vector encoding a tailored recombinase, which tailored recombinase is capable of recombining asymmetric target sequences within the LTR of proviral DNA of a plurality of HIV-1 strains which may be inserted into the genome of a host cell, comprising the steps of (a) identifying SEQ ID NO:1 or SEQ ID NO:2 having homology to the left half-site sequence and the right half-site sequence of the recombinase target sites of a recombinase library comprising the recombinases specified in FIG. 1;

(b) identifying two sequences, wherein the first sequence corresponds to the sequence of the asymmetric target sequence of step (a) homologous to the left half-site of said known target site and is referred to as "half-site sequence 1", and wherein the second sequence corresponds to the sequence of the asymmetric target sequence of step (a) homologous to the right half-site and is referred to as "half-site sequence 2";

(c) determining the nucleotides within the sequences of step (b) deviating from the corresponding homologous left half-site and right half-site sequences of the known homologous target site of step (a), as shown in FIG. 1;

(d) generating a first subset of two target nucleic acids comprising target sequences, wherein the first target sequence is designated subsite 1 and comprises SEQ ID NO:8 (for SEQ ID NO:1), or SEQ ID NO:16 (for SEQ ID NO:2), and wherein the second target sequence is designated subsite 2 and comprises SEQ ID NO:12 (for SEQ ID NO:1), or SEQ ID NO:20 (for SEQ ID NO:2);

(e) generating a second subset of target nucleic acids comprising modified target sequences on the basis of the target sequences in the first subset of step (d), comprising SEQ ID NO:9-11 and 13-15 (for SEQ ID NO:1), or SEQ ID NO:17-19 and 21-23 (for SEQ ID NO:2), respectively, (f) separately applying molecular directed evolution on said recombinase library using each nucleic acid of the second subset obtained in step (e) as a substrate;
(g) shuffling the recombinase libraries evolved in step (f), wherein all recombinase libraries evolved on sequences based on subsite 1 are combined and shuffled, and wherein all recombinase libraries evolved on sequences based on subsite 2 are combined and shuffled;
(h) applying molecular directed evolution on the shuffled libraries obtained in step (g) using each nucleic acid of the subset according to step (d) as a substrate;
(i) shuffling the recombinase libraries evolved in step (h);
(j) applying molecular directed evolution on the shuffled library obtained in step (g) using a nucleic acid comprising the asymmetric target sequence of step (a) as a substrate, until at least one recombinase is obtained that is active on the asymmetric target sequence within the LTR of the retrovirus DNA of step (a);
(k) isolating the nucleic acid of the least one recombinase obtained in step (j) from the library; and
(l) cloning the nucleic acid obtained in step (k) into a suitable expression vector wherein the method of molecular directed evolution preferably is substrate-linked protein evolution.

The TRE recombinase tailored to recognize SEQ ID NO:1 is designated TRE 3.0. The TRE recombinase tailored to recognize SEQ ID NO:2 is designated TRE 4.0.

However, it is obvious for the person skilled in the art that other tailored site specific recombinases can be generated that recombine divergent target sites found in the genome of a plurality of retroviral provirus inserted into the genome of the host cell. Other candidate target sequences can for example be determined which are present in the genome of a plurality of retrovirus strains.

The proviral DNA which may be inserted into the genome of a host cell, or which may not yet be inserted, preferably is the DNA of a retrovirus. Retroviruses comprise a large and diverse family of enveloped RNA viruses. The hallmark feature of the family is its replicative strategy which includes as essential steps the reverse transcription of the viral RNA into linear double-stranded DNA and the subsequent integration of this DNA (proviral DNA) into the genome of the host cell. Retroviruses are subdivided into seven groups, defined by evolutionary relatedness. Five of these groups (alpha-, beta-, delta-, epsilon-, and gamma-retrovirus) represent retroviruses with oncogenic potential, and the other two groups are the lentiviruses and the spumaviruses. The human pathogenic human T cell leukemia viruses type I and type II (HTLV-I and HTLV-II) belong to the delta-retrovirus group, while the AIDS viruses human immunodeficiency virus type 1 and type 2 (HIV-1 and HIV-2) belong to the lentivirus group (for a review see the standard textbook "Retroviruses" of COFFIN J M, HUGHES SH, VARMUS HE (Eds.) 1997, Cold Spring Harbor Laboratory Press, New York).

In one embodiment, the proviral DNA which may be inserted into the genome of a host cell is the DNA of a retrovirus selected from the group consisting of Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV).

In another embodiment, the retrovirus is a lentivirus selected from the group consisting of Human immunodeficiency virus Type 1 (HIV-1), Human immunodeficiency virus Type 2 (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV). As stated above, HIV, in particular HIV-1 is preferred.

In a more preferred embodiment, the asymmetric target sequence identified in step (a) of the method of the present invention is localised in both the 5'-LTR and the 3'-LTR of a HIV provirus. Preferably, said asymmetric target sequence localised in both the 5'-LTR and the 3'-LTR of a HIV provirus has the sequence set forth as SEQ ID NO: 1 or SEQ ID NO:2.

In a preferred embodiment, the method of molecular directed evolution applied in the method of the present invention is the method of substrate-linked protein evolution (SLiPE; BUCHHOLZ & STEWART, 2001; see also WO 02/44409).

By carrying out the method of the invention as described herein, the inventors generated several nucleic acids encoding a tailored recombinase, and the tailored recombinases themselves. The invention thus provides a tailored recombinase comprising a sequence according to any of SEQ ID NO: 40-64 or consisting thereof, or nucleic acids encoding it.

It was surprisingly found that these tailored recombinases preferably comprise certain consensus sequences as shown in FIG. 5. In particular, all analysed tailored recombinases capable of recombining an asymmetric target sequence comprise a sequence according to SEQ ID NO: 37 ("Tre common" consensus sequence). It was further found that all analysed tailored recombinases capable of recombining the target sequence according to SEQ ID NO: 1 comprise a sequence according to SEQ ID NO: 38. 95% of all analysed tailored recombinases capable of recombining the target sequence according to SEQ ID NO: 1 comprise a sequence according to SEQ ID NO: 39. In SEQ ID NO: 37, 38 and 39, variable amino acids are represented by an X (cf. FIG. 5).

The invention thus provides to a tailored recombinase capable of recombining asymmetric target sequences within the LTR of proviral DNA of a retrovirus strain which may be inserted into the genome of a host cell (i.e., a functional tailored recombinase), which preferably comprises SEQ ID NO: 37. Preferably, said tailored recombinase is capable of recombining asymmetric target sequences within the LTR of proviral DNA of a plurality of retrovirus strains which may be inserted into the genome of a host cell. Such a tailored recombinase is e.g. obtainable according to the method of the invention. Preferably, said tailored recombinase comprises SEQ ID NO: 37 and comprises at least one, preferably, 2, 3, 4, 5, 6, or 7 of the following defined amino acids exchanges as compared to the Cre sequence (SEQ ID NO: 36): P12S, P15L, M44V, K86N, G93A, A175S, P307A. These exchanges render the enzyme particularly suited for recombination at a target sequence of SEQ ID NO: 1 or a target sequence having a high sequence identity to SEQ ID NO: 1 (e.g., at least 80%, at least 90% or at least 95% sequence identity to SEQ ID NO: 1).

In one embodiment, the sequence of the tailored recombinase of the invention, in particular, the tailored recombinase comprising SEQ ID NO: 37 is not disclosed in WO 2008/083931. Preferably, the sequence does not comprise SEQ ID NO: 65 of the present application (which is identical to SEQ ID NO: 3 of WO 2008/083931), or positions 11-351 of SEQ ID NO: 65, and the sequence of the nucleic acid encoding a tailored racombinase of the invention does not encode a protein comprising positions 11-351 of SEQ ID NO: 65. The sequence of the tailored recombinase of the invention comprising SEQ ID NO: 37 also varies from the naturally occurring recombinases such as Cre, Dre, Fre or Zre, which is evident from the feature that it is capable of recombining asymmetric target sequences within the LTR of proviral DNA of a retrovirus strain which may be inserted into the genome of a host cell, and, preferably, that it is capable of recombining asymmetric target sequences within the LTR of proviral DNA of a plurality of retrovirus strains which may be inserted into the genome of a host cell.

If the tailored recombinase capable of recombining asymmetric target sequences within the LTR of proviral DNA of a plurality of retrovirus strains inserted into the genome of a host cell is to recombine the target sequence of SEQ ID NO: 1, it preferably comprises SEQ ID NO: 38 or SEQ ID NO: 39.

Functional tailored recombinases capable of recombining asymmetric target sequences within the LTR of proviral DNA of a plurality of retrovirus strains which may be inserted into the genome of a host cell, which may e.g., be obtained by the method of the invention, may vary from said sequences, but the sequences provide valuable guidance to the skilled person to produce a tailored recombinase capable of recombining asymmetric target sides, such as SEQ ID NO: 1, even without carrying out the method of the invention. The invention also provides a tailored recombinase comprising sequences having at least 97% sequence identity to SEQ ID NO: 38, and/or having at least 98% sequence identity to SEQ ID NO: 38 and/or having at least 99% sequence identity to SEQ ID NO: 38. Preferably, a tailored recombinase has at least 97% sequence identity to SEQ ID NO: 39, and/or at least 98% sequence identity to SEQ ID NO: 39 and/or at least 99% sequence identity to SEQ ID NO: 39. Having a certain percentage of sequence identity to a sequence of SEQ ID NO: 37, 38 or 39 in the context of the present invention means sequence identity to the positions defined in the respective sequence, e.g., with 97% sequence identity, 3% of the defined amino acid positions of said sequences may vary. Preferably, amino acid exchanges with regard to the reference sequences are conservative substitutions, which are well known to the skilled person (eg. Creighton (1984), Proteins. W. H. Freeman and Company (Ed.)). For example, conservative substitutions substitute one amino acid from the group of negatively charged amino acids by another.

The tailored recombinases capable of recombining asymmetric target sequences within the LTR of proviral DNA of a plurality of retrovirus strains which may be inserted into the genome of a host cell may also comprise a combination of 2, 3, 4 or more sequences selected from the group consisting of SEQ ID NO: 40-64, e.g., a C-terminal part of any of these sequences, e.g., SEQ ID NO: 40, and the N-terminal part of any other of these sequences, e.g., SEQ ID NO: 64. The C-terminal part may have a length of 1-342 amino acids. In a combination of two sequences, the N-terminal part may have a length of 1-342 amino acids. The combination in any case comprises a TRE consensus motiv, e.g., SEQ ID NO: 37, or preferably, SEQ ID NO: 38 or SEQ ID NO: 39.

The invention further provides composition comprising two or more tailored recombinases comprising different sequences according to SEQ ID NO: 37, preferably, SEQ ID NO: 38 or SEQ ID NO: 39, or nucleic acids encoding them. In one embodiment, the composition comprises two or more, three or more, four or more, five or more, ten or more, 20 or more or 25 recombinases comprising sequences according to any of SEQ ID NO: 40-64 or nucleic acids encoding them. Such compositions may be pharmaceutical compositions as described below.

The invention also provides a nucleic acid encoding a tailored recombinase capable of recombining asymmetric target sequences within the LTR of proviral DNA of a plurality of retrovirus strains which may be inserted into the genome of a host cell, the tailored recombinase comprising an amino acid sequence as defined above. In preferred embodiments, said an amino acid sequence has at least 97% sequence identity to a sequence according to SEQ ID NO: 38, at least 98% sequence identity to a sequence according to SEQ ID NO: 38 or at least 99% sequence identity to SEQ ID N: 38, or comprises SEQ ID NO: 38. The invention also provides a nucleic acid encoding a tailored recombinase comprising an amino acid sequence having at least 97% sequence identity to a sequence according to SEQ ID NO: 39, at least 98% sequence identity to a sequence according to SEQ ID NO: 39 or at least 99% sequence identity to SEQ ID N: 38, or an amino acid sequence comprising SEQ ID NO: 39. The invention also provides a nucleic acid encoding a tailored recombinase comprising an amino acid sequence selected from the group consisting of SEQ ID NO: 40-64 or a combination of said sequences.

In the context of the invention, a nucleic acid or a protein comprising a sequence may also consist of this sequence.

It may also comprise further sequences, e.g., a signal sequence providing for expression/localisation in a specific cellular compartment such as a nuclear localization signal (e.g., the signal in positions 2-9 of SEQ ID NO: 65). If a protein is to be used in a pharmaceutical composition, it is especially preferred to express it as a fusion protein with a protein transduction domain such as the tat protein transduction domain, which allows for protein transduction of target cells. Preferably, a tailored recombinase of the invention which is to be used in a pharmaceutical composition is prepared as a fusion protein with a nuclear localization sequence and with a protein transduction domain e.g. from tat, and a nucleic acid encoding a tailored recombinase of the invention may encode such a fusion protein. For example, the following protein transduction domains may be used in a fusion protein with a tailored recombinase of the invention, which preferably further includes a nuclear localization signal:

Basic domain of HIV-1 Tat transactivator (Fawell S, Seery J, Daikh Y, Moore C, Chen L L, Pepinsky B, Barsoum J., Tat-mediated delivery of heterologous proteins into cells, Proc Natl Acad Sci USA. 1994 Jan. 18; 91(2): 664-8.)

Homeodomain of Drosohila antennapedia (Antp) (Derossi D, Joliot A H, Chassaing G, Prochiantz A., The third helix of the Antennapedia homeodomain translocates through biological membranes, J Biol Chem. 1994 Apr. 8; 269(14):10444-50.)

HSV VP22 transcription factor (Elliott G, O'Hare P., Intercellular trafficking and protein delivery by a herpesvirus structural protein, Cell. 1997 Jan. 24; 88(2): 223-33.)

Cell permeable translocation motif (TLM) of PreS2 surface antigen of Hepatitis B virus (HBV) (Oess S, Hildt E., Novel cell permeable motif derived from the PreS2-domain of hepatitis-B virus surface antigens, Gene Ther. 2000 May; 7(9):750-8.).

In case the protein is to be purified, a tag facilitating purification of a protein such as a His tag, may also be added.

The codon usage of the nucleic acid of the invention encoding a Tre recombinase as defined above can be chosen by the skilled person. For example, a codon usage suitable for expression in a human cell may be chosen, in particular, if expression in a human cell is intended, e.g., for therapeutical purposes. Codon usage may also be based on codon usage of e.g., Cre recombinase.

The tailored recombinase or nucleic acid encoding said tailored recombinase may be obtained by the method of the invention as described herein, or it may be obtainable by this method. It may also be obtained based on the sequences disclosed herein, optionally, by combining and/or further varying these sequences, optionally testing for activity in recombination of asymmetric target sites, such as SEQ ID NO: 1 or SEQ ID NO: 2.

The invention further provides for a composition, e.g., a library, comprising two or more of the nucleic acids encoding a tailored recombinase as defined above, e.g., encoding two or more tailored recombinases comprising different sequences according to SEQ ID NO: 37, preferably, different sequences according to SEQ ID NO: 38 or SEQ ID NO: 39. In one embodiment, the composition comprises nucleic acids encoding tailored recombinases comprising two or more, three or more, four or more, five or more, ten or more, 20 or more or 25 or more recombinases comprising sequences according to any of SEQ ID NO: 40-64 or combinations of these sequences. Such compositions, in particular compositions wherein the nucleic acid is an expression vector, may be particularly suitable as pharmaceutical compositions as described below.

In the method of the present invention, the nucleic acid encoding the at least one tailored recombinase that is active on the asymmetric target sequence within the LTR of the retroviral DNA is cloned into an expression vector. Expression vectors are genetic constructs for expressing the proteins encoded by the nucleic acids within the vector. Such expression vectors may be either self-replicating extrachromosomal vectors or vectors which integrate into a host genome. Generally, these expression vectors include transcriptional and translational regulatory nucleic acid operably linked to the nucleic acid encoding the tailored recombinase of the present invention.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilise promoters, polyadenylation signals, and enhancers.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the tailored recombinase. Numerous types of appropriate expression vectors, and suitable regulatory sequences are known in the art for a variety of host cells.

The expression vector used in the present invention may be a retroviral vector, a lentiviral vector, a spumavirus vector or an adenoviral vector. However, in a preferred embodiment the expression vector is a lentiviral vector selected from the group consisting of HIV-1-, SIV-, FIV- or EIAV-derived lentiviral vectors. Lentiviral vectors are for example described by SCHAMBACH et al. (2006) or in European Patent Application No. 11000751.5.

In preferred embodiments of the present invention the expression vector comprises a cellular, bacterial, a viral or a hybrid promoter.

In general, for the purpose of the present invention, the promoter may be a constitutive or an inducible promoter. Further, the promoters may be either a naturally occurring promoter, such as a bacterial, cellular or a viral promoter, or a hybrid promoter. Hybrid promoters, which combine elements of more than one promoter, are known in the art, and are useful in the present invention. Further, the promoter used in the present invention may also be a derivative of a naturally occurring promoter. A "derivative" of a naturally occurring promoter as used herein may be a combination of cis-active elements obtained from promoters or sequences of different origin or, alternatively, may be obtained by deletion or mutation of cis-active elements within a specific naturally occurring promoter (EDELMAN et al., 2000; ALPER et al., 2006; HARTENBACH & FUSSENEGGER, 2006).

In an embodiment of the present invention, the constitutive promoter or derivative thereof is selected or derived from the group consisting of promoters of cytomegalovirus, Rous sarcoma virus, murine leukemia virus-related retroviruses, phosphoglycerokinase gene, murine spleen focus-forming virus or human elongation factor 1 alpha.

In a further embodiment of the present invention, the inducible promoter or derivative thereof is selected or derived from the group consisting of the LTR or derivatives thereof derived from lentiviruses, spumaviruses and deltaretroviruses.

In this context, the term "LTR" refers to both the 5' and the 3' long terminal repeats of provirus having promoter function (for a review see the standard textbook "Retroviruses" (COFFIN J M, HUGHES S H, VARMUS H E (Eds.) 1997, Cold Spring Harbor Laboratory Press, New York)).

Preferably, the inducible promoter or derivative thereof is selected or derived from the LTR or derivatives thereof derived from HIV-1, HIV-2, MVV, EIAV, CAEV, SIV, FIV, BIV, HTLV-I and HTLV-II.

The present invention further provides a method for preparing a tailored recombinase, wherein said method comprises the aforementioned method for preparing an expression vector encoding a tailored recombinase, and the further step of expressing the tailored recombinase or a fusion polypeptide comprising the amino acid sequence of said tailored recombinase from the nucleic acid encoding the recombinase inserted into the expression vector obtained in the aforementioned method for preparing an expression vector encoding a tailored recombinase in a suitable host cell.

Preferably, the recombinases finally obtained are tested in mammalian cells to ensure that they function in a mammalian cell environment. Further, to obtain good expression in mammalian cells the recombinases may be optimised for expression in these cells (e.g. codon usage optimisation using methods well known in the art. See for example SHIMSHEK et al., 2002) or signal sequences necessary for directing the protein into the nucleus of the mammalian cell, such as the NLS sequence (MACARA, 2001) may be added to the nucleic acid of the tailored recombinase.

Expression of the nucleic acid encoding the tailored recombinase cloned into an expression vector, e.g., according to step (1) of the method for preparing an expression vector encoding a tailored recombinase, can be carried out using for example bacterial, insect or mammalian expression systems. However, other expression systems known in the art may also be employed. Methods of introducing exogenous nucleic acid into mammalian, insect or bacterial hosts, as well as other hosts, are also well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Fusion proteins are prepared by methods well known in the art. For example, the expression vector the nucleic acid encoding the tailored recombinase is cloned into already comprises a nucleic sequence encoding a second polypeptide or protein. By cloning the nucleic acid encoding the tailored recombinase in frame with the sequence of the second polypeptide or protein, both sequences will be expressed as fusion protein.

The host cells used for expressing the tailored recombinase from the expression vector are preferably host cells including prokaryotic cells, such as for example bacterial cells or yeast cells, or eukaryotic cells, such as for example insect cells or mammalian cells. The host cell may be a hematopoietic cell, e.g., an adult hematopoietic stem cell or a T-cell, e.g., a CD4+ cell. The cell may be derived from a subject infected with the retrovirus, and the cell may be administered back to the subject after transformation, and, optionally, cultivation and/or propagation.

The present invention further provides a method for preparing a transformed adult stem cell, wherein said method comprises the aforementioned method for preparing an expression vector encoding a tailored recombinase and the further step of introducing the expression vector obtained in the aforementioned method for preparing en expression vector encoding a tailored recombinase in vitro into a suitable adult stem cell.

In a further aspect, the present invention is directed to the nucleic acid as obtainable from the aforementioned method of the present invention. Nucleic acids encoding a tailored recombinase defined by a sequence are also provided herein.

A "nucleic acid" as used herein is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

In its broadest aspect, the nucleic acid obtained by the method of the present invention or defined herein is a nucleic acid encoding a tailored recombinase, wherein the tailored recombinase recombines asymmetric target sequences within the DNA of a provirus from a plurality of virus strains which may be inserted into the genome of a host cell, leading to excision of the provirus from the genome of the host cell, wherein the asymmetric target sites are different from the target sites of the wild-type recombinase.

In a further aspect, the present invention is also directed to the expression vector as obtainable from the aforementioned method of the present invention, and to an expression vector comprising the nucleic acid encoding a tailored recombinase as defined herein.

The term "protein" as used herein includes proteins, polypeptides, and peptides. As will be appreciated by those in the art, the nucleic acid sequences of the invention can be used to generate protein sequences. A further aspect of the invention is the tailored recombinase protein as obtainable, e.g., from the aforementioned method of the present invention, which recombinase may optionally be a fusion protein comprising a functional recombinase. In one embodiment, the tailored recombinase protein may be prepared as a fusion polypeptide, using techniques well known in the art. In a preferred embodiment, the tailored recombinase protein is linked to a second polypeptide. Preferably the fusion polypeptide is obtained from the aforementioned method of the present invention, wherein the tailored recombinase is linked to a second polypeptide.

In one embodiment, the tailored recombinase protein is prepared as a fusion polypeptide to increase expression. In a further embodiment, the tailored recombinase protein is made as a fusion polypeptide to allow introduction of the polypeptide into living cells. Typically, purified proteins cannot enter into cells, because they are not able to pass the cell membrane due to their size. However, fusion of specific peptides sequences to proteins can result in the uptake of these fusion proteins into cells. In the cell the protein can then perform its function. Site specific recombinases, including Cre recombinase, have been successfully delivered into cells with this approach (PEITZ et al., 2002). Cell-permeant recombinase have further been described by NOLDEN et al. (2006) and LIN et al. (2004). Hence, this strategy may be used to deliver the tailored recombinases into cells to remove the provirus from infected cells. Thus, the second polypeptide in the fusion polypeptide may comprise a signal peptide. The signal peptide may be a protein transduction domain such as the TAT peptide or a peptide from the third helix of the Antennapedia homeodomain (DEROSSI et al., 1994, 1996; VIVES et al., 1997; VIVES, 2003; RICHARD et al., 2005) or the NLS (nucleus localisation sequence) for delivering the fusion polypeptide into the nucleus of an eukaryotic cell (MACARA, 2001).

A further aspect of the present invention is directed to the adult stem cell as obtainable from the aforementioned method for preparing a transformed adult stem cell of the present invention. The stem cells are preferably infected or transfected with the expression vector according to the invention. In a preferred embodiment, the adult stem cell is a stem cell from the hematopoietic lineage expressing the tailored recombinase, the aforementioned fusion polypeptide or comprising the aforementioned expression vector. Hematopoietic stem cells (HSC) are bone marrow-derived CD34+ cells, which can e.g. be purified from G-CSF-mobilised peripheral blood of donors (e.g., HIV-infected patients) by routine leukapheresis (SCHERR & EDER, 2002). The in vitro genetically modified cells may then be formulated for reinfusion into the patients.

In the state of the art, the term "stem cells" designates cells which (a) have the capability of self-renewal and (b) the capability to form at least one and often a number of specialised cell types due to their asymmetrical division capability (DONOVAN & GEARHART, 2001). Adult stem cells can be isolated from different tissues of adult, i.e. from differentiated individuals. Such stem cells are referred to in the state of the art as "multipotent adult stem cells". The essential difference between embryonic pluripotent stem cells and adult multipotent stem cells lies in the number of differentiated tissues which can be obtained from the respective cells.

In a further embodiment, the expression vector of the present invention is used for transforming T-cells, e.g., CD4+ primary cells (blood cells) of retrovirus (e.g., HIV)-infected patients.

In a further step of the method of the present invention, the expression vector comprising the nucleic acid sequence encoding a tailored recombinase of the invention, the recombinase protein, the fusion protein or the adult stem cell obtained by the methods of the present invention are formulated as a pharmaceutical composition for use in prevention and/or treatment of a retrovirus infection and/or for the reduction of the viral load in a subject infected by a retrovirus, e.g., HIV, in particular, HIV-1.

A further object of the invention is the pharmaceutical composition obtained by the aforementioned method. The pharmaceutical composition is preferably present in the form of a solution suitable for intravenous application (infusion).

The pharmaceutical preparation may further comprise one or more pharmaceutically acceptable carrier(s), excipient(s) and/or adjuvant(s). Carriers, excipients and adjuvants suitable for use in a pharmaceutical composition are known in the art.

The pharmaceutical composition of the present invention preferably reduces the virus load in a subject infected by a retrovirus below 5.000 genome equivalents/ml plasma, preferably below 500 genome equivalents/ml plasma and more preferably below 50 genome equivalents/ml plasma when administered to the subject. Thus, the pharmaceutical composition of the present invention comprising an expression vector encoding a tailored recombinase (or the tailored recombinase as a protein or fusion polypeptide or a stem cell comprising the expression vector) is capable of reducing the virus load in a subject infected with a retrovirus by eradicating the genetic reservoir of retroviruses within hosts cells, thereby preventing further life cycles of the virus.

The term "virus load" as used herein refers, e.g., to the HIV RNA equivalents (i.e. genomes) that are associated with 1 ml of the patient's plasma (DYBUL et al., 2002). Thus, the virus load is determined by measuring the content of viral DNA in s sample obtained from the patient. Currently, there are three main types of viral load assays available:

1) HIV RNA reverse transcription-polymerase chain reaction (RT-PCR): Amplicor™ HIV-1 Monitor Test; Roche Diagnostics
2) Branched chain DNA (bDNA): Versant™ HIV RNA Assay; Bayer Diagnostics; and
3) Nucleic acid sequence-based amplification (NASBA): NucliSens™ Assay; bioMerieux.

In a preferred embodiment, the pharmaceutical composition of the present invention is capable of reducing the virus load in a subject infected by a retrovirus below 5.000 genome equivalents/ml plasma, preferably below 500 genome equivalents/ml plasma and more preferably below 50 genome equivalents/ml plasma. Patient with a virus load of below 5000 genome equivalents/ml plasma are considered to be relatively well adjusted to the medicinal treatment. However, the goal in current AIDS therapy is a reduction of the viral load below the detection limit of the virus load assays, which is currently below about 50 genome equivalents/ml plasma.

The pharmaceutical composition preferably reduces the viral load of retroviruses selected from the group consisting of the Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV). In yet a further preferred embodiment retrovirus to be treated with the pharmaceutical of the present invention is a lentivirus. Said lentivirus is preferably selected from the group consisting of Human immunodeficiency virus Type 1 (HIV-1), Human immunodeficiency virus Type 2 (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV). Most preferably, the retrovirus is HIV, in particular HIV-1. However, it is obvious to the person skilled in the art that the present invention is also applicable to retroviral infections by other retroviruses than those mentioned above.

The subject infected by a retrovirus, to whom the pharmaceutical composition is to be administered, is selected from the group consisting of humans, primates, monkeys, cattle, horses, goats, sheep and domestic cats. However, the subject is preferably a human being.

In general, an effective amount of the expression vector, the tailored recombinase or the transformed cell of the invention is to be administered to the subject. Administration may be, e.g., intravenous or intramuscular administration.

In one embodiment, the pharmaceutical composition is formulated for concomitant administration with other active agents of the highly active antiretroviral therapy (HAART). The highly active antiretroviral therapy HAART is a combination therapy targeting the viral reverse transcriptase, protease and fusion (GULICK et al., 1997; LALEZARI et al., 2003).

In another embodiment, the pharmaceutical composition is formulated for administration concomitant or subsequent to global immune activation therapy or specific activation of provirus gene expression. The premise of immune activation therapy is based on the hypothesis that deliberate activation of latently HIV-infected cells may accelerate eradication of persistent viral reservoirs. Eradication would occur via immune clearance by programmed death of those cells actively expressing HIV-1 (pro-apoptotic) products (KULKOSKY & BRAY, 2006). Global immune activation (activation of immune cells, including resting cells) is usually achieved by, for example, administration of immunotoxins, cytokines (e.g., IL-2), or T cell activating antibodies (e.g., OKT3).

In view of the fact that immune activation conducted to deliberately activate HAART-resistant latent reservoirs did unfortunately fail to permanently eliminate HIV-1 and viral rebound (for reviews see KULKOSKY & BRAY 2006; MARCELLO, 2006; SHEHU-XHILAGA et al., 2005) due to the fact that global T cell activation apparently also induces viral replication and increases the number of potential HIV-1 target cells beyond the level that can be contained by HAART (FRASER et al., 2000), further specific treatments are necessary to treat HIV. One approach is the activation of transcription of otherwise quiescent viral genomes. Specific activation of latent provirus gene expression may be achieved by administration of the phorbol ester Prostratin or the human cytokine IL-7, which both appear to reactivate latent HIV-1 in the absence of cellular proliferation (MARCELLO, 2006). Moreover, the selective transcriptional activation of HIV-1 may also be achieved by histone-deacetylase (HDAC1)-inhibitors such as, for example, valproic acid, that eventually induces outgrowth of HIV-1 from resting cells in absence of cellular activation (MARCELLO, 2006; LEHRMAN et al., 2005).

However, global immune activation therapy or specific activation of provirus gene expression or similar therapy strategies greatly benefits from the concurrent removal of proviral DNA, thereby reducing in the patient the pool of infected cells.

The present invention also provides a method of treatment and/or prevention of a retrovirus infection, in particular, a HIV infection, in a subject. In one embodiment, the sequence of the retrovirus infecting the subject is analyzed in a sample obtained from the subject, and at least one expression vector encoding a tailored recombinase, at least one tailored recombinase or at least one cell transformed with said expression vector, e.g., one adult stem cell, is to be administered to the subject, if the proviral DNA from the subject comprises the asymmetric target sequence identified in step (a) on which the recombinase has been selected. The sample obtained from the subject may be a blood sample, e.g., comprising infected CD4+ cells.

BRIEF DESCRIPTION OF THE FIGURES

FIG. 1: FIG. 1 provides the target sites of specific recombinases, loxP (recognized by Cre), loxH (recognized by Fre), rox (recognized by Dre), zox (recognized by Zre), and loxLTR (recognized by Tre) (SEQ ID NO:3-7), as well as the asymmetric target sites present in a plurality of HIV-1 strains (SEQ ID NO:1 and 2). The spacer sequence is presented in bold. Nucleotide positions in the left half-site and right half-site of SEQ ID NO:1 or SEQ ID NO:2 that are not homologous to one of the known target sites are underlined. SEQ ID NO:1 has 54% homology to a pool of known recombinase target sites; SEQ ID NO:2 has 42% homology to a pool of known recombinase target sites.

FIG. 2: FIG. 2 provides the sequences of the subsites used for generation of the tailored recombinases TRE 3.0 and TRE 4.0. Nucleotide positions in the left half-site and right half-site of SEQ ID NO:1 or 2 that are not homologous to one of the known target sites are underlined. Subsite 1 and 2 are generated in step (d) of the method of the invention, and subsites 1A-C and subsites 2A-C are generated in step (e) of the method of the invention. Subsites 1a/b and subsites 2a/b as well intermediate subsites 1b+1, 1b+2, 2a+1 and 2a+2 are generated in further steps of the method of the invention.

FIG. 3 provides an outline of the evolution strategy and shows the results of the first evolution steps for SEQ ID NO:1. The starting library of recombinases was generated by pooling and family shuffling Cre and several known Cre-like recombinases (A). Successful recombinases were enriched by performing several rounds of substrate-linked protein evolution on the subsites of the 2nd subset. In (B) the recombination activity after the 1st evolution cycle is assayed, in (E) after the 6th evolution cycle. The recombined product is shorter, as the sequence between the target sites has been excised, which is marked with one triangle. Non-recombined product is marked with two triangles. Successful recombinases were amplified by PCR, resulting in a 1.7-kb product (C and D). One of the mismatches in the subsites 1C and 2C, respectively, was approached separately (via a mutated loxP target site, named ΔloxP in order to gain higher residual recombination activity on the subsites 1C and 2C (D).

FIG. 4 provides an outline of the further steps of the evolution strategy and shows the results of the final evolution steps for SEQ ID NO:1. Part (A) of the figure corresponds to the steps of the first evolution cycles described in detail in FIG. 3.

Figure 3:
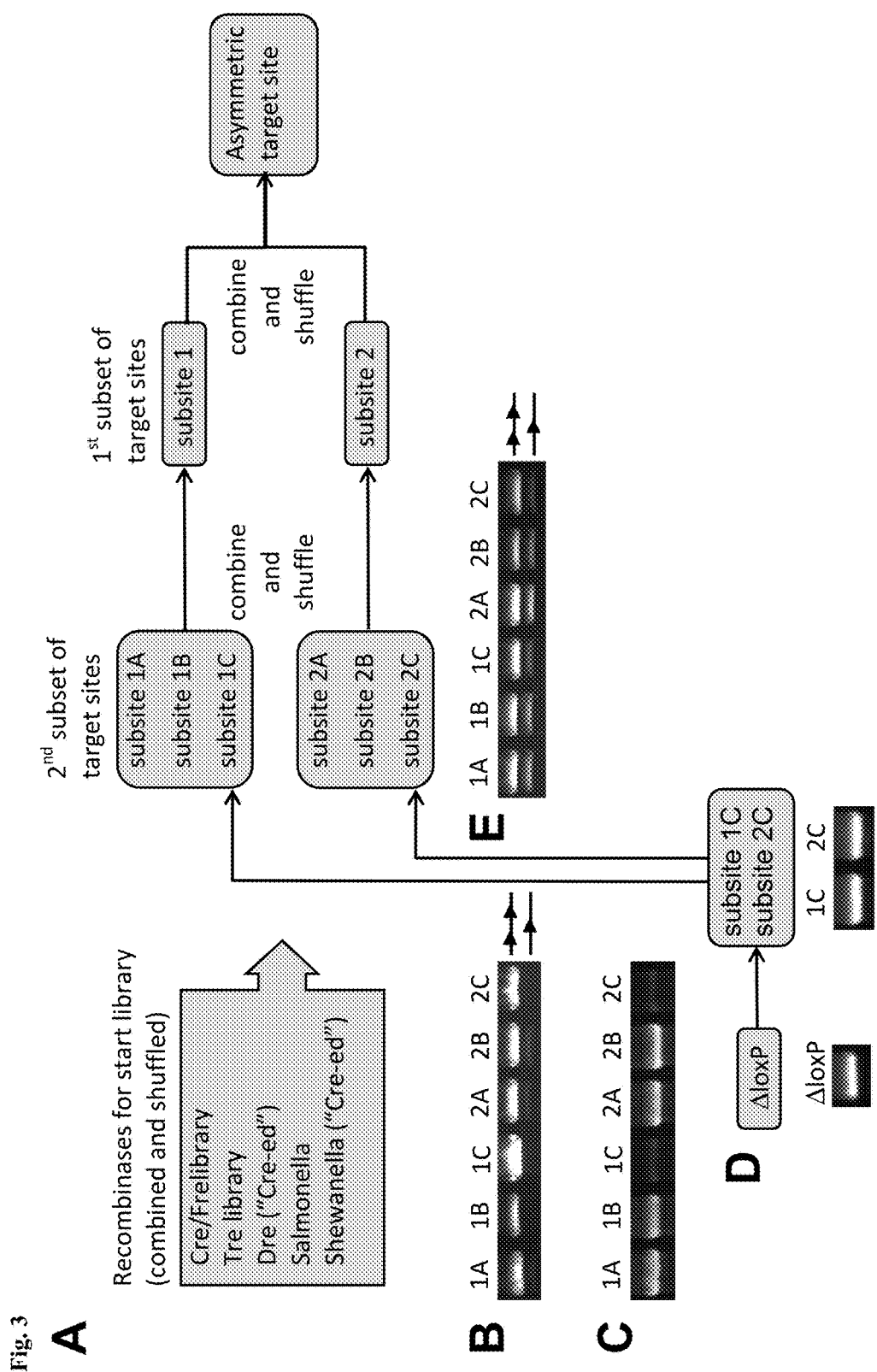
FIG. 3.
Figure 4:
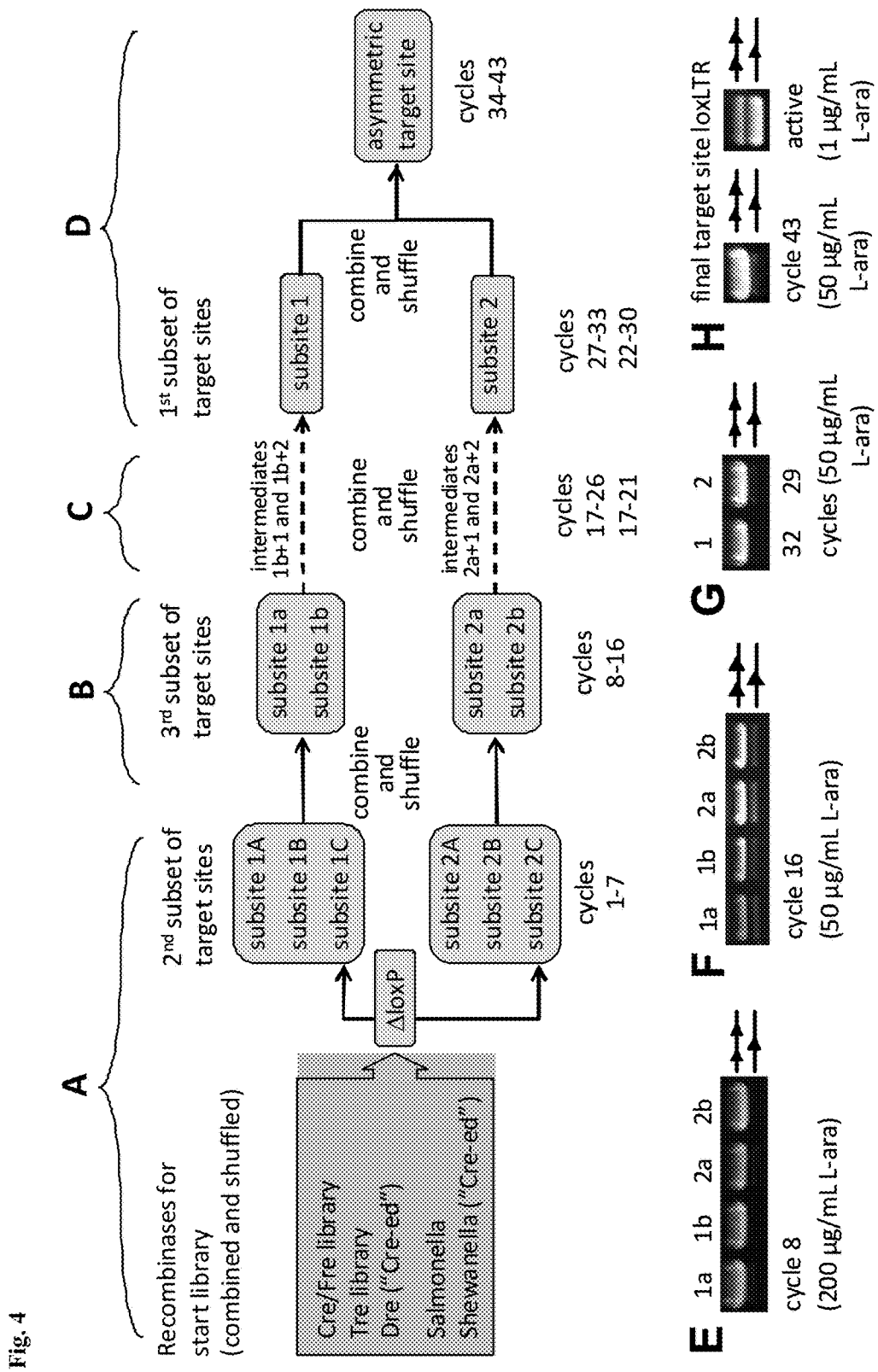
FIG. 4.

(B) Successful recombinases were furthermore enriched by performing several rounds of substrate-linked protein evolution on the subsites of the 3rd subset, followed by several rounds of substrate-linked evolution cycles on some intermediate substrates (C) and finally on the $1^{st}$ subsites (D) in order to get recombinases specific for the asymmetric target site SEQ ID NO:1. In (E) the recombination activity after the $8^{th}$ evolution cycle with relatively high amounts of transcription activator L-arabinose (L-ara; 200 µg/ml) is assayed, in (F) recombination activity was measured after the $16^{th}$ evolution cycle with lower transcriptional induction at only 50 µg/ml L-ara. Recombined product is marked with one triangle, non-recombined with two triangles. (G) and (H) show the respective recombination activity after the indicated evolution cycles, the indicated L-ara concentrations and on the indicated subsites. After the final evolution cycle (cycle 43), the recombinase population with the highest activity was isolated and enriched, resulting in the active library. Single clones of recombinases were selected and were subjected to further analyses.

FIG. 5: FIG. 5 provides an alignment of the protein sequences of (a) Cre recombinase SEQ ID NO:36, (b) common consensus sequence SEQ ID NO:37 of Tre recombinases (specific for asymmetric target-sites within HIV-1 LTR) (c) mandatory/stringent consensus sequence SEQ ID NO:38 of Tre recombinases specific for SEQ ID NO:1 and (d) relaxed consensus sequence SEQ ID NO:39 (with an obligation of 95%) of Tre recombinases specific for SEQ ID NO:1. Bold letter patches indicate conserved amino acids, non specified positions are indicated with an X.

EXAMPLES

Example 1

Identifying Asymmetric Target Sequences Present in a Plurality of Strains

The asymmetric target sequences were identified by a method divided in 3 steps: generation of a position weight matrix based on known recognition sites of a recombinase, provision of genomic sequences that are to be searched for recognition sites, and a binary search for potential target sites in the provided sequences and scoring of the resulting hits based on the initial position weight matrix, wherein the nucleotides are transformed into binary space.

SEQ ID NO:1 was found to be present in 348 of 379 HIV-1 strains of subtype B. Furthermore, SEQ ID NO:1 was found to be present in 32 of 40 HIV-1 strains of subtype A. It is located in the R region of the LTR.

SEQ ID NO:2 was found to be present in 288 of 379 HIV-1 strains of subtype B. SEQ ID NO:2 was not found to be present in any of the searched 40 HIV-1 strains of subtype A. It is located in the U3 region of the LTR.

Example 2

Generation of a Tailored Recombinase Recognising and Recombining an Asym-etric Target Sequence within the LTR of HIV-1

To start the evolution process, HIV-1 LTR sequences were selected which are highly conserved among HIV-1 strains. SEQ ID NO:1 and SEQ ID NO:2 were found to comply with these criteria and to represent asymmetric target sequences for which a tailored recombinase can be selected. In the following, the generation of a tailored recombinase recognizing SEQ ID NO:1 is described in detail.

A simplified outline of the evolution strategy and the progress made to date is outlined in FIG. 2. Overall, the evolution of a new Tre recombinase specifically recognizing the desired target sequence was conducted as disclosed in WO 2008/083931 and described by Sarkar et al. (Sarkar et al., Science 2007).

The start library of recombinases was generated by pooling and family shuffling Cre and several known Cre-like recombinases, namely a library of Cre mutants (Cre/Fre) (Buchholz & Stewart, Nature 2001), a previously generated Tre library (Sarkar et al., Science 2007), Dre (Sauer et al., Nucl Acids Res 2004), Zre (isolated from *Salmonella enterica*, Genbank accession number NZ_ABEW01000015), and Shew (*Shewanella* sp. strain ANA-3, Genbank accession number CP000470) (FIG. 2A). In order to promote the efficiency of family shuffling, Dre and Shew were modified ("Cre-ed") by changing the nucleotide sequence the way that it was as similar to Cre as possible without resulting in a changed protein sequence. To perform substrate-linked protein evolution, the start library of recombinases was cloned into the evolution vectors (Sarkar et al., Science 2007) containing the respective target subsite.

A first subset of two target nucleic acids comprising target sequences was generated, wherein the first target sequence is designated subsite 1 and comprises SEQ ID NO:8, and wherein the second target sequence is designated subsite 2 and comprises SEQ ID NO:12.

A second subset of target nucleic acids comprising modified target sequences was then generated on the basis of subsites 1 and 2. As shown in FIG. 2, they comprise SEQ ID NO:9-11 and 13-15, respectively. Highlighted in gray are the mismatches of the sequences in reference to the pool of the known target sequences recognized by the recombinases contained in the start library. The subsite libraries were independently grown in *E. coli*. At the first few evolution cycles (1-4) recombinase expression was induced with 200 μg/mL L-arabinose, at the following cycles with 100 μg/mL (cycles 5-6). Cultures were grown for 13 hours at 37° C., shaking. To assay recombination activity, the plasmid DNA isolated from the cultures was digested with BsrGI and XbaI. The digest of recombined plasmid DNA results in a shorter fragment than that of non-recombined plasmid (Sarkar et al., Science 2007). After the first evolution cycle, none or very weak bands of recombined product could be monitored for all the subsite libraries 1A, 1B, 1C, 2A, 2B, and 2C (FIG. 3B). To isolate successful recombinases, the plasmid DNA was digested with NdeI and amplified by PCR before cloning them back into the respective evolution vectors for the next evolution cycle (Sarkar et al., Science 2007). After the first evolution cycle, sufficient residual activity was obtained for subsite libraries 1A, 1B, 2A, and 2B, but not for subsite libraries 1C and 2C (FIG. 3C). It was found out that the mismatch in position 11 of the 34-bp target sequence was most critical for recombination activity. Hence, a modified loxP site was generated, named ΔloxP, containing only this single mutation (T) and the respective inverted repeat in position 24 (A). When testing the start library of recombinases in the evolution vector containing the ΔloxP target site, sufficient residual activity was obtained (FIG. 3D). The amplified library of successful recombinases were cloned back into the evolution vectors with the subsites 1C and 2C, respectively, and tested for recombination activity. Now, sufficient residual activity was also obtained for subsite libraries 1C and 2C (FIG. 3D), so that the evolution process on all the subsites could be started. 6 evolution cycles were performed on each of the subsites 1A, 1B, 1C, 2A, 2B, and 2C, significantly enriching the libraries of successful recombinases, as can be seen in the test gel shown in FIG. 3E (compare to FIG. 3B).

The enriched subsite libraries are combined and shuffled to obtain the libraries for continuing the evolution cycling process on the $2^{nd}$ subset of target sequences, namely subsite 1 and subsite 2. The libraries of successful recombinases are then enriched as described above before combining and shuffling them for the final stage of evolution cycling that is the evolution on the target site to be specifically recognized by the Tre recombinase. The nucleic acid encoding the recombinase may be obtained from the library; and cloned into an expression vector.

Materials and methods are used as described in WO 2008/083931 and BUCHHOLZ & STEWART, 2001, if not specified otherwise.

The obtained TRE recombinases adapted to recognize and recombine the asymmetric target sequences SEQ ID NO:1 and SEQ ID NO:2 are sequenced and their ability to recombine proviral DNA of different HIV-1 target strains confirmed.

REFERENCE LIST

Abremski K, Hoess R H, Sternberg N (1983) "Studies on the properties of P1 site-specific recombination: evidence for topologically unlinked products following recombination." *Cell* 32, 1301-1311.

Abremski K, Hoess R (1983) "Bacteriophage P1 site-specific recombination. Purification and properties of the Cre recombinase protein." *J. Biol. Chem.* 259, 1509-1514.

Adachi A, Gendelman H E, Koenig S, Folks T, Willey R, Rabson A, Martin M A (1986) "Production of acquired immunodeficiency syndrome-associated retrovirus in human and nonhuman cells transfected with an infectious molecular clone." *J. Virol.* 59, 284-291.

Alper H, Fischer C, Nevoigt E, Stephanopoulos G (2006) "Tuning genetic control through promoter engineering" *Proc. Natl. Acad. Sci. USA* 102, 12678-12683.

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. Nucleic acids research, 25, 3389-3402.

Beyer W R, Westphal M, Ostertag W, von Laer D (2002) "Oncoretrovirus and lentivirus vectors pseudotyped with lymphocytic choriomeningitis virus glycoprotein: generation, concentration and broad host range." *J. Virol.* 76, 1488-1495.

Blackard J T, Renjifo B R, Mwakagile D, Montano M A, Fawzi W W, Essex M (1999) "Transmission of human immunodeficiency type 1 viruses with intersubtype recombinant long terminal repeat sequences." *Virology* 254, 220-225.

Bloom J D, Meyer M M, Meinhold P, Otey C R, MacMillan D, Arnold F H (2005) "Evolving strategies for enzyme engineering." *Curr. Opin. Struct. Biol.* 15, 447-452.

Buchholz F, Ringrose L, Angrand P O, Rossi F, Stewart A F (1996) "Different thermostabilities of FLP and Cre recombinases: implications for applied site-specific recombination." *Nucl. Acids Res.* 24, 4256-4262.

Buchholz F, Angrand P O, Stewart A F (1998) "Improved properties of FLP recombinase evolved by cycling mutagenesis." *Nat. Biotechnol.* 16, 657-662.

Buchholz F, Stewart A F (2001) "Alteration of Cre recombinase site specificity by substrate-linked protein evolution." *Nat. Biotechnol.* 19, 1047-1052.

Chiu Y L, Soros V B, Kreisberg J F, Stopak K, Yonemoto W, Greene W C (2005) "Cellular APO-BEC3G restricts HIV-1 infection in resting CD4+ T cells." *Nature* 435, 108-114

Chun T-W, Engel D, Berrey M M, Shea T, Corey L, Fauci A S (1998) "Early establishment of a pool of latently infected, resting CD4+ T cells during primary HIV-1 infection." *Proc. Natl. Acad. Sci. USA* 95, 8869-8873.

Coates C J, Kaminski J M, Summers J B, Segal D J, Miller A D, Kolb A F (2005) "Site-directed genome modification: derivatives of DNA-modifying enzymes as targeting tools." *Trends Bio-technol.* 23, 407-419.

Collins C H, Yokobayashi Y, Umeno D, Arnold F H, (2003) "Engineering proteins that bind, move, make and break DNA." Curr. Opin. Biotechnol. 14, 665.

Combes P, Till R, Bee S, Smith M C (2002) "The *streptomyces* genome contains multiple pseudo-attB sites for the (phi)C31-encoded site-specific recombination system." *J. Bacteriol.* 184, 5746-5752.

Crameri A, Raillard S A, Bermudez E, Stemmer W P (1998) "DNA shuffling of a family of genes from diverse species accelerates directed evolution." *Nature* 391, 288-291.

Derossi D, Joliot A H, Chassaing G, Prochiantz A (1994) "The thrid helix of the Antennapedia homeodomain translocates through biological membranes." *J. Biol. Chem.* 269, 10444-10450.

Derossi D, Calvet S, Trembleau A, Chassaing G, Prochiantz A (1996) "Cell internalization of the third helix of the Antennapedia homeodomain is receptor-independent." *J Biol Chem* 271, 18188-18193.

Donovan, P. J., Gearhart, J. (2001) "The end of the beginning for pluripotent stem cells." *Nature* 414, 92-97.

Donzella G A, Schols D, Lin S W, Este J A, Nagashima K A, Maddon P J, Allaway G P, Sakmar T P, Henson G, De Clercq E, Moore J P (1998) "AMD3100, a small molecule inhibitor of HIV-1 entry via the CXCR4 co-receptor." *Nature Medicine* 4, 72-77.

Dybul M, Fauci A S, Bartlett J G, Kaplan J E, Pau A K (2002) "Guidelines for using antiretroviral agents among HIV-infected adults and adolescents." Annals of Internal Medicine 137, 381-433.

Eddy, S. R. (1998) Profile hidden Markov models. Bioinformatics (Oxford, England), 14, 755-763.

Edelman G M, Meech R, Owens G C, Jones F S (2000) "Synthetic promoter elements obtained by nucleotide sequence variation and selection for activity." *Proc. Natl. Acad. Sci. USA* 97, 3038-3043

Emerman M, Malim M H (1998) "HIV-1 regulatory/accessory genes: keys to unraveling viral and host cell biology." *Science* 280, 1880-1884.

Finzi D, Hemankova M, Pierson T, Carruth L M, Buck C, Chaisson R E, Quinn T C, Chadwick K, Margolick J, Brookmeyer R, Gallant J, Markowitz M, Ho D D, Richman D D, Siliciano R F (1997) "Identification of a reservoir for HIV-1 in patients on highly active antiretroviral therapy." *Science* 278, 1295-1300.

Flowers C C, Woffendin C, Petryniak J, Yang S, Nabel G J (1997) "Inhibition of recombinant human immunodeficiency virus type 1 replication by a site-specific recombinase." *J Virol.* 71, 2685-2692.

Gulick R M, Mellors J W, Havlir D, Eron J J, Gonzalez C, McMahon D, Richman D D, Valentine F T, Jonas L, Meibohm A, Emini E A, Chodakewitz J A (1997) "Treatment with indinavir, zidovudine, and lamivudine in adults with human immunodeficiency virus infection and prior antiretroviral therapy." *N. Engl. J. Med.* 337, 734-739.

Guzman L M, Belin D, Carson M J, Beckwith J (1995) "Tight regulation, modulation, and high-level expression by vectors containing the arabinose PBAD promoter." *J. Bacteriol.* 177, 4121-4130.

Hartenbach S, Fussenegger M (2006) "A novel synthetic mammalian promoter derived from an internal ribosome entry site." *Biotechnology and Bioengineering* 95, 547-559.

Hauber I, Bevec D, Heukeshoven J, Kratzer F, Horn F, Choidas A, Harrer T, Hauber J (2005) "Identification of cellular deoxyhypusine synthase as a novel target for antiretroviral therapy." *J. Clin. Invest.* 115, 76-85.

Hazuda D J, Young S D, Guare J P, Anthony N J, Gomez R P, Wai J S, Vacca J P, Handt L, Motzel S L, Klein H J, Dornadula G, Danovich R M, Witmer M V, Wilson K A, Tussey L, Schleif W A, Gabryelski L S, Jin L, Miller M D, Casimiro D R, Emini E A, Shiver J W (2004) "Integrase inhibitors and cellular immunity suppress retroviral replication in rhesus macaques." *Science* 305, 528-532.

Hoess R H, Abremski K (1985) "Mechanism of strand cleavage and exchange in the Cre-lox site-specific recombination system." *J. Mol. Biol.* 181, 351-362.

Johannes T W, Zhao H (2006) "Directed evolution of enzymes and biosynthetic pathways." *Curr. Opin. Microbiol.* 9, 261-267.

Krasnow M A, Cozzarelli N R (1983) "Site-specific relaxation and recombination by the Tn3 resolvase: Recognition of the DNA path between oriented res sites." *Cell* 32, 1313-1324.

Kulkosky J, Bray S (2006) "HAART-persistent HIV-1 latent reservoirs: their origin, mechanisms of stability and potential strategies for eradication." *Curr. HIV Res.* 4, 199-208.

Lalezari J P, Henry K, O'Hearn M, Montaner J S, Piliero P J, Trottier B, Walmsley S, Cohen C, Kuritzkes D R, Eron Jr. J J, Chung J, DeMasi R, Donatacci L, Drobnes C, Delehanty J, Salgo M (2003) "Enfuvirtide, an HIV-1 fusion inhibitor, for drug-resistant HIV infection in North and South America." *N. Engl. J. Med.* 348, 2175-2185.

Lee Y S, Park J S (1998) "A novel mutant loxP containing part of long terminal repeat of HIV-1 in spacer region: presentation of possible target site for antiviral strategy using site-specific recombinase." *Biochem. Biophys. Res. Comm.* 253, 588-593.

Lee Y S, Kim S T, Kim G W, Lee M, Park J S (2000) "An engineered lox sequence containing part of a long terminal repeat of HIV-1 permits Cre recombinase-mediated DNA excision." *Biochem. Cell Biol.* 78, 653-658.

Lehrman G, Hogue I B, Palmer S, Jennings C, Spina C A, Wiegand A, Landay A L, Coombs R W, Richman D D, Mellors J W, Coffin J M, Bosch R J, Margolis D M (2005) "Depletion of latent HIV-1 infection in vivo: a proof-of-concept study" *Lancet* 366, 549-555.

Lewandoski, M. (2001) "Conditional control of gene expression in the mouse." *Nat. Rev. Genet.* 2, 743-755.

Lin Q, Jo D, Gebre-Amlak K D, Ruley H E (2004) "Enhanced cell-permeant Cre protein for site-specific recombination in cultured cells." *BMC Biotechnol.* 4, 25.

Little S J, Holte S, Routy J P, Daar E S, Markowitz M, Collier A C, Koup R A, Mellors J W, Connick E, Conway B, Kilby M, Wang L, Whitcomb J M, Hellmann N S, Richman D D (2002) "Antiretroviral-drug resistance among patients recently infected with HIV." *N. Engl. J. Med.* 347, 385-394.

Macara I G (2001) "Transport into and out of the nucleus." *Microbiology and molecular biology reviews* 65, 570-594.

Malim M R, Hauber J, Fenrick R, Cullen B R (1988) "Immunodeficiency virus rev transactivator modulates the expression of the viral regulatory genes." *Nature* 335, 181-183.

Marcello A (2006) "Latency: the hidden HIV-1 challenge." Retrovirology 3, 7.

Matsumura I, Ellington A D (2001) "In vitro evolution of beta-glucuronidase into a beta-galactosidase proceeds through non-specific intermediates." J. Mol. Biol. 305, 331-339.

Minshull J, Stemmer W P. (1999) "Protein evolution by molecular breeding." Curr. Opin. Chem. Biol. 3, 284-290.

Nagy A (2000) "Cre recombinase: the universal reagent for genome tailoring." Genesis 26, 99-109.

Needleman S B, Wunsch C D (1970) "A general method applicable to the search for similarities in the amino acid sequence of two proteins." J. Mol. Biol. 48, 443-453.

Nolden L, Edenhofer F, Haupt S, Koch P, Wunderlich F T, Siemen H, Brustle O. (2006) "Site-specific recombination in human embryonic stem cells induced by cell-permeant Cre recombinase." Nat. Methods 3, 461-467.

O'Doherty U, Swiggard W J, Malim M H (2000) "Human immunodeficiency virus type 1 spinoculation enhances infection through virus binding." J. Virol. 74, 10074-10080.

Pearson W R, Lipman D J (1988) "Improved tools for biological sequence comparison." Proc Natl Acad Sci USA 85, 2444-2448.

Peitz M, Pfannkuche K, Rajewsky K, Edenhofer F. (2002) "Ability of the hydrophobic FGF and basic TAT peptides to promote cellular uptake of recombinant Cre recombinase: A tool for efficient genetic engineering of mammalian genomes." Proc. Natl. Acad. Sci. USA 99, 4489-4494.

Ratner L, Starcich B, Josephs S F, Hahn B H, Reddy E P, Livak K J, Petteway S R, Jr., Pearson M L, Haseltine W A, Arya S K, (1985) "Polymorphism of the 3' open reading frame of the virus associated with the acquired immune deficiency syndrome, human T-lymphotropic virus type III." Nucl. Acids Res. 13, 8219-8229.

Richard J P, Melikov K, Brooks H, Prevot P, Lebleu B, Chernomordik L V (2005) "Cellular uptake of the unconjugated TAT peptide involves clathrin-dependent endocytosis and heparin sulfate receptors." J. Biol. Chem. 280, 15300-15306.

Rüfer A W, Sauer B (2002) "Non-contact positions impose site selectivity on Cre recombinase." Nucl. Acids Res. 30, 2764-2771.

Ruhl M, Himmelspach M, Bahr G M, Hammerschmid F, Jaksche H, Wolff B, Aschauer H, Farrington G K, Probst H, Bevec D, Hauber J (1993) "Eukaryotic initiation factor 5A is a cellular target of the human immunodeficiency virus type 1 Rev activation domain mediating trans-activation" J. Cell Biol. 123, 1309-1320.

Sanger F, Nickler S, Coulson A R (1977) "DNA sequencing with chain-terminating inhibitors." Proc. Natl. Acad. Sci. USA 74, 5463-5467.

Santoro S W, Schultz P G (2002) "Directed evolution of the site specificity of Cre recombinase." Proc. Natl. Acad. Sci. USA 99, 4185-4190.

Saraf-Levy T, Santoro S W, Volpin H, Kushnirsky T, Eyal Y, Schultz P G, Gidoni D, Carmi N (2006) "Site-specific recombination of asymmetric/ox sites mediated by a heterotetrameric Cre recombinase complex." Bioorg. Med. Chem. 14, 3081-3089.

Sauer B, McDermott J (2004) "DNA recombination with a heterospecific Cre homolog identified from comparison of the pac-c1 regions of P1-related phages." Nucl. Acids. Res. 32, 6086-6095.

Schambach A, Bohne J, Chandra S, Will E, Margison G P, Williams D A, Baum C (2006) "Equal potency of gammaretroviral and lentiviral SIN vectors for expression of $O^6$-methylguanine-DNA methyltransferase in hematoietic cells." Molecular Therapy 13, 391-400.

Scherr M, Eder M (2002) "Gene Transfer into Hematopoietic Stem Cells Using Lentiviral Vectors." Current Gene Therapy 2, 45-55.

Shehu-Xhilaga M, Tachedjian G, Crowe S M, Kedzierska K. (2005) "Antiretroviral compounds: mechanisms underlying failure of HAART to eradicate HIV-1." Curr. Med. Chem. 12, 1705-1719.

Shimshek D R, Kim J, Hubner M R, Spergel D J, Buchholz F, Casanova E, Stewart A F, Seeburg P H, Sprengel R (2002) "Codon-improved Cre recombinase (iCre) expression in the mouse." Genesis 32(1), 19-26.

Smith T f, Waterman M S (1981) "Overlapping genes and information theory." J. Theor. Biol. 91, 379-380.

Stark W M, Boocock M R, Sherratt D J (1992) "Catalysis by site-specific recombinases." Trends Genet. 8, 432-439.

Stemmer W P C (1994) "Rapid evolution of a protein in vitro by DNA shuffling." Nature 370, 389-391.

Sternberg N, Hamilton D (1981) "Bacteriophage P1 site-specific recombination. I. Recombination between loxP sites." J. Mol. Biol. 150, 467-486.

Van Duyne G D (2001) "A structural view of cre-loxp site-specific recombination." Annu. Rev. Biophys. Biomol. Struct. 30, 87-104.

Vives E, Brodin P, Lebleu B (1997) "A truncated HIV-1 Tat protein basic domain rapidly translocates through the plasma membrane and accumulates in the cell nucleus." J. Biol. Chem. 272, 16010-16017.

Vives E (2003) "Cellular uptake of the TAT peptide: an endocytosis mechanism following ionic interactions." J. Mol. Recognit. 16, 265-271.

Volkert F C, Broach J R (1986) "Site-specific recombination promotes plasmid amplification in yeast." Cell 46, 541-550.

Voziyanov Y, Konieczka J H, Stewart A F, Jayaram M (2003) "Stepwise manipulation of DNA specificity in Flp recombinase: progressively adapting Flp to individual and combinatorial mutations in its target site." J. Mol. Biol. 326, 65-76.

Yuan L, Kurek I, English J, Keenan R (2005) "Laboratory-directed protein evolution" Microbiol. Mol. Biol. Rev. 69, 373-92.

WO 2002/44409

WO 2008/083931

Fawell S, Seery J, Daikh Y, Moore C, Chen L L, Pepinsky B, Barsoum J., Tat-mediated delivery of heterologous proteins into cells, Proc Natl Acad Sci USA. 1994 Jan. 18; 91(2):664-8.

Elliott G, O'Hare P., Intercellular trafficking and protein delivery by a herpesvirus structural protein, Cell. 1997 Jan. 24; 88(2):223-33

Oess S, Hildt E., Novel cell permeable motif derived from the PreS2-domain of hepatitis-B virus surface antigens, Gene Ther. 2000 May; 7(9):750-8.

The invention claimed is:

1. An evolution vector comprising a nucleic acid selected from the group consisting of SEQ ID NOS: 1, 2, and 8-15, wherein the evolution vector further encodes a recombinase, and wherein expression of the recombinase is controlled by an inducible promoter.

2. The evolution vector of claim 1, comprising the nucleic acid of SEQ ID NO: 1.

3. The evolution vector of claim 1, comprising the nucleic acid of SEQ ID NO: 2.

4. The evolution vector of claim 1, wherein the evolution vector is a plasmid.

5. The evolution vector of claim 1, wherein the vector is capable of being recombined by a tailored recombinase comprising an amino acid sequence selected from the group consisting of SEQ ID NOS: 40-64.

6. The evolution vector of claim 1, wherein the recombinase is selected from the group comprising Cre, Tre, Dre, Zre and Shew.

7. The evolution vector of claim 1, wherein the recombinase is a randomly mutated recombinase.

* * * * *

UNITED STATES PATENT AND TRADEMARK OFFICE
CERTIFICATE OF CORRECTION

PATENT NO. : 10,316,301 B2
APPLICATION NO. : 15/348077
DATED : June 11, 2019
INVENTOR(S) : Joachim Hauber et al.

Page 1 of 1

It is certified that error appears in the above-identified patent and that said Letters Patent is hereby corrected as shown below:

On the Title Page

Item (30) Foreign Application Priority Data:
"10005499" should read --10005499.8--.

Column 2, Item (56) Foreign Patent Document WO 2016/034553 A1:
"6/2013" should read --3/2016--.

Signed and Sealed this
Sixth Day of August, 2019

Andrei Iancu
*Director of the United States Patent and Trademark Office*

SEQUENCE LISTING

<160> NUMBER OF SEQ ID NOS: 65

<210> SEQ ID NO 1
<211> LENGTH: 34
<212> TYPE: DNA
<213> ORGANISM: Human immunodeficiency virus type 1

<400> SEQUENCE: 1
aacccactgc ttaagcctca ataaagcttg cctt                              34

<210> SEQ ID NO 2
<211> LENGTH: 34
<212> TYPE: DNA
<213> ORGANISM: Human immunodeficiency virus type 1

<400> SEQUENCE: 2
ctgggcggga ctggggagtg gcgagccctc agat                              34

<210> SEQ ID NO 3
<211> LENGTH: 34
<212> TYPE: DNA
<213> ORGANISM: Artificial Sequence
<220> FEATURE:
<223> OTHER INFORMATION: loxP

<400> SEQUENCE: 3
ataacttcgt ataatgtatg ctatacgaag ttat                              34

<210> SEQ ID NO 4
<211> LENGTH: 34
<212> TYPE: DNA
<213> ORGANISM: Artificial Sequence
<220> FEATURE:
<223> OTHER INFORMATION: loxH

<400> SEQUENCE: 4
atatatacgt atatagacat atatacgtat atat                              34

<210> SEQ ID NO 5
<211> LENGTH: 34
<212> TYPE: DNA
<213> ORGANISM: Artificial Sequence
<220> FEATURE:
<223> OTHER INFORMATION: rox

<400> SEQUENCE: 5
ctaactttaa ataatgccaa ttatttaaag ttat                              34

<210> SEQ ID NO 6
<211> LENGTH: 34
<212> TYPE: DNA
<213> ORGANISM: Artificial Sequence
<220> FEATURE:
<223> OTHER INFORMATION: zox

<400> SEQUENCE: 6
ataacttcgt ataacacaca ttatgcgaag ttat                              34

<210> SEQ ID NO 7
<211> LENGTH: 34
<212> TYPE: DNA
<213> ORGANISM: Human immunodeficiency virus

<400> SEQUENCE: 7
acaacatcct attacaccct atatgccaac atgg                              34

<210> SEQ ID NO 8
<211> LENGTH: 34
<212> TYPE: DNA
<213> ORGANISM: Artificial Sequence
<220> FEATURE:
<223> OTHER INFORMATION: subsite 1

<400> SEQUENCE: 8
aacccactgc ttaagcctca ataagcagtg ggtt                                34

<210> SEQ ID NO 9
<211> LENGTH: 34
<212> TYPE: DNA
<213> ORGANISM: Artificial Sequence
<220> FEATURE:
<223> OTHER INFORMATION: subsite 1A

<400> SEQUENCE: 9
aacacattgt ataagcctca atatacaatg tgtt                                34

<210> SEQ ID NO 10
<211> LENGTH: 34
<212> TYPE: DNA
<213> ORGANISM: Artificial Sequence
<220> FEATURE:
<223> OTHER INFORMATION: subsite 1B

<400> SEQUENCE: 10
ataccactgt ataagcctca atatacagtg gtat                                34

<210> SEQ ID NO 11
<211> LENGTH: 34
<212> TYPE: DNA
<213> ORGANISM: Artificial Sequence
<220> FEATURE:
<223> OTHER INFORMATION: subsite 1C

<400> SEQUENCE: 11
ataacattgc ttaagcctca ataagcaatg ttat                                34

<210> SEQ ID NO 12
<211> LENGTH: 34
<212> TYPE: DNA
<213> ORGANISM: Artificial Sequence
<220> FEATURE:
<223> OTHER INFORMATION: subsite 2

<400> SEQUENCE: 12
aaggcaagct ttaagcctca ataaagcttg cctt                                34

<210> SEQ ID NO 13
<211> LENGTH: 34
<212> TYPE: DNA
<213> ORGANISM: Artificial Sequence
<220> FEATURE:
<223> OTHER INFORMATION: subsite 2A

<400> SEQUENCE: 13
aagactaggt ataagcctca atatacctag tctt                                34

<210> SEQ ID NO 14
<211> LENGTH: 34
<212> TYPE: DNA
<213> ORGANISM: Artificial Sequence
<220> FEATURE:

<223> OTHER INFORMATION: subsite 2B

<400> SEQUENCE: 14
atagcaaggt ataagcctca atataccttg ctat                                    34

<210> SEQ ID NO 15
<211> LENGTH: 34
<212> TYPE: DNA
<213> ORGANISM: Artificial Sequence
<220> FEATURE:
<223> OTHER INFORMATION: subsite 2C

<400> SEQUENCE: 15
ataactagct ttaagcctca ataaagctag ttat                                    34

<210> SEQ ID NO 16
<211> LENGTH: 34
<212> TYPE: DNA
<213> ORGANISM: Artificial Sequence
<220> FEATURE:
<223> OTHER INFORMATION: subsite 1

<400> SEQUENCE: 16
ctgggcggga ctggggagtg gcagtcccgc ccag                                    34

<210> SEQ ID NO 17
<211> LENGTH: 34
<212> TYPE: DNA
<213> ORGANISM: Artificial Sequence
<220> FEATURE:
<223> OTHER INFORMATION: subsite 1A

<400> SEQUENCE: 17
ctgacttcga ctagggagtg gtagtcgaag tcag                                    34

<210> SEQ ID NO 18
<211> LENGTH: 34
<212> TYPE: DNA
<213> ORGANISM: Artificial Sequence
<220> FEATURE:
<223> OTHER INFORMATION: subsite 1B

<400> SEQUENCE: 18
ataggttcga atggggagtg gcattcgaac ctat                                    34

<210> SEQ ID NO 19
<211> LENGTH: 34
<212> TYPE: DNA
<213> ORGANISM: Artificial Sequence
<220> FEATURE:
<223> OTHER INFORMATION: subsite 1C

<400> SEQUENCE: 19
ataaccggga atagggagtg gtattcccgg ttat                                    34

<210> SEQ ID NO 20
<211> LENGTH: 34
<212> TYPE: DNA
<213> ORGANISM: Artificial Sequence
<220> FEATURE:
<223> OTHER INFORMATION: subsite 2

<400> SEQUENCE: 20
atctgagggc tcggggagtg gcgagccctc agat                                    34

```
<210> SEQ ID NO 21
<211> LENGTH: 34
<212> TYPE: DNA
<213> ORGANISM: Artificial Sequence
<220> FEATURE:
<223> OTHER INFORMATION: subsite 2A

<400> SEQUENCE: 21
atctgttggc atggggagtg gcatgccaac agat                               34

<210> SEQ ID NO 22
<211> LENGTH: 34
<212> TYPE: DNA
<213> ORGANISM: Artificial Sequence
<220> FEATURE:
<223> OTHER INFORMATION: subsite 2B

<400> SEQUENCE: 22
atatgatggc ttagggagtg gtaagccatc atat                               34

<210> SEQ ID NO 23
<211> LENGTH: 34
<212> TYPE: DNA
<213> ORGANISM: Artificial Sequence
<220> FEATURE:
<223> OTHER INFORMATION: subsite 2C

<400> SEQUENCE: 23
atatgtgggc acagggagtg gtgtgcccac atat                               34

<210> SEQ ID NO 24
<211> LENGTH: 1029
<212> TYPE: DNA
<213> ORGANISM: Artificial Sequence
<220> FEATURE:
<223> OTHER INFORMATION: Dre Cre-ed

<400> SEQUENCE: 24
atgtccgaat taattatctc aggctcatcc gggggttttt tacggaacat cggtaaagag     60
tatcaggagg ctgccgagaa ctttatgcgc ttcatgaatg atcaggggc gtatgctccg     120 aatacccttga gagaccttcg gttggttttc cattcgtggg cgcgatggtg ccacgcgcgt   180
cagctggcat ggtttcccat atcacctgaa atggctcgcg agtattttct acagcttcat   240
gatgccgatc tggcatcaac aactatcgat aaacattacg ccatgctaaa catgctgctt   300
agtcattgcg ggctgccacc actaagtgac gacaaaagtg tttcactggc tatgcggcgg   360
atccgacgag aagccgcaac tgaaaaaggt gaacgtacag acaggctat accgctccga    420 tgggatgatc tcaaactgct tgatgtactc ttgtcaagga gcgaacgcct cgtggatcta    480
cgtaatcggg catttctgtt tgttgcttat aacaccctga tgcgtatgtc gaaatttct    540 aggatcaggg ttggagatct cgaccaaact ggcgacacag tgacactcca tattagccac    600
acgaaaacga taactaccgc cgcagggcta gataaggtac ttagccggcg acaactgct    660 gtgctcaatg actggcttga cgtttctggt ctacgtgaac atcctgatgc cgtcctgttt    720
cccccgatcc acagaagtaa taaggcgcga attaccacca ccccgctaac agctcccgcc   780
atggaaaaga ttttttcaga cgcttgggta ttgcttaaca aacgtgatgc tacccctaat    840
aaggggagat accggacctg gactggacac agtgcccgtg tcggagccgc gatagatatg    900
gccgaaaagc aagtttcaat ggtggagatc atgcaagaag gtacctggaa gaaaccagaa    960
actctcatgc gctatctccg tcgcgggggt gtttcagtag gggcaaattc gcgcctgatg   1020
``` gattcttaa                                                                    1029

<210> SEQ ID NO 25
<211> LENGTH: 1116
<212> TYPE: DNA
<213> ORGANISM: Artificial Sequence
<220> FEATURE:
<223> OTHER INFORMATION: Shewanella recombinase Cre-ed

<400> SEQUENCE: 25

```
atgtccttac tgaccacaaa caaccattcg gttgcattat cgtacggtga accgctagt      60
acgcttaacg acagcctgaa ggacagctac cagcgttcta ccgacgaact gcaggcgctg    120
ctgtctaaac cgctggcgca gctgaccgac gcggacaaac tgcgtatccg tgaaatcacc    180
caggcgaaac tgaaacactt cctggacaac ggtcaccgga cgcgtcgtgc gaatacctgg    240
agagcgctca tgtcccgttg ggcgaagttc gagtcatggt gcttgacgaa taacctgaca    300
ccgttacccg caacacctga agttgttgcc acttttattg aatattatca ggcgagctca    360
tatacaacac tctcgcaata tgcgtgggcg ataaactcgt tcatgttga gtgcgggctg     420
ctaagcccag ttagcagcaa aactgttcaa gacaaacaga cgagatccg aatagtaaag     480
cttgaatccg gtggtctagc tcaagaacag gctacaccgt ccgactcca tcatctccag     540
atgcttattg aaagctacgg agaaagcgaa cgcttgctgg ataaacgtaa tctggcatta    600
ttgaacattg cttatgagtc cctgttacgt gaatccgaac ttctcaggat caaggttgga    660
catctcaaaa gtactttcga aggggattac gtactcagtg ttccctatac gaaaacgaac    720
gatagcggcg aagaagaagt ggtgaatatt acccgctgg gatttaaact gatccagcga     780
tacattcagg cgctgggct aactaaagaa gactacctgt ttcagccgat cggaagaagt     840
aataaagtct cggtacaagc caagccgatg tcaactcgca ccgtggatcg ggttttcta    900
tgggctttg aatcgcttgg cattgacaga cactcggcct ggtctggaca cagtgcccgt     960
atcggagccg cgcaagattt gctcgccgca ggatattcaa tagcgcagat ccaggaaaat   1020
ggtcgctgga gagtccaat gatggtcttg aggtatggca aagacatcaa agctaaagaa    1080
agcgcaatgg cgaagatgct ggcagaacgc cgttag                              1116
```

<210> SEQ ID NO 26
<211> LENGTH: 1029
<212> TYPE: DNA
<213> ORGANISM: Salmonella enterica

<400> SEQUENCE: 26

```
atgaccaatt cgttaaccgt tcatcaaaat ttaccggcgt tacctgttga gtctgtcaac     60
gaagaggttc gtcgaaacct gaatgcgatg ttccgtgata agaggcgtt ttccgaacat    120
acctggaaaa tgctgatgtc agtttgccgt tcatgggctg aatggtgttc ggttaacggt    180
tatacctggt tcccggcaca cccggaaaat gtgcgtgact attactcgg attgcaagcg    240
cgcggactgg cggttaagtc gatagagcaa catattgctc aactgaacat gctgcataaa    300
cgatctggct tgccacgccc aagcgacagt atggccgtct cccttgttat cgccggata    360
cgaaaggaaa acgtggatgc cggcgagcgg gctaaacagg cgctagcatt tgagcgacgg    420
gattttcaaa cggtccgctc tctcctcata gaaagtgagc gtatcattga tattcgcaac    480
ctggcattcc tggggctggc atataacacc ctgttacgca tatctgaaat tacccgcatc    540
cgcgttaaag atatttcgcg taccgaaggt gggcgaatgc tgatccgcat ggacggaca    600
aaaacgcttg tcagcaccgc cggcatagag aaagcgctaa gccttgatat aacgtatctg    660
```

```
gtagaccgat ggatcacggc ctccggcgta ggagaagacc cggataatta cctgttctgc    720
cgcgtacgta aaaatggcgt agcagtccca tcatccacca gcaaactgac aacgcgatcg    780
ctggaacata tcttcgaggc agcacactac aaagtttatg gtgcaaaaga tgcatccggc    840
gaacgctatc tggcgtggtc aggacacagt gcccgtgtag gcgctgcgcg tgacatggcc    900
cgcgccggtg ttggcgtacc ggaaattatg caagctggtg gctggactaa cgtcgaaata    960
gttatgagct atatccgtaa tctggacagt gaaacaggcg ctatggtccg ccttctggag   1020
gaaacctaa                                                           1029
```

```
<210> SEQ ID NO 27
<211> LENGTH: 34
<212> TYPE: DNA
<213> ORGANISM: Artificial Sequence
<220> FEATURE:
<223> OTHER INFORMATION: Subsite 1b+2

<400> SEQUENCE: 27
aacacactgc ttaagcctca ataagcagtg tgtt                                 34

<210> SEQ ID NO 28
<211> LENGTH: 34
<212> TYPE: DNA
<213> ORGANISM: Artificial Sequence
<220> FEATURE:
<223> OTHER INFORMATION: Subsite 1b+1

<400> SEQUENCE: 28
atcacactgc ttaagcctca ataagcagtg tgat                                 34

<210> SEQ ID NO 29
<211> LENGTH: 34
<212> TYPE: DNA
<213> ORGANISM: Artificial Sequence
<220> FEATURE:
<223> OTHER INFORMATION: Subsite 1b

<400> SEQUENCE: 29
ataacactgc ttaagcctca ataagcagtg ttat                                 34

<210> SEQ ID NO 30
<211> LENGTH: 34
<212> TYPE: DNA
<213> ORGANISM: Artificial Sequence
<220> FEATURE:
<223> OTHER INFORMATION: Subsite 1a

<400> SEQUENCE: 30
aacccattgt ataagcctca atatacaatg ggtt                                 34

<210> SEQ ID NO 31
<211> LENGTH: 34
<212> TYPE: DNA
<213> ORGANISM: Artificial Sequence
<220> FEATURE:
<223> OTHER INFORMATION: Subsite 2a+2

<400> SEQUENCE: 31
aaggcaaggt ttaagcctca ataaaccttg cctt                                 34

<210> SEQ ID NO 32
<211> LENGTH: 34
<212> TYPE: DNA
```

```
<213> ORGANISM: Artificial Sequence
<220> FEATURE:
<223> OTHER INFORMATION: Subsite 2a+1

<400> SEQUENCE: 32
aaggctaggt ttaagcctca ataaacctag cctt                                    34

<210> SEQ ID NO 33
<211> LENGTH: 34
<212> TYPE: DNA
<213> ORGANISM: Artificial Sequence
<220> FEATURE:
<223> OTHER INFORMATION: Subsite 2a

<400> SEQUENCE: 33
aaggctaggt ataagcctca atatacctag cctt                                    34

<210> SEQ ID NO 34
<211> LENGTH: 34
<212> TYPE: DNA
<213> ORGANISM: Artificial Sequence
<220> FEATURE:
<223> OTHER INFORMATION: Subsite 2b

<400> SEQUENCE: 34
ataacaagct ttaagcctca ataaagcttg ttat                                    34

<210> SEQ ID NO 35
<211> LENGTH: 34
<212> TYPE: DNA
<213> ORGANISM: Artificial Sequence
<220> FEATURE:
<223> OTHER INFORMATION: delta loxP

<400> SEQUENCE: 35
ataacttcgt ttaatgtatg ctaaacgaag ttat                                    34

<210> SEQ ID NO 36
<211> LENGTH: 343
<212> TYPE: PRT
<213> ORGANISM: Bacteriophage P1

<400> SEQUENCE: 36
```

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 37
<211> LENGTH: 343
<212> TYPE: PRT
<213> ORGANISM: Artificial Sequence
<220> FEATURE:
<223> OTHER INFORMATION: Tre common consensus sequence 100%
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (22)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:

```
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
```

```
-continued

<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (110)..(112)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (142)..(147)
<223> OTHER INFORMATION: Xaa can be any naturally occurring amino acid
<220> FEATURE:
<221> NAME/KEY: misc_feature
<222> LOCATION: (149)..(151)
<223> OTHER INFORMATION: Xaa can be any naturally occurring amino acid
<220> FEATURE:
<221> NAME/KEY: misc_feature
<222> LOCATION: (153)..(156)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (174)..(175)
<223> OTHER INFORMATION: Xaa can be any naturally occurring amino acid
<220> FEATURE:
<221> NAME/KEY: misc_feature
<222> LOCATION: (177)..(180)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(189)
```

-continued

```
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (197)..(199)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(236)
<223> OTHER INFORMATION: Xaa can be any naturally occurring amino acid
<220> FEATURE:
<221> NAME/KEY: misc_feature
<222> LOCATION: (241)..(245)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(255)
<223> OTHER INFORMATION: Xaa can be any naturally occurring amino acid
<220> FEATURE:
<221> NAME/KEY: misc_feature
<222> LOCATION: (258)..(260)
<223> OTHER INFORMATION: Xaa can be any naturally occurring amino acid
<220> FEATURE:
<221> NAME/KEY: misc_feature
<222> LOCATION: (262)..(263)
<223> OTHER INFORMATION: Xaa can be any naturally occurring amino acid
<220> FEATURE:
<221> NAME/KEY: misc_feature
<222> LOCATION: (266)..(268)
<223> OTHER INFORMATION: Xaa can be any naturally occurring amino acid
<220> FEATURE:
<221> NAME/KEY: misc_feature
<222> LOCATION: (270)..(273)
<223> OTHER INFORMATION: Xaa can be any naturally occurring amino acid
<220> FEATURE:
<221> NAME/KEY: misc_feature
<222> LOCATION: (277)..(278)
<223> OTHER INFORMATION: Xaa can be any naturally occurring amino acid
<220> FEATURE:
<221> NAME/KEY: misc_feature
```

-continued

```
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (319)..(320)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (341)..(343)
<223> OTHER INFORMATION: Xaa can be any naturally occurring amino acid

<400> SEQUENCE: 37

Met Ser Xaa Xaa Xaa Thr Xaa Xaa Xaa Leu Xaa Ala Leu Xaa Xaa
1               5                   10                  15

Asp Xaa Xaa Ser Asp Xaa Xaa Xaa Xaa Leu Xaa Xaa Xaa Xaa Arg
            20                  25                  30

Asp Xaa Xaa Ala Xaa Ser Xaa Xaa Thr Trp Xaa Xaa Leu Leu Ser Xaa
        35                  40                  45

Cys Arg Xaa Trp Xaa Ala Trp Cys Xaa Xaa Xaa Xaa Arg Xaa Xaa Phe
    50                  55                  60

Pro Xaa Xaa Pro Xaa Xaa Val Arg Xaa Tyr Leu Xaa Leu Gln Xaa
65                  70                  75                  80

Arg Gly Leu Xaa Val Xaa Thr Xaa Gln Gln His Leu Xaa Xaa Leu Asn
                85                  90                  95

Met Xaa His Arg Arg Xaa Gly Leu Xaa Arg Xaa Xaa Asp Xaa Xaa Xaa
        100                 105                 110

Val Ser Leu Xaa Xaa Arg Arg Ile Arg Xaa Glu Asn Val Asp Ala Gly
            115                 120                 125

Glu Arg Xaa Lys Gln Ala Leu Ala Phe Xaa Arg Xaa Asp Xaa Xaa Xaa
130                 135                 140

Xaa Xaa Xaa Leu Xaa Xaa Xaa Ser Xaa Xaa Xaa Xaa Asp Xaa Arg Xaa
145                 150                 155                 160

Leu Ala Xaa Leu Gly Xaa Ala Tyr Asn Thr Leu Leu Arg Xaa Xaa Glu
                165                 170                 175

Xaa Xaa Xaa Xaa Arg Xaa Xaa Asp Xaa Ser Xaa Thr Xaa Gly Gly Arg
            180                 185                 190

Xaa Leu Ile His Xaa Xaa Xaa Thr Lys Thr Leu Val Ser Thr Xaa Gly
        195                 200                 205

Val Glu Lys Ala Leu Ser Leu Xaa Xaa Thr Xaa Leu Xaa Glu Arg Trp
    210                 215                 220

Xaa Ser Xaa Ser Gly Val Ala Xaa Xaa Xaa Xaa Tyr Leu Phe Cys
225                 230                 235                 240

Xaa Xaa Xaa Xaa Xaa Gly Xaa Ala Xaa Pro Xaa Ala Xaa Xaa Xaa Leu
```

```
                    245                 250                 255
Ser Xaa Xaa Xaa Leu Xaa Xaa Ile Phe Xaa Xaa Xaa His Xaa Xaa Xaa
            260                 265                 270

Xaa Gly Ala Lys Xaa Xaa Ser Gly Xaa Arg Tyr Xaa Xaa Trp Ser Gly
        275                 280                 285

His Ser Ala Arg Val Gly Ala Ala Arg Asp Met Ala Arg Ala Gly Val
    290                 295                 300

Xaa Ile Xaa Glu Ile Met Gln Ala Gly Gly Trp Xaa Thr Val Xaa Xaa
305                 310                 315                 320

Val Met Asn Tyr Ile Arg Asn Leu Asp Ser Glu Xaa Gly Ala Met Val
                325                 330                 335

Arg Leu Leu Glu Xaa Xaa Xaa
            340

<210> SEQ ID NO 38
<211> LENGTH: 343
<212> TYPE: PRT
<213> ORGANISM: Artificial Sequence
<220> FEATURE:
<223> OTHER INFORMATION: Tre 3.0 consensus sequence 100%
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (22)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
```

```
<220> FEATURE:
<221> NAME/KEY: misc_feature
<222> LOCATION: (57)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(140)
```

```
<223> OTHER INFORMATION: Xaa can be any naturally occurring amino acid
<220> FEATURE:
<221> NAME/KEY: misc_feature
<222> LOCATION: (142)..(147)
<223> OTHER INFORMATION: Xaa can be any naturally occurring amino acid
<220> FEATURE:
<221> NAME/KEY: misc_feature
<222> LOCATION: (149)..(151)
<223> OTHER INFORMATION: Xaa can be any naturally occurring amino acid
<220> FEATURE:
<221> NAME/KEY: misc_feature
<222> LOCATION: (153)..(156)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (177)..(180)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (197)..(199)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
```

```
<222> LOCATION: (225)..(225)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(236)
<223> OTHER INFORMATION: Xaa can be any naturally occurring amino acid
<220> FEATURE:
<221> NAME/KEY: misc_feature
<222> LOCATION: (241)..(245)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(255)
<223> OTHER INFORMATION: Xaa can be any naturally occurring amino acid
<220> FEATURE:
<221> NAME/KEY: misc_feature
<222> LOCATION: (258)..(260)
<223> OTHER INFORMATION: Xaa can be any naturally occurring amino acid
<220> FEATURE:
<221> NAME/KEY: misc_feature
<222> LOCATION: (262)..(263)
<223> OTHER INFORMATION: Xaa can be any naturally occurring amino acid
<220> FEATURE:
<221> NAME/KEY: misc_feature
<222> LOCATION: (266)..(268)
<223> OTHER INFORMATION: Xaa can be any naturally occurring amino acid
<220> FEATURE:
<221> NAME/KEY: misc_feature
<222> LOCATION: (270)..(273)
<223> OTHER INFORMATION: Xaa can be any naturally occurring amino acid
<220> FEATURE:
<221> NAME/KEY: misc_feature
<222> LOCATION: (277)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (319)..(320)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (341)..(343)
<223> OTHER INFORMATION: Xaa can be any naturally occurring amino acid
```

<400> SEQUENCE: 38

Met Ser Xaa Xaa Xaa Thr Xaa Xaa Xaa Leu Ser Ala Leu Leu Xaa
1               5                   10                  15

Asp Xaa Xaa Ser Asp Xaa Xaa Xaa Xaa Leu Xaa Xaa Xaa Xaa Arg
            20                  25                  30

Asp Xaa Xaa Ala Xaa Ser Xaa Xaa Thr Trp Xaa Val Leu Leu Ser Xaa
        35                  40                  45

Cys Arg Xaa Trp Xaa Ala Trp Cys Xaa Xaa Xaa Arg Xaa Xaa Phe
50                  55                  60

Pro Xaa Xaa Pro Xaa Xaa Val Arg Xaa Tyr Leu Leu Xaa Leu Gln Xaa
65                  70                  75                  80

Arg Gly Leu Xaa Val Asn Thr Xaa Gln Gln His Leu Ala Xaa Leu Asn
                85                  90                  95

Met Xaa His Arg Arg Xaa Gly Leu Xaa Arg Xaa Xaa Asp Ser Xaa Xaa
        100                 105                 110

Val Ser Leu Xaa Xaa Arg Arg Ile Arg Xaa Glu Asn Val Asp Ala Gly
            115                 120                 125

Glu Arg Xaa Lys Gln Ala Leu Ala Phe Xaa Arg Xaa Asp Xaa Xaa Xaa
        130                 135                 140

Xaa Xaa Xaa Leu Xaa Xaa Xaa Ser Xaa Xaa Xaa Xaa Asp Xaa Arg Xaa
145                 150                 155                 160

Leu Ala Xaa Leu Gly Xaa Ala Tyr Asn Thr Leu Leu Arg Xaa Ser Glu
            165                 170                 175

Xaa Xaa Xaa Xaa Arg Xaa Xaa Asp Xaa Ser Xaa Thr Xaa Gly Gly Arg
        180                 185                 190

Xaa Leu Ile His Xaa Xaa Xaa Thr Lys Thr Leu Val Ser Thr Xaa Gly
        195                 200                 205

Val Glu Lys Ala Leu Ser Leu Xaa Xaa Thr Xaa Leu Xaa Glu Arg Trp
        210                 215                 220

Xaa Ser Xaa Ser Gly Val Ala Xaa Xaa Xaa Xaa Xaa Tyr Leu Phe Cys
225                 230                 235                 240

Xaa Xaa Xaa Xaa Xaa Gly Xaa Ala Xaa Pro Xaa Ala Xaa Xaa Xaa Leu
            245                 250                 255

Ser Xaa Xaa Xaa Leu Xaa Xaa Ile Phe Xaa Xaa Xaa His Xaa Xaa Xaa
        260                 265                 270

Xaa Gly Ala Lys Xaa Xaa Ser Gly Xaa Arg Tyr Xaa Xaa Trp Ser Gly
        275                 280                 285

His Ser Ala Arg Val Gly Ala Ala Arg Asp Met Ala Arg Ala Gly Val
        290                 295                 300

Xaa Ile Ala Glu Ile Met Gln Ala Gly Gly Trp Xaa Thr Val Xaa Xaa
305                 310                 315                 320

Val Met Asn Tyr Ile Arg Asn Leu Asp Ser Glu Xaa Gly Ala Met Val
            325                 330                 335

Arg Leu Leu Glu Xaa Xaa Xaa
            340

<210> SEQ ID NO 39
<211> LENGTH: 343
<212> TYPE: PRT
<213> ORGANISM: Artificial Sequence
<220> FEATURE:
<223> OTHER INFORMATION: Tre 3.0 consensus sequence 95%
<220> FEATURE:
<221> NAME/KEY: misc_feature
<222> LOCATION: (3)..(3)
<223> OTHER INFORMATION: Xaa can be any naturally occurring amino acid

```
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (117)..(117)
```

```
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (142)..(143)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
```

```
<222> LOCATION: (244)..(245)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (277)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (341)..(342)
<223> OTHER INFORMATION: Xaa can be any naturally occurring amino acid

<400> SEQUENCE: 39

Met Ser Xaa Leu Xaa Thr Xaa His Xaa Xaa Leu Ser Ala Leu Leu Xaa
1               5                   10                  15

Asp Xaa Thr Ser Asp Glu Xaa Arg Xaa Asn Leu Met Asp Val Xaa Arg
            20                  25                  30

Asp Xaa Xaa Ala Xaa Ser Glu His Thr Trp Lys Val Leu Leu Ser Val
        35                  40                  45

Cys Arg Xaa Trp Ala Ala Trp Cys Xaa Leu Asn Asn Arg Lys Xaa Phe
    50                  55                  60

Pro Ala Glu Pro Glu Asp Val Arg Asp Tyr Leu Leu Xaa Leu Gln Xaa
65                  70                  75                  80

Arg Gly Leu Ala Val Asn Thr Ile Gln Gln His Leu Ala Xaa Leu Asn
                85                  90                  95

Met Leu His Arg Arg Xaa Gly Leu Pro Arg Xaa Xaa Asp Ser Xaa Ala
            100                 105                 110

Val Ser Leu Val Xaa Arg Arg Ile Arg Xaa Glu Asn Val Asp Ala Gly
        115                 120                 125

Glu Arg Xaa Lys Gln Ala Leu Ala Phe Glu Arg Thr Asp Xaa Xaa Gln
    130                 135                 140

Val Arg Xaa Leu Met Xaa Ser Xaa Arg Xaa Gln Asp Ile Arg Xaa
145                 150                 155                 160

Leu Ala Xaa Leu Gly Xaa Ala Tyr Asn Thr Leu Leu Arg Ile Ser Glu
                165                 170                 175

Ile Ala Arg Ile Arg Xaa Xaa Asp Ile Ser Xaa Thr Xaa Gly Gly Arg
```

```
                    180                 185                 190
Met Leu Ile His Ile Xaa Arg Thr Lys Thr Leu Val Ser Thr Ala Gly
                195                 200                 205
Val Glu Lys Ala Leu Ser Leu Xaa Val Thr Xaa Leu Val Glu Arg Trp
            210                 215                 220
Ile Ser Xaa Ser Gly Val Ala Xaa Asp Pro Asn Asn Tyr Leu Phe Cys
225                 230                 235                 240
Xaa Val Arg Xaa Xaa Gly Val Ala Xaa Pro Ser Ala Thr Xaa Gln Leu
                245                 250                 255
Ser Thr Ser Ala Leu Gln Gly Ile Phe Xaa Ala Xaa His Xaa Leu Ile
            260                 265                 270
Tyr Gly Ala Lys Xaa Xaa Ser Gly Xaa Arg Tyr Leu Ala Trp Ser Gly
                275                 280                 285
His Ser Ala Arg Val Gly Ala Ala Arg Asp Met Ala Arg Ala Gly Val
            290                 295                 300
Xaa Ile Ala Glu Ile Met Gln Ala Gly Gly Trp Thr Thr Val Xaa Ser
305                 310                 315                 320
Val Met Asn Tyr Ile Arg Asn Leu Asp Ser Glu Thr Gly Ala Met Val
                325                 330                 335
Arg Leu Leu Glu Xaa Xaa Asp
            340

<210> SEQ ID NO 40
<211> LENGTH: 343
<212> TYPE: PRT
<213> ORGANISM: Artificial Sequence
<220> FEATURE:
<223> OTHER INFORMATION: Tre3-5

<400> SEQUENCE: 40

Met Ser Glu Leu Gln Thr Leu His Arg Asn Leu Ser Ala Leu Leu Val
1               5                   10                  15
Asp Ala Thr Ser Asp Glu Thr Arg Lys Asn Leu Met Asp Val Phe Arg
            20                  25                  30
Asp Arg Gln Ala Phe Ser Glu His Thr Trp Lys Val Leu Leu Ser Ile
        35                  40                  45
Cys Arg Ser Trp Ala Ala Trp Cys Lys Leu Asn Asp Arg Lys Trp Phe
    50                  55                  60
Pro Ala Glu Pro Glu Asp Val Arg Asp Tyr Leu Leu His Leu Gln Thr
65                  70                  75                  80
Arg Gly Leu Ala Val Asn Thr Ile Gln Gln His Leu Ala Gln Leu Asn
                85                  90                  95
Met Leu His Arg Arg Ser Gly Leu Pro Arg Leu Ser Asp Ser Asp Ala
            100                 105                 110
Val Ser Leu Val Met Arg Arg Ile Arg Arg Glu Asn Val Asp Ala Gly
        115                 120                 125
Glu Arg Ala Lys Gln Ala Leu Ala Phe Glu Arg Thr Asp Leu Asp Gln
    130                 135                 140
Val Arg Ser Leu Thr Glu Asp Ser Asp Arg Cys Arg Asp Ile Arg Asn
145                 150                 155                 160
Leu Ala Leu Leu Gly Val Ala Tyr Asn Thr Leu Leu Arg Ile Ser Glu
                165                 170                 175
Ile Ala Arg Val Arg Val Arg Asp Ile Ser Arg Thr Asp Gly Gly Arg
            180                 185                 190
Met Leu Ile His Ile Ser Arg Thr Lys Thr Leu Val Ser Thr Ala Gly
```

```
                195                 200                 205
Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 41
<211> LENGTH: 343
<212> TYPE: PRT
<213> ORGANISM: Artificial Sequence
<220> FEATURE:
<223> OTHER INFORMATION: Tre 3-18

<400> SEQUENCE: 41

Met Ser Asp Leu Gln Thr Leu His Arg Asn Leu Ser Ala Leu Leu Val
1               5                   10                  15

Asp Ala Thr Ser Asp Glu Ala Arg Lys Asn Leu Met Asp Val Leu Arg
            20                  25                  30

Asp Arg Gln Ala Tyr Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Thr
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Pro Gly Asp Ser Asp Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Ala Asp Phe Asp Gln
    130                 135                 140

Val Arg Ala Leu Ile Glu Asn Ser Asn Arg Cys Gln Asp Ile Arg Thr
145                 150                 155                 160

Leu Ala Phe Leu Gly Ile Ala Tyr Asn Thr Leu Leu Arg Ile Ser Glu
                165                 170                 175

Val Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
```

```
            210                 215                 220
Ile Ser Val Ser Gly Val Ala Gly Asp Pro Asn Asn Tyr Leu Phe Cys
225                 230                 235                 240

Gln Val Arg Arg Ser Gly Val Ala Val Pro Ser Ala Thr Ser Gln Leu
                245                 250                 255

Ser Thr Ser Ala Leu Gln Gly Ile Phe Glu Ala Thr His Arg Leu Ile
                260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
        290                 295                 300

Pro Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Ser Asp
            340

<210> SEQ ID NO 42
<211> LENGTH: 343
<212> TYPE: PRT
<213> ORGANISM: Artificial Sequence
<220> FEATURE:
<223> OTHER INFORMATION: Tre3-23

<400> SEQUENCE: 42

Met Ser Lys Leu Leu Thr Val His Gln Asn Leu Ser Ala Leu Leu Val
1               5                   10                  15

Asp Ala Thr Ser Asp Glu Thr Arg Lys Asn Leu Met Asp Val Leu Arg
                20                  25                  30

Asp Arg Gln Ala Phe Ser Glu His Thr Trp Lys Val Leu Leu Ser Val
            35                  40                  45

Cys Arg Ser Trp Ala Ala Trp Cys Asp Leu Asn Asn Arg Lys Arg Phe
        50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asn Ala
                100                 105                 110

Val Ser Leu Val Met Arg Arg Ile Arg Arg Glu Asn Val Asp Ala Gly
            115                 120                 125

Glu Arg Ala Lys Gln Ala Leu Ala Phe Glu Arg Thr Asp Leu Asp Gln
130                 135                 140

Val His Ser Leu Met Gly Asn Ser Asp Arg Gly Gln Asp Ile Arg Asn
145                 150                 155                 160

Leu Ala Leu Leu Gly Val Ala Tyr Asn Thr Leu Leu Arg Ile Ser Glu
                165                 170                 175

Ile Ala Arg Ile Arg Val Lys Asp Ile Ser Arg Thr Asp Gly Gly Arg
            180                 185                 190

Met Leu Ile His Ile Ser Arg Thr Lys Thr Leu Val Ser Thr Ala Gly
            195                 200                 205

Val Glu Lys Ala Leu Ser Leu Arg Val Thr Lys Leu Val Glu Arg Trp
210                 215                 220

Ile Ser Val Ser Gly Val Ala Asp Asp Pro Asn Asn Tyr Leu Phe Cys
```

```
225                 230                 235                 240
Pro Val Arg Ile Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
                260                 265                 270

Tyr Gly Ala Lys Gly Gly Ser Gly Gln Arg Tyr Leu Ala Trp Ser Gly
                275                 280                 285

His Ser Ala Arg Val Gly Ala Ala Arg Asp Met Ala Arg Ala Gly Val
                290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
                340

<210> SEQ ID NO 43
<211> LENGTH: 343
<212> TYPE: PRT
<213> ORGANISM: Artificial Sequence
<220> FEATURE:
<223> OTHER INFORMATION: Tre3-27

<400> SEQUENCE: 43

Met Ser Glu Leu Leu Thr Leu His Gln Asn Leu Ser Ala Leu Leu Val
1               5                   10                  15

Asp Ala Thr Ser Asp Glu Ala Arg Lys Asn Leu Met Asp Val Leu Arg
                20                  25                  30

Asp Arg Gln Ala Phe Ser Lys His Thr Trp Lys Val Leu Leu Ser Val
                35                  40                  45

Cys Arg Thr Trp Ala Ala Trp Cys Lys Leu Asn Asn Arg Lys Trp Phe
            50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
                100                 105                 110

Val Ser Leu Val Ile Arg Arg Ile Arg Arg Glu Asn Val Asp Ala Gly
            115                 120                 125

Glu Arg Ala Lys Gln Ala Leu Ala Phe Glu Arg Thr Asp Phe Asp Gln
                130                 135                 140

Val Arg Ala Leu Met Glu Asn Ser Asp Arg Gly Gln Asp Ile Arg Ser
145                 150                 155                 160

Leu Ala Phe Leu Gly Ile Ala Tyr Asn Thr Leu Leu Arg Ile Ser Glu
                165                 170                 175

Ile Ala Arg Ile Arg Val Arg Asp Ile Ser Arg Thr Asp Gly Gly Arg
                180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
                210                 215                 220

Ile Ser Val Ser Gly Val Ala Asp Asp Pro Asn Asn Tyr Leu Phe Cys
225                 230                 235                 240

Gln Val Arg Lys Asn Gly Val Ala Val Pro Ser Ala Thr Ser Gln Leu
```

```
                    245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Gln Ala Trp Ser Gly
        275                 280                 285

His Ser Ala Arg Val Gly Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 44
<211> LENGTH: 343
<212> TYPE: PRT
<213> ORGANISM: Artificial Sequence
<220> FEATURE:
<223> OTHER INFORMATION: Tre3-31

<400> SEQUENCE: 44

```
Met Ser Asp Leu Gln Thr Leu His Arg Asn Leu Ser Ala Leu Leu Val
1               5                   10                  15

Asp Ala Ser Ser Asp Glu Ala Arg Lys Asn Leu Met Asp Val Leu Arg
            20                  25                  30

Asp Arg Gln Ala Tyr Ser Glu His Thr Trp Lys Val Leu Leu Ser Val
        35                  40                  45

Cys Arg Thr Trp Ala Ala Trp Cys Lys Leu Asp Asn Arg Lys Trp Phe
    50                  55                  60

Pro Ala Glu Pro Glu Asp Val Arg Asp Tyr Leu Leu His Leu Gln Ala
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ala Leu Met Glu Asn Ser Asp Arg Gly Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Glu Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Ile Asn Gly Val Ala Val Pro Ser Ala Thr Ser Gln Leu
                245                 250                 255

Ser Thr Ser Ala Leu Gln Gly Ile Phe Glu Ala Ala His Arg Leu Ile
```

```
            260                 265                 270
His Gly Ala Lys Asp Gly Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Pro Ile Ala Glu Ile Met Gln Ala Gly Gly Trp Thr Thr Val Asp Asn
305                 310                 315                 320

Val Met Asn Tyr Ile Arg Asn Leu Asp Ser Glu Thr Gly Ala Met Val
                325                 330                 335

Arg Leu Leu Glu Asp Asp Asp
            340

<210> SEQ ID NO 45
<211> LENGTH: 343
<212> TYPE: PRT
<213> ORGANISM: Artificial Sequence
<220> FEATURE:
<223> OTHER INFORMATION: Tre3-37

<400> SEQUENCE: 45

Met Ser Glu Leu Leu Thr Val His Gln Asn Leu Ser Ala Leu Leu Val
1               5                   10                  15

Asp Ala Thr Ser Asp Glu Thr Cys Lys Asn Leu Met Asp Val Phe Arg
            20                  25                  30

Asp Arg Gln Ala Phe Ser Glu His Thr Trp Arg Val Leu Leu Ser Val
            35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
            115                 120                 125

Glu Arg Thr Lys Gln Ala Leu Ala Phe Glu Arg Thr Asp Phe Asp Gln
        130                 135                 140

Val Arg Ala Leu Met Glu Asn Ser Asp Arg Gly Gln Asp Ile Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Val Lys Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asn Asp Pro Asn Asn Tyr Leu Phe Cys
225                 230                 235                 240

Gln Val Arg Lys Ser Gly Val Ala Val Pro Ser Ala Thr Ser Arg Leu
                245                 250                 255

Ser Thr Ser Ala Leu Gln Gly Ile Phe Gly Ala Ala His Cys Leu Ile
            260                 265                 270

Tyr Gly Ala Lys Asp Gly Ser Gly Gln Arg Tyr Leu Ala Trp Ser Gly
```

```
            275                 280                 285
His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 46
<211> LENGTH: 343
<212> TYPE: PRT
<213> ORGANISM: Artificial Sequence
<220> FEATURE:
<223> OTHER INFORMATION: Tre3-43

<400> SEQUENCE: 46

Met Ser Glu Leu Gln Thr Leu His Gln Asn Leu Ser Ala Leu Leu Val
1               5                   10                  15

Asp Ala Thr Ser Asp Glu Thr Arg Lys Asn Leu Met Asp Val Leu Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Ser Asn Asn Arg Lys Trp Phe
    50                  55                  60

Pro Ala Asp Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Ala Arg Ala Leu Met Glu Asn Ser Asp Arg Gly Gln Asp Ile Arg Ser
145                 150                 155                 160

Leu Ala Phe Leu Gly Ile Ala Tyr Asn Thr Leu Leu Arg Ile Ser Glu
                165                 170                 175

Ile Ala Arg Ile Arg Val Lys Asp Ile Ser His Thr Asp Gly Gly Arg
            180                 185                 190

Met Leu Ile His Ile Ser Arg Thr Lys Thr Leu Val Ser Thr Thr Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Gln Val Arg Arg Asn Gly Val Ala Val Pro Ser Ala Thr Cys Gln Leu
                245                 250                 255

Ser Thr Ser Ala Leu Gln Gly Ile Phe Gly Ala Ala His Cys Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
```

```
                290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 47
<211> LENGTH: 343
<212> TYPE: PRT
<213> ORGANISM: Artificial Sequence
<220> FEATURE:
<223> OTHER INFORMATION: Tre3-46

<400> SEQUENCE: 47

Met Ser Asp Leu Gln Thr Val His Arg Asn Leu Ser Ala Leu Leu Val
1               5                   10                  15

Asp Ala Thr Ser Asp Glu Thr Arg Lys Asn Leu Met Asp Val Leu Arg
                20                  25                  30

Asp Arg Gln Ala Phe Ser Glu His Thr Trp Lys Val Leu Leu Ser Val
            35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asp Ser Asp Arg Gly Gln Asp Ile Arg Asn
145                 150                 155                 160

Leu Ala Leu Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Phe Val Ser Gly Val Ala Asn Asp Pro Asn Asn Tyr Leu Phe Cys
225                 230                 235                 240

Gln Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
```

```
                       305                 310                 315                 320

Val Met Asn Tyr Ile Arg Asn Leu Asp Ser Glu Thr Gly Ala Met Val
                       325                 330                 335

Arg Leu Leu Glu Asp Asp Asp
                340

<210> SEQ ID NO 48
<211> LENGTH: 343
<212> TYPE: PRT
<213> ORGANISM: Artificial Sequence
<220> FEATURE:
<223> OTHER INFORMATION: Tre3-48

<400> SEQUENCE: 48

Met Ser Lys Leu Gln Thr Val His Arg Asn Leu Ser Ala Leu Leu Val
1               5                   10                  15

Asp Ala Thr Ser Asp Glu Thr Arg Lys Asn Leu Met Asp Val Phe Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Leu Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Leu Asp Gln
    130                 135                 140

Val Arg Ala Leu Met Glu Asn Ser Asp Arg Cys Gln Asp Ile Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Lys Thr Lys Thr Leu Val Ser Thr Thr Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Pro Ile Ala Glu Ile Met Gln Ala Gly Gly Trp Thr Thr Val Glu Ser
305                 310                 315                 320

Val Met Asn Tyr Ile Arg Asn Leu Asp Ser Glu Ala Gly Ala Met Val
```

<210> SEQ ID NO 49
<211> LENGTH: 343
<212> TYPE: PRT
<213> ORGANISM: Artificial Sequence
<220> FEATURE:
<223> OTHER INFORMATION: Tre3-63

<400> SEQUENCE: 49

```
Met Ser Glu Leu Leu Thr Leu His Gln Asn Leu Ser Ala Leu Leu Val
1               5                   10                  15

Asp Ala Thr Ser Asp Glu Ala Arg Lys Asn Leu Met Asp Val Leu Arg
            20                  25                  30

Asp Arg Gln Ala Tyr Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Ala
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ala Leu Met Glu Asn Ser Asp Arg Gly Gln Asp Ile Arg Asn
145                 150                 155                 160

Leu Ala Leu Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Arg Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Ile Asn Gly Val Ala Val Pro Ser Ala Thr Ser Gln Leu
                245                 250                 255

Ser Thr Ser Ala Leu Gln Gly Ile Phe Glu Ala Ala His Arg Leu Ile
            260                 265                 270

Tyr Gly Ala Lys Gly Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 50
<211> LENGTH: 343
<212> TYPE: PRT
<213> ORGANISM: Artificial Sequence
<220> FEATURE:
<223> OTHER INFORMATION: Tre3-74

<400> SEQUENCE: 50

```
Met Ser Asp Leu Gln Thr Val His Arg Asn Leu Ser Ala Leu Leu Val
1               5                   10                  15

Asp Ala Thr Ser Asp Glu Thr Arg Arg Asn Leu Met Asp Val Phe Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asn Ala
            100                 105                 110

Val Ser Leu Val Met Arg Arg Ile Arg Arg Glu Asn Val Asp Ala Gly
        115                 120                 125

Glu Arg Ala Lys Gln Ala Leu Ala Phe Glu Arg Thr Asp Phe Asp Arg
    130                 135                 140

Val Arg Ala Leu Met Glu Asn Ser Asp Arg Cys Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Gln Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Arg Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Gly Asp Asp
            340
```

-continued

```
<210> SEQ ID NO 51
<211> LENGTH: 343
<212> TYPE: PRT
<213> ORGANISM: Artificial Sequence
<220> FEATURE:
<223> OTHER INFORMATION: Tre3-78

<400> SEQUENCE: 51
```

| | | | | | | | | | | | | | | |
|---|---|---|---|---|---|---|---|---|---|---|---|---|---|---|
| Met | Ser | Asp | Leu | Gln | Thr | Val | His | Arg | Asn | Leu | Ser | Ala | Leu | Leu | Ile |
| 1 | | | | 5 | | | | | 10 | | | | | 15 | |
| Asp | Ala | Thr | Ser | Asp | Glu | Thr | Arg | Lys | Asn | Leu | Met | Asp | Val | Phe | Arg |
| | | | 20 | | | | | 25 | | | | | 30 | | |
| Asp | Arg | Gln | Ala | Phe | Ser | Glu | His | Thr | Trp | Lys | Val | Leu | Leu | Ser | Val |
| | | 35 | | | | | 40 | | | | | 45 | | | |
| Cys | Arg | Thr | Trp | Ala | Ala | Trp | Cys | Lys | Leu | Asn | Asn | Arg | Lys | Trp | Phe |
| 50 | | | | | 55 | | | | | 60 | | | | | |
| Pro | Thr | Glu | Pro | Glu | Asp | Val | Arg | Asp | Tyr | Leu | Leu | His | Leu | Gln | Val |
| 65 | | | | | 70 | | | | 75 | | | | | 80 | |
| Arg | Gly | Leu | Ala | Val | Asn | Thr | Ile | Gln | Gln | His | Leu | Ala | Gln | Leu | Asn |
| | | | | 85 | | | | | 90 | | | | | 95 | |
| Met | Leu | His | Arg | Arg | Phe | Gly | Leu | Pro | Arg | Pro | Gly | Asp | Ser | Asp | Ala |
| | | | 100 | | | | | 105 | | | | | 110 | | |
| Val | Ser | Leu | Val | Ile | Arg | Arg | Ile | Arg | Arg | Glu | Asn | Val | Asp | Ala | Gly |
| | | 115 | | | | | 120 | | | | | 125 | | | |
| Glu | Arg | Thr | Lys | Gln | Ala | Leu | Ala | Phe | Glu | Arg | Thr | Asp | Phe | Asp | Gln |
| 130 | | | | | 135 | | | | | 140 | | | | | |
| Val | Arg | Ala | Leu | Met | Glu | Asn | Ser | Asp | Arg | Gly | Gln | Asp | Ile | Arg | Asn |
| 145 | | | | | 150 | | | | | 155 | | | | | 160 |
| Leu | Ala | Phe | Leu | Gly | Val | Ala | Tyr | Asn | Thr | Leu | Leu | Arg | Ile | Ser | Glu |
| | | | | 165 | | | | | 170 | | | | | 175 | |
| Ile | Ala | Arg | Ile | Arg | Val | Arg | Asp | Ile | Ser | Arg | Thr | Asp | Gly | Gly | Arg |
| | | | 180 | | | | | 185 | | | | | 190 | | |
| Met | Leu | Ile | His | Ile | Ser | Arg | Thr | Lys | Thr | Leu | Val | Ser | Thr | Ala | Gly |
| | | 195 | | | | | 200 | | | | | 205 | | | |
| Val | Glu | Lys | Ala | Leu | Ser | Leu | Gly | Ile | Thr | Lys | Leu | Val | Glu | Arg | Trp |
| 210 | | | | | 215 | | | | | 220 | | | | | |
| Ile | Ser | Val | Ser | Gly | Val | Ala | Asp | Asp | Pro | Asn | Asn | Tyr | Leu | Phe | Cys |
| 225 | | | | | 230 | | | | | 235 | | | | | 240 |
| Pro | Val | Arg | Ile | Asn | Gly | Val | Ala | Val | Pro | Ser | Ala | Thr | Ser | Gln | Leu |
| | | | | 245 | | | | | 250 | | | | | 255 | |
| Ser | Thr | Ser | Ala | Leu | Gln | Gly | Ile | Phe | Ala | Ala | Ala | His | Arg | Leu | Ile |
| | | | 260 | | | | | 265 | | | | | 270 | | |
| Tyr | Gly | Ala | Lys | Asp | Gly | Ser | Gly | Gln | Arg | Tyr | Leu | Ala | Trp | Ser | Gly |
| | | 275 | | | | | 280 | | | | | 285 | | | |
| His | Ser | Ala | Arg | Val | Gly | Ala | Ala | Arg | Asp | Met | Ala | Arg | Ala | Gly | Val |
| 290 | | | | | 295 | | | | | 300 | | | | | |
| Ser | Ile | Ala | Glu | Ile | Met | Gln | Ala | Gly | Gly | Trp | Thr | Thr | Val | Asp | Ser |
| 305 | | | | | 310 | | | | | 315 | | | | | 320 |
| Val | Met | Asn | Tyr | Ile | Arg | Asn | Leu | Asp | Ser | Glu | Thr | Gly | Ala | Met | Val |
| | | | | 325 | | | | | 330 | | | | | 335 | |
| Arg | Leu | Leu | Glu | Asp | Gly | Gly |
| | | | 340 | | | |

```
<210> SEQ ID NO 52
<211> LENGTH: 343
<212> TYPE: PRT
```

<213> ORGANISM: Artificial Sequence
<220> FEATURE:
<223> OTHER INFORMATION: Tre3-89

<400> SEQUENCE: 52

| | | | | | | | | | | | | | | |
|---|---|---|---|---|---|---|---|---|---|---|---|---|---|---|
| Met | Ser | Asp | Leu | Leu | Thr | Val | His | Arg | Asn | Leu | Ser | Ala | Leu | Leu | Val |
| 1 | | | | 5 | | | | | 10 | | | | | 15 | |
| Asp | Ala | Thr | Ser | Asp | Glu | Ala | Arg | Lys | Asn | Leu | Met | Asp | Val | Leu | Arg |
| | | | 20 | | | | | 25 | | | | | 30 | | |
| Asp | Arg | Gln | Ala | Tyr | Ser | Glu | His | Thr | Trp | Lys | Val | Leu | Leu | Ser | Val |
| | | | 35 | | | | | 40 | | | | | 45 | | |
| Cys | Arg | Thr | Trp | Ala | Ala | Trp | Cys | Lys | Leu | Asn | Asn | Arg | Lys | Trp | Phe |
| 50 | | | | | 55 | | | | | 60 | | | | | |
| Pro | Ala | Glu | Pro | Glu | Asp | Val | Arg | Asp | Tyr | Leu | Leu | His | Leu | Gln | Val |
| 65 | | | | | 70 | | | | | 75 | | | | | 80 |
| Arg | Gly | Leu | Ala | Val | Asn | Thr | Ile | Gln | Gln | His | Leu | Ala | Gln | Leu | Asn |
| | | | | 85 | | | | | 90 | | | | | 95 | |
| Met | Leu | His | Arg | Arg | Phe | Gly | Leu | Pro | Arg | Pro | Gly | Asp | Ser | Asn | Ala |
| | | | 100 | | | | | 105 | | | | | 110 | | |
| Val | Ser | Leu | Val | Met | Arg | Arg | Ile | Arg | Arg | Glu | Asn | Val | Asp | Ala | Gly |
| | | | 115 | | | | | 120 | | | | | 125 | | |
| Glu | Arg | Ala | Lys | Gln | Ala | Leu | Ala | Phe | Glu | Arg | Thr | Asp | Leu | Asp | Gln |
| | 130 | | | | | 135 | | | | | 140 | | | | |
| Val | Arg | Ser | Leu | Met | Glu | Asp | Ser | Asp | Arg | Cys | Gln | Asp | Ile | Arg | Ser |
| 145 | | | | | 150 | | | | | 155 | | | | | 160 |
| Leu | Ala | Phe | Leu | Gly | Val | Ala | Tyr | Asn | Thr | Leu | Leu | Arg | Ile | Ser | Glu |
| | | | | 165 | | | | | 170 | | | | | 175 | |
| Ile | Ala | Arg | Ile | Arg | Val | Lys | Asp | Ile | Ser | Arg | Thr | Asp | Gly | Gly | Arg |
| | | | 180 | | | | | 185 | | | | | 190 | | |
| Met | Leu | Ile | His | Ile | Ser | Arg | Thr | Lys | Thr | Leu | Val | Ser | Thr | Ala | Gly |
| | | | 195 | | | | | 200 | | | | | 205 | | |
| Val | Glu | Lys | Ala | Leu | Ser | Leu | Gly | Val | Thr | Lys | Leu | Val | Glu | Arg | Trp |
| | 210 | | | | | 215 | | | | | 220 | | | | |
| Ile | Ser | Val | Ser | Gly | Val | Ala | Asp | Asp | Pro | Asn | Asn | Tyr | Leu | Phe | Cys |
| 225 | | | | | 230 | | | | | 235 | | | | | 240 |
| Gln | Val | Arg | Arg | Asn | Gly | Val | Ala | Ala | Pro | Ser | Ala | Thr | Ser | Gln | Leu |
| | | | | 245 | | | | | 250 | | | | | 255 | |
| Ser | Thr | Ser | Ala | Leu | Gln | Gly | Ile | Phe | Glu | Ala | Thr | His | Arg | Leu | Ile |
| | | | 260 | | | | | 265 | | | | | 270 | | |
| Tyr | Gly | Ala | Lys | Asp | Gly | Ser | Gly | Gln | Arg | Tyr | Leu | Ala | Trp | Ser | Gly |
| | | | 275 | | | | | 280 | | | | | 285 | | |
| His | Ser | Ala | Arg | Val | Gly | Ala | Ala | Arg | Asp | Met | Ala | Arg | Ala | Gly | Val |
| | 290 | | | | | 295 | | | | | 300 | | | | |
| Ser | Ile | Ala | Glu | Ile | Met | Gln | Ala | Gly | Gly | Trp | Thr | Thr | Val | Glu | Ser |
| 305 | | | | | 310 | | | | | 315 | | | | | 320 |
| Val | Met | Asn | Tyr | Ile | Arg | Asn | Leu | Asp | Ser | Glu | Thr | Gly | Ala | Met | Val |
| | | | | 325 | | | | | 330 | | | | | 335 | |
| Arg | Leu | Leu | Glu | Asp | Asp | Asp | | | | | | | | | |
| | | | 340 | | | | | | | | | | | | |

<210> SEQ ID NO 53
<211> LENGTH: 343
<212> TYPE: PRT
<213> ORGANISM: Artificial Sequence
<220> FEATURE:
<223> OTHER INFORMATION: Tre3-94

<400> SEQUENCE: 53

```
Met Ser Lys Leu Leu Thr Val His Arg Asn Leu Ser Ala Leu Leu Val
1               5                   10                  15

Asp Ala Thr Ser Asp Glu Thr Arg Lys Asn Leu Met Asp Val Leu Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Gly Val Arg Asp Tyr Leu Leu Tyr Leu Gln Ala
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Leu Ser Asp Ser Asp Ala
            100                 105                 110

Val Ser Leu Val Met Arg Arg Ile Arg Arg Glu Asn Val Asp Ala Gly
        115                 120                 125

Glu Arg Ala Lys Gln Ala Leu Ala Phe Glu Arg Thr Asp Leu Asp Gln
    130                 135                 140

Val Arg Ser Leu Met Gly Ser Ser Glu Arg Cys Gln Asp Ile Arg Ser
145                 150                 155                 160

Leu Ala Leu Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Glu Leu Val Glu Arg Trp
210                 215                 220

Ile Ser Val Ser Gly Val Ala Asp Asp Pro Asn Asn Tyr Leu Phe Cys
225                 230                 235                 240

Pro Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Asp Asn
            340
```

<210> SEQ ID NO 54
<211> LENGTH: 343
<212> TYPE: PRT
<213> ORGANISM: Artificial Sequence
<220> FEATURE:
<223> OTHER INFORMATION: Tre3-96

<400> SEQUENCE: 54

Met Ser Lys Leu Gln Thr Val His Arg Asn Leu Ser Ala Leu Leu Val
1               5                   10                  15

Asp Ala Thr Ser Asp Glu Thr Arg Lys Asn Leu Met Asp Val Phe Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu His Leu Gln Ala
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Gly Gln Asp Ile Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Arg Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Ile Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 55
<211> LENGTH: 343
<212> TYPE: PRT
<213> ORGANISM: Artificial Sequence
<220> FEATURE:
<223> OTHER INFORMATION: Tre3-101

<400> SEQUENCE: 55

Met Ser Lys Leu Leu Thr Val His Gln Asn Leu Ser Ala Leu Leu Val
1               5                   10                  15

```
Asp Ala Thr Ser Asp Glu Ala Arg Lys Asn Leu Ala Asp Val Phe Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asp Asn Arg Lys Trp Phe
    50                  55                  60

Pro Ala Glu Pro Glu Asp Val Arg Asp Tyr Leu Leu His Leu Gln Thr
65                  70                  75                  80

Arg Gly Leu Ala Val Asn Thr Ile Gln Gln His Leu Ala Gln Leu Asn
                85                  90                  95

Met Leu His Arg Arg Ser Gly Leu Ala Arg Pro Gly Asp Ser Asn Ala
            100                 105                 110

Val Ser Leu Val Ile Arg Arg Ile Arg Arg Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Gly Gln Asp Ile Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Ile Asn Gly Val Ala Ala Pro Ser Ala Ala Ser Gln Leu
                245                 250                 255

Ser Thr Tyr Thr Leu Gln Gly Ile Phe Lys Ala Ala His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 56
<211> LENGTH: 343
<212> TYPE: PRT
<213> ORGANISM: Artificial Sequence
<220> FEATURE:
<223> OTHER INFORMATION: Tre3-103

<400> SEQUENCE: 56

Met Ser Glu Leu Gln Thr Val His His Ser Leu Ser Ala Leu Leu Val
1               5                   10                  15

Asp Ala Thr Ser Asp Glu Ala Arg Lys Asn Leu Ala Asp Val Phe Arg
            20                  25                  30
```

```
Asp Arg Gln Ala Phe Ser Glu His Thr Trp Lys Val Leu Leu Ser Val
            35                  40                  45

Cys Arg Thr Trp Ala Ala Trp Cys Lys Leu Asn Asn Arg Lys Trp Phe
     50                  55                  60

Pro Ala Glu Pro Glu Asp Val Arg Asp Tyr Leu Leu His Leu Gln Thr
 65                  70                  75                  80

Arg Gly Leu Ala Val Asn Thr Ile Gln Gln His Leu Ala Gln Leu Asn
                 85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Glu Gln
130                 135                 140

Val Arg Ser Leu Met Glu Asn Ser Asp Arg Cys Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Thr Gly
        195                 200                 205

Val Glu Lys Ala Leu Ser Leu Gly Val Thr Lys Leu Val Glu Arg Trp
    210                 215                 220

Ile Ser Ala Ser Gly Val Ala Asp Asp Pro Asn Asn Tyr Leu Phe Cys
225                 230                 235                 240

Pro Val Arg Ile Asn Gly Val Ala Ala Pro Ser Ala Ala Ser Gln Leu
                245                 250                 255

Ser Thr Ser Ala Leu Gln Gly Ile Phe Ala Ala His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Asp
            340

<210> SEQ ID NO 57
<211> LENGTH: 343
<212> TYPE: PRT
<213> ORGANISM: Artificial Sequence
<220> FEATURE:
<223> OTHER INFORMATION: Tre3-106

<400> SEQUENCE: 57

Met Ser Glu Leu Gln Thr Leu His Arg Asn Leu Ser Ala Leu Leu Val
 1               5                  10                  15

Asp Ala Thr Ser Asp Glu Thr Arg Lys Asn Leu Met Asp Val Phe Arg
                 20                  25                  30

Asp Arg Gln Ala Phe Ser Glu His Thr Trp Lys Val Leu Leu Ser Val
            35                  40                  45
```

Cys Arg Thr Trp Ala Ala Trp Cys Lys Leu Asn Asn Arg Lys Trp Phe
            50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asn Ala
            100                 105                 110

Val Ser Leu Val Met Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
130                 135                 140

Val Arg Ala Leu Met Glu Asn Ser Asp Arg Gly Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
            195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Gln Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 58
<211> LENGTH: 343
<212> TYPE: PRT
<213> ORGANISM: Artificial Sequence
<220> FEATURE:
<223> OTHER INFORMATION: Tre3-135

<400> SEQUENCE: 58

Met Ser Lys Leu Leu Thr Val His Gln Asn Leu Ser Ala Leu Leu Val
1               5                   10                  15

Asp Ala Thr Ser Asp Glu Thr Arg Lys Asn Leu Met Gly Val Leu Arg
            20                  25                  30

Asp Arg Gln Ala Phe Ser Glu His Thr Trp Lys Val Leu Leu Ser Val
        35                  40                  45

Cys Arg Thr Trp Val Ala Trp Cys Lys Leu Asn Asn Arg Arg Trp Phe
    50                  55                  60

```
Pro Ala Glu Pro Glu Asp Val Arg Asp Tyr Leu Leu His Leu Gln Val
 65                  70                  75                  80

Arg Gly Leu Ala Val Asn Thr Ile Gln Gln His Leu Ala Gln Leu Asn
                 85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
        115                 120                 125

Glu Arg Thr Lys Gln Ala Leu Ala Phe Glu Arg Thr Asp Phe Asp Gln
    130                 135                 140

Val Arg Ala Leu Met Gly Asn Ser Asp Arg Gly Gln Asp Ile Arg Ser
145                 150                 155                 160

Leu Ala Phe Leu Gly Ile Ala Tyr Asn Thr Leu Leu Arg Ile Ser Glu
                165                 170                 175

Ile Ala Arg Ile Arg Val Lys Asp Ile Ser Arg Thr Asn Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Arg Val Thr Lys Leu Val Glu Arg Trp
    210                 215                 220

Ile Ser Val Ser Gly Val Ala Gly Asp Pro Asn Asn Tyr Leu Phe Cys
225                 230                 235                 240

Gln Val Arg Lys Asn Gly Val Ala Val Pro Ser Ala Thr Ser Gln Leu
                245                 250                 255

Ser Thr Ser Ala Leu Gln Gly Ile Phe Gly Ala Ala His Cys Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Asp Asp
            340

<210> SEQ ID NO 59
<211> LENGTH: 343
<212> TYPE: PRT
<213> ORGANISM: Artificial Sequence
<220> FEATURE:
<223> OTHER INFORMATION: Tre3-002

<400> SEQUENCE: 59

Met Ser Asn Leu Leu Thr Leu His Gln Asn Leu Ser Ala Leu Leu Val
 1               5                  10                  15

Asp Val Thr Ser Asp Glu Val Arg Lys Asn Leu Met Asp Val Phe Arg
                 20                  25                  30

Asp Arg Gln Ala Phe Ser Glu His Thr Trp Lys Val Leu Leu Ser Val
             35                  40                  45

Cys Arg Thr Trp Ala Ala Trp Cys Lys Leu Asn Asn Arg Lys Trp Phe
         50                  55                  60

Pro Ala Glu Pro Glu Asp Val Arg Asp Tyr Leu Leu His Leu Gln Val
 65                  70                  75                  80
```

```
Arg Gly Leu Ala Val Asn Thr Ile Gln Gln His Leu Ala Gln Leu Asn
                85                  90                  95

Met Leu His Arg Arg Ser Gly Leu Pro Arg Leu Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
130                 135                 140

Val Arg Ser Leu Met Glu Asp Ser Asp Arg Gly Gln Asp Ile Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Val Lys Asp Ile Ser Arg Thr Asp Gly Gly Arg
            180                 185                 190

Ile Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Val Pro Ser Ala Thr Ser Gln Leu
                245                 250                 255

Ser Thr Ser Ala Leu Gln Gly Ile Phe Ala Ala Thr His Arg Gln Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asn
            340

<210> SEQ ID NO 60
<211> LENGTH: 343
<212> TYPE: PRT
<213> ORGANISM: Artificial Sequence
<220> FEATURE:
<223> OTHER INFORMATION: Tre3-023

<400> SEQUENCE: 60

Met Ser Asn Leu Gln Thr Leu His Arg Asn Leu Ser Ala Leu Leu Ile
1               5                   10                  15

Asp Ala Thr Ser Asp Glu Ala Arg Lys Asn Leu Met Asp Val Phe Arg
            20                  25                  30

Asp Arg Gln Ala Phe Ser Glu His Thr Trp Arg Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Gly Tyr Leu Leu His Leu Gln Ala
65                  70                  75                  80

Arg Gly Leu Ala Val Asn Thr Ile Gln Gln His Leu Ala Gln Leu Asn
                85                  90                  95
```

Met Leu His Arg Arg Ser Gly Leu Pro Arg Leu Ser Asp Ser Asp Ala
            100                 105                 110

Val Ser Leu Val Val Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ala Leu Met Glu Asn Ser Asp Arg Gly Gln Asp Ile Arg Thr
145                 150                 155                 160

Leu Ala Phe Leu Gly Ile Ala Tyr Asn Thr Leu Leu Arg Ile Ser Glu
                165                 170                 175

Ile Ala Arg Ile Arg Ile Lys Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Gln Val Arg Arg Asn Gly Val Ala Val Pro Ser Ala Thr Ser Gln Leu
                245                 250                 255

Ser Thr Ser Ala Leu Gln Gly Ile Phe Glu Ala Ala His His Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Pro Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 61
<211> LENGTH: 343
<212> TYPE: PRT
<213> ORGANISM: Artificial Sequence
<220> FEATURE:
<223> OTHER INFORMATION: Tre3-030

<400> SEQUENCE: 61

Met Ser Asn Leu Leu Thr Leu His Gln Asn Leu Ser Ala Leu Leu Val
1               5                   10                  15

Asp Val Thr Ser Asp Glu Val Arg Glu Asn Leu Met Asp Val Phe Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Met Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
        130                 135                 140

Val Arg Ala Leu Met Gly Asn Ser Asn Arg Cys Gln Asp Ile Arg Thr
145                 150                 155                 160

Leu Ala Phe Leu Gly Ile Ala Tyr Asn Thr Leu Leu Arg Ile Ser Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Gln Val Arg Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Asp Asp
            340

<210> SEQ ID NO 62
<211> LENGTH: 343
<212> TYPE: PRT
<213> ORGANISM: Artificial Sequence
<220> FEATURE:
<223> OTHER INFORMATION: Tre3-031

<400> SEQUENCE: 62

Met Ser Asn Leu Leu Thr Leu His Gln Asn Leu Ser Ala Leu Leu Val
1               5                   10                  15

Asp Val Thr Ser Asp Glu Ala Arg Lys Asn Leu Met Asp Val Leu Arg
            20                  25                  30

Asp Arg Gln Ala Phe Ser Glu His Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Met Arg Arg Ile Arg Lys Glu Asn Val Asp Ala Gly
        115                 120                 125

```
Glu Arg Ala Lys Gln Ala Leu Ala Phe Glu Arg Thr Asp Phe Asp Gln
            130                 135                 140

Val Arg Ser Leu Met Glu Asn Ser Asp Cys Cys Gln Asp Met Arg Thr
145                 150                 155                 160

Leu Ala Phe Leu Gly Val Ala Tyr Asn Thr Leu Leu Arg Ile Ser Glu
                165                 170                 175

Ile Ala Arg Ile Arg Ile Lys Asp Ile Ser Arg Thr Asp Gly Gly Arg
            180                 185                 190

Met Leu Ile His Ile Ser Arg Thr Lys Thr Leu Val Ser Thr Ala Gly
            195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Gln Val Arg Val Asn Gly Val Ala Ala Pro Ser Ala Thr Asn Gln Leu
                245                 250                 255

Ser Ala Tyr Thr Leu Gln Arg Ile Phe Ala Ala His Arg Leu Ile
                260                 265                 270

Tyr Gly Ala Lys Asp Asp Ser Gly Arg Arg Tyr Leu Ala Trp Ser Gly
            275                 280                 285

His Ser Ala Arg Val Gly Ala Ala Arg Asp Met Ala Arg Ala Gly Val
            290                 295                 300

Pro Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 63
<211> LENGTH: 343
<212> TYPE: PRT
<213> ORGANISM: Artificial Sequence
<220> FEATURE:
<223> OTHER INFORMATION: Tre3-033

<400> SEQUENCE: 63

Met Ser Asn Leu Leu Thr Leu His Gln Asn Leu Ser Ala Leu Leu Val
1               5                   10                  15

Asp Ala Thr Ser Asp Glu Ala Arg Lys Asn Leu Met Asp Val Leu Arg
                20                  25                  30

Asp Arg Gln Ala Phe Ser Glu His Thr Trp Lys Val Leu Leu Ser Val
            35                  40                  45

Cys Arg Thr Trp Ala Ala Trp Cys Lys Leu Asn Asn Arg Lys Trp Phe
50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
            115                 120                 125

Glu Arg Ala Lys Gln Ala Leu Ala Phe Glu Arg Thr Asp Leu Asp Gln
            130                 135                 140
```

```
Val Arg Ser Leu Met Glu Asp Ser Asp Arg Cys Gln Asp Ile Arg Asn
145                 150                 155                 160

Leu Ala Leu Leu Gly Val Ala Tyr Asn Thr Leu Leu Arg Ile Ser Glu
                165                 170                 175

Ile Ala Lys Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
            195                 200                 205

Val Glu Lys Ala Leu Ser Leu Gly Val Thr Lys Leu Val Glu Arg Trp
            210                 215                 220

Ile Ser Val Ser Gly Val Ala Asn Asp Pro Asn Asn Tyr Leu Phe Cys
225                 230                 235                 240

Gln Val Arg Lys Asn Gly Val Ala Val Pro Ser Ala Thr Ser Arg Leu
                245                 250                 255

Ser Thr Ser Ala Leu Gln Gly Ile Phe Glu Ala Ala His Arg Leu Ile
                260                 265                 270

Tyr Gly Ala Lys Asp Asn Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Asp Asp
            340

<210> SEQ ID NO 64
<211> LENGTH: 343
<212> TYPE: PRT
<213> ORGANISM: Artificial Sequence
<220> FEATURE:
<223> OTHER INFORMATION: Tre3-039

<400> SEQUENCE: 64

Met Ser Asn Leu Leu Thr Ser His Gln Asn Leu Ser Ala Leu Leu Val
1               5                   10                  15

Asp Val Thr Ser Asp Glu Val Arg Lys Asn Leu Met Asp Val Phe Arg
                20                  25                  30

Asp Arg Gln Ala Phe Ser Glu His Thr Trp Lys Val Leu Leu Ser Val
            35                  40                  45

Cys Arg Thr Trp Ala Ala Trp Cys Lys Leu Asn Asn Arg Lys Trp Phe
50                  55                  60

Pro Ala Glu Pro Glu Asp Val Arg Asp Tyr Leu Leu His Leu Gln Val
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Pro Gly Asp Ser Asp Ala
            100                 105                 110

Val Ser Leu Val Ile Arg Arg Ile Arg Arg Glu Asn Val Asp Ala Gly
            115                 120                 125

Glu Arg Ala Lys Gln Ala Leu Ala Phe Glu Arg Thr Asp Phe Glu Gln
            130                 135                 140

Val Arg Ser Leu Met Glu Asn Ser Asp Arg Gly Gln Asp Ile Arg Asn
145                 150                 155                 160
```

```
Leu Ala Leu Leu Gly Ile Ala Tyr Asn Thr Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Glu Leu Val Glu Arg Trp
            210                 215                 220

Ile Ser Val Ser Gly Val Ala Asp Asp Pro Asn Asn Tyr Leu Phe Cys
225                 230                 235                 240

Arg Val Lys Lys Asn Gly Val Ala Val Pro Ser Ala Thr Ser Gln Leu
                245                 250                 255

Ser Thr Ser Ala Leu Gln Gly Ile Phe Glu Ala Thr His Arg Leu Ile
                260                 265                 270

Tyr Gly Ala Lys Asp Gly Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 65
<211> LENGTH: 351
<212> TYPE: PRT
<213> ORGANISM: Artificial Sequence
<220> FEATURE:
<223> OTHER INFORMATION: Tre 1.0
<220> FEATURE:
<221> NAME/KEY: Signal
<222> LOCATION: (2)..(9)
<223> OTHER INFORMATION: Nuclear localisation sequence (NLS) for
      directing the protein into the nucleus of mammalian cells

<400> SEQUENCE: 65

Met Val Pro Lys Lys Arg Lys Val Ser Asn Leu Leu Thr Leu His
1               5                   10                  15

His Ser Leu Pro Ala Leu Pro Ala Asp Ala Thr Ser Asp Glu Val Arg
            20                  25                  30

Lys Asn Leu Met Asp Val Phe Arg Asp Arg Pro Ala Phe Ser Glu His
            35                  40                  45

Thr Trp Glu Met Leu Leu Ser Val Cys Arg Ser Trp Ala Ala Trp Cys
        50                  55                  60

Lys Leu Asn Asn Arg Lys Trp Phe Pro Ala Glu Pro Glu Asp Val Arg
65                  70                  75                  80

Asp Tyr Leu Leu His Leu Gln Ala Arg Gly Leu Ala Val Lys Thr Ile
                85                  90                  95

Gln Gln His Leu Cys Arg Leu Asn Met Leu His Arg Arg Ser Gly Leu
            100                 105                 110

Pro Arg Pro Ser Asp Ser Asn Ala Val Ser Leu Val Met Arg Arg Ile
            115                 120                 125

Arg Lys Glu Asn Val Asp Ala Gly Glu Arg Thr Lys Gln Ala Leu Ala
        130                 135                 140

Phe Glu Arg Thr Asp Phe Asp Gln Val Arg Ser Leu Met Glu Asn Ser
```

-continued

```
145                 150                 155                 160

Asp Arg Cys Gln Asp Ile Arg Asn Leu Ala Phe Leu Gly Val Ala Tyr
            165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
            195                 200                 205

Lys Thr Leu Val Ser Thr Ala Gly Val Glu Lys Ala Leu Ser Leu Gly
            210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Arg Tyr Gly Val Ala
            245                 250                 255

Ala Pro Ser Ala Thr Ser Gln Leu Ser Thr Tyr Ala Leu Gln Arg Ile
            260                 265                 270

Phe Glu Ala Thr His Arg Leu Ile Tyr Gly Ala Lys Asp Asp Ser Gly
            275                 280                 285

Gln Arg Tyr Leu Ala Trp Ser Gly His Ser Ala Arg Val Gly Ala Ala
            290                 295                 300

Arg Asp Met Ala Arg Ala Gly Val Ser Ile Pro Glu Ile Met Gln Ala
305                 310                 315                 320

Gly Gly Trp Thr Thr Val Asn Ser Val Met Asn Tyr Ile Arg Asn Leu
            325                 330                 335

Asp Ser Glu Thr Gly Ala Met Val Arg Leu Leu Glu Asp Gly Asp
            340                 345                 350
```